United States Patent
Shi et al.

(10) Patent No.: US 6,482,923 B1
(45) Date of Patent: Nov. 19, 2002

(54) INTERLEUKIN 17-LIKE RECEPTOR PROTEIN

(75) Inventors: Yanggu Shi, Gaithersburg, MD (US); Steve M. Ruben, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/268,311

(22) Filed: Mar. 16, 1999

Related U.S. Application Data

(63) Continuation-in-part of application No. 09/154,219, filed on Sep. 16, 1998.
(60) Provisional application No. 60/059,133, filed on Sep. 17, 1997.

(51) Int. Cl.$^7$ ...................... C07K 14/705; C07K 14/71; C07K 14/715
(52) U.S. Cl. ........................ 530/350; 530/351; 514/2; 514/12
(58) Field of Search ................................. 530/350, 351; 514/2, 12; 435/69.1

(56) References Cited

U.S. PATENT DOCUMENTS 5,194,596 A * 3/1993 Tischer et al.
5,350,836 A * 9/1994 Kopchick et al.

FOREIGN PATENT DOCUMENTS

| WO | WO 95/14772 | 6/1995 |
| WO | WO 96/29408 A1 | 9/1996 |
| WO | WO 98/20165 | 5/1998 |
| WO | WO 98/58529 | 12/1998 |
| WO | WO 99/35263 | 7/1999 |

OTHER PUBLICATIONS

Murdoch et al., 2000, Blood 95:3032–3043.*
Ji et al., 1998, J. Biol. Chem. 273:17299–17302.*
Benjamin et al., 1998, Development 125:1591–1598.*
Vukicevic et al., 1996, PNAS USA 93:9021–9026.*
Massague, 1987, Cell 49:437–438.*
Pilbeam et al., 1993, Bone 14:717–720.*
Skolnick et al., 2000, Trends in Biotech. 18:34–39.*
Bork, 2000, Genome Research 10:398–400.*
Doerks et al., 1998, Trends in Genetics 14:248–250.*
Smith et al., 1997, Nature Biotechnology 15:1222–1223.*
Brenner, 1999, Trends in Genetics 15:132–133.*
Bork, 1998, Trends in Genetics 12:425–427.*
Yao et al. (1995) Immunity 3:811–821.
Genbank Accession No. AQ309936 (Dec. 21, 1998).
Genbank Accession No. AQ240146 (Sep. 28, 1998).
Genbank Accession No. AQ113232 (Aug. 28, 1998).
Genbank Database Accession No. AA514396 (Aug. 18, 1997).
Genbank Database Accession No. AA287951 (Aug. 14, 1997).
Genbank Database Accession No. W61239 (Oct. 15, 1996).
Genbank Database Accession No. R74129 (Jun. 5, 1995).
Genbank Database Accession No. H25941 (Jul. 10, 1995).
Genbank Database Accession No. T96740 (Mar. 27, 1995).
Genbank Database Accession No. H25975 (Jul. 10, 1995).
Genbank Database Accession No. T96629 (Mar. 27, 1995).
Genbank Database Accession No. N56060 (Feb. 20, 1996).
Genbank Database Accession No. AA007528 (May 9, 1997).
Genbank Database Accession No. AA007529 (May 9, 1997).
Genbank Database Accession No. T97745 (Mar. 29, 1995).
Genbank Accession No. R74038 (Jun. 5, 1995).
Genbank Accession No. T98361 (Mar. 31, 1995).
Genbank Accession No. D25960 (Nov. 30, 1995).
Genbank Accession No. T97852 (Mar. 29, 1995).
Genbank Accession No. T98360 (Mar. 31, 1995).
Genbank Accession No. W61238 (Oct. 15, 1996).
Genbank Accession No. AA677205 (Dec. 19, 1997).
Genbank Accession No. AI032064 (Aug. 28, 1998).
Genbank Accession No. AA847767 (Mar. 31, 1998).
Genbank Accession No. AA732635 (Jan. 23, 1998).
Genbank Accession No. AA832389 (Mar. 18, 1998).
Genbank Accession No. AA836217 (Mar. 25, 1998).
Genbank Accession No. AI033911 (Aug. 28, 1998).
Genbank Accession No. AI034244 (Aug. 28, 1998).

* cited by examiner

*Primary Examiner*—Elizabeth Kemmerer
(74) *Attorney, Agent, or Firm*—Human Genome Sciences, Inc.

(57) ABSTRACT

The present invention relates to a novel IL17RLP protein which is a member of the interleukin (IL)-17 receptor family. In particular, isolated nucleic acid molecules are provided encoding the human IL17RLP protein. IL17RLP polypeptides are also provided as are vectors, host cells and recombinant methods for producing the same. The invention further relates to screening methods for identifying agonists and antagonists of IL17RLP activity. Also provided are diagnostic methods for detecting immune system-related disorders and therapeutic methods for treating immune system-related disorders.

44 Claims, 5 Drawing Sheets

Figure 1A
IL17RLP Nucleotide and Amino Acid Sequence

```
  1  GCACGAGCGATGTCGCTCGTGCTGCTAAGCCTGGCCGCGCTGTGCAGGAGCGCCGTACCC   60
  1               M  S  L  V  L  L  S  L  A  A  L  C  R  S  A  V  P    17

61  CGAGAGCCGACCGTTCAATGTGGCTCTGAAACTGGGCCATCTCCAGAGTGGATGCTACAA  120
 18   R  E  P  T  V  Q  C  G  S  E  T  G  P  S  P  E  W  M  L  Q   37

121  CATGATCTAATCCCCGGAGACTTGAGGGACCTCCGAGTAGAACCTGTTACAACTAGTGTT  180
 38   H  D  L  I  P  G  D  L  R  D  L  R  V  E  P  V  T  T  S  V   57

181  GCAACAGGGGACTATTCAATTTTGATGAATGTAAGCTGGGTACTCCGGGCAGATGCCAGC  240
 58   A  T  G  D  Y  S  I  L  M  N  V  S  W  V  L  R  A  D  A  S   77
                                      Domain I 241  ATCCGCTTGTTGAAGGCCACCAAGATTTGTGTGACGGGCAAAAGCAACTTCCAGTCCTAC  300
 78   I  R  L  L  K  A  T  K  I  C  V  T  G  K  S  N  F  Q  S  Y   97
     Domain I 301  AGCTGTGTGAGGTGCAATTACACAGAGGCCTTCCAGACTCAGACCAGACCCTCTGGTGGT  360
 98   S  C  V  R  C  N  Y  T  E  A  F  Q  T  Q  T  R  P  S  G  G   117

361  AAATGGACATTTTCCTACATCGGCTTCCCTGTAGAGCTGAACACAGTCTATTTCATTGGG  420
118   K  W  T  F  S  Y  I  G  F  P  V  E  L  N  T  V  Y  F  I  G   137

421  GCCCATAATATTCCTAATGCAAATATGAATGAAGATGGCCCTTCCATGTCTGTGAATTTC  480
138   A  H  N  I  P  N  A  N  M  N  E  D  G  P  S  M  S  V  N  F   157

481  ACCTCACCAGGCTGCCTAGACCACATAATGAAATATAAAAAAAAGTGTGTCAAGGCCGGA  540
158   T  S  P  G  C  L  D  H  I  M  K  Y  K  K  K  C  V  K  A  G   177
                                                      Domain II 541  AGCCTGTGGGATCCGAACATCACTGCTTGTAAGAAGAATGAGGAGACAGTAGAAGTGAAC  600
178   S  L  W  D  P  N  I  T  A  C  K  K  N  E  E  T  V  E  V  N   197
         Domain II 601  TTCACAACCACTCCCCTGGGAAACAGATACATGGCTCTTATCCAACACAGCACTATCATC  660
198   F  T  T  T  P  L  G  N  R  Y  M  A  L  I  Q  H  S  T  I  I   217

661  GGGTTTTCTCAGGTGTTTGAGCCACACCAGAAGAAACAAACGCGAGCTTCAGTGGTGATT  720
218   G  F  S  Q  V  F  E  P  H  Q  K  K  Q  T  R  A  S  V  V  I   237
                 Domain III 721  CCAGTGACTGGGGATAGTGAAGGTGCTACGGTGCAGCTGACTCCATATTTTCCTACTTGT  780
238   P  V  T  G  D  S  E  G  A  T  V  Q  L  T  P  Y  F  P  T  C   257
```

Figure 1B
IL17RLP Nucleotide and Amino Acid Sequence

```
 781  GGCAGCGACTGCATCCGACATAAAGGAACAGTTGTGCTCTGCCCACAAACAGGCGTCCCT   840
 258   G  S  D  C  I  R  H  K  G  T  V  V  L  C  P  Q  T  G  V  P    277
              Domain IV                             ,Domain V 841  TTCCCTCTGGATAACAACAAAAGCAAGCCGGGAGGCTGGCTGCCTCTCCTCCTGCTGTCT   900
 278   F  P  L  D  N  N  K  S  K  P  G  G  W  L  P  L  L  L  L  S   297
         Domain V 901  CTGCTGGTGGCCACATGGGTGCTGGTGGCAGGGATCTATCTAATGTGGAGGCACGAAAGG   960
 298   L  L  V  A  T  W  V  L  V  A  G  I  Y  L  M  W  R  H  E  R   317

961  ATCAAGAAGACTTCCTTTTCTACCACCACACTACTGCCCCCCATTAAGGTTCTTGTGGTT  1020
 318   I  K  K, T  S  F  S  T  T  T  L  L  P  P  I  K  V  L  V  V    337
                                            Domain VI 1021  TACCCATCTGAAATATGTTTCCATCACACAATTTGTTACTTCACTGAATTTCTTCAAAAC  1080
 338   Y  P  S  E  I  C  F  H  H  T  I  C  Y  F  T  E  F  L  Q  N    357
       Domain VI 1081  CATTGCAGAAGTGAGGTCATCCTTGAAAAGTGGCAGAAAAAGAAAATAGCAGAGATGGGT  1140
 358   H  C  R  S  E  V  I  L  E  K  W  Q  K  K  K  I  A  E  M  G    377
              Domain VII                           Domain VIII 1141  CCAGTGCAGTGGCTTGCCACTCAAAAGAAGGCAGCAGACAAAGTCGTCTTCCTTCTTTCC  1200
 378   P  V  Q  W  L  A  T  Q  K  K  A  A  D  K  V  V  F  L  S       397

1201  AATGACGTCAACAGTGTGTGCGATGGTACCTGTGGCAAGAGCGAGGGCAGTCCCAGTGAG  1260
 398   N  D  V  N  S  V  C  D  G  T  C  G  K  S  E  G  S  P  S  E    417

1261  AACTCTCAAGACTCTTCCCCTTGCCTTTAACCTTTTCTGCAGTGATCTAAGAAGCCAGAT  1320
 418   N  S  Q  D  S  S  P  C  L                                     426

1321  TCATCTGCACAAATACGTGGTGGTCTACTTTAGAGAGATTGATACAAAAGACGATTACAA  1380

1381  TGCTCTCAGTGTCTGCCCCAAGTACCACCTCATGAAGGATGCCACTGCTTTCTGTGCAGA  1440

1441  ACTTCTCCATGTCAAGTAGCAGGTGTCAGCAGGAAAAAGATCACAAGCCTGCCACGATGG  1500

1501  CTGCTGCTCCTTGTAGCCCACCCATGAGAAGCAAGWGACCTTAAAGGCTTCCTATCCCAC  1560

1561  CAATTACAGGGAAAAAACGTGTGATGATCCTGAAGCTTACTATGCAGCCTACAAACAGCC  1620

1621  TTAGTAATTAAAACATTTTATACCAATAAAATTTTCAAATATTGCTAACTAATGTAGCAT  1680
```

Figure 1C
IL17RLP Nucleotide and Amino Acid Sequence

1681 TAACTAACGATTGGAAACTACATTTACAACTTCAAAGCTGTTTTATACATAGAAATCAAT 1740

1741 TACAGTTTTAATTGAAAACTATAACCATTTTGATAATGCAACAATAAAGCATCTTCAGCC 1800

1801 AAAAAAAAAAAAAAA 1816

Figure 2
IL17RLP vs. murine IL17R

Percent Similarity: 49.879    Percent Identity: 28.571

IL17RLP.aa
x
mIL17R.aa

```
  1 MSLVLLLSLAALCRS.AVPRE....PTVQCGSE.........TGPSPEWMLQ  37
    ::::||  |..|..: | ||    |.. |: |          |. ...|: .
 16 LGWLLLLLNVLAPGRASPRLLDFPAPVCAQEGLSCRVKNSTCLDDSWIHP    65

38 HDLIPGDLRDLRVEPVTTSVATGDYSILMNVSWVLRADASIRLLKATKIC    87
    .:|.|:. ::: ::  ..|.. |:.  :::|.|.|..||||  .|.:..::
 66 KNLTPSSPKNIYINLSVSSTQHGELVPVLHVEWTLQTDASILYLEGAELS   115

88 VTGKSNFQSYSCVRCNYTEAFQTQTRPSGGKWTFSYIGFPVELNTVYFIG   137
    |  . ...   :..  ||: .: .:|  : :    :| ||: |.|: . | :.
116 VLQLNTNERL.CVKFQFLSMLQHHRK....RWRFSFSHFVVDPGQEYEVT   160

138 AHNIPNANMNEDGPSMSVNFTSPGCLDHIMKYKKKCVKAGSLWDPNITAC   187
    .|::|.:   ::|.  .|   : |:| |   ||  ...||..||||||||.
161 VHHLPKPIPDGDPNHKSKIIFVPDCEDSKMKMTTSCVSSGSLWDPNITVE   210

188 KKNEETVEVNFTTTPLGNRYMALIQ.......HSTIIGFSQVFEPHQKK.   229
    . ::: :  |:||    :...| .|::       ||.:  ...|:|.|:|..
211 TLDTQHLRVDFTLWNESTPYQVLLESFSDSENHSCFDVVKQIFAPRQEEF   260

230 QTRASVVIPVTGD..SEGATVQLTPYFPTCGSDCIRHKGTV..VLCPQTG   275
    :  ||.|.:.:.   :    ||: |:|..|  .||:||  .||   .:...|.
261 HQRANVTFTLSKFHWCCHHHVQVQPFFSSCLNDCLRHAVTVPCPVISNTT   310

276 VPFPLDNNKSKPGGWLPLL......LLSLLVATWVLVAGIYLMWRHERIK   319
    || |:      ::::||:       |:..:|...|:|  |:: ||  . .
311 VPKPV.......ADYIPLWVYGLITLIAILLVGSVIVLIICMTWRLSGAD   353

320 KTSFS............TTTLLPPIKVLVVYPSEICFHHTICY.FTEF    354
    ... :             _.|.. |.| ||::||..: .:. .:.. |.:|
354 QEKHGDDSKINGILPVADLTPPPLRPRKVWIVYSADHPLYVEVVLKFAQF   403

355 LQNHCRSEVILEKWQKKKIAEMGPVQWLATQKK....AADKVVFLLSNDV   400
    | . | .|| |: :::.. |.|:|.: |:. ||.    ...|::;| |.:.
404 LITACGTEVALDLLEEQVISEVGVMTWVSRQKQEMVESNSKIIILCSRGT   453

401 NSVCDGTCGKSEGSPSENSQDSSPC    425
    .. .:. |..|...  .::....|.
454 QAKWKAILGWAEPAVQLRCDHWKPA   478
```

IL17RLP Protein Analysis

SEQUENCE LISTING

```
<160> NUMBER OF SEQ ID NOS: 18

<210> SEQ ID NO 1
<211> LENGTH: 1816
<212> TYPE: DNA
<213> ORGANISM: Homo sapiens
<220> FEATURE:
<221> NAME/KEY: CDS
<222> LOCATION: (10)..(1287)
<220> FEATURE:
<221> NAME/KEY: mat_peptide
<222> LOCATION: (67)..(1287)
<220> FEATURE:
<221> NAME/KEY: sig_peptide
<222> LOCATION: (10)..(66)

<400> SEQUENCE: 1 gcacgagcg atg tcg ctc gtg ctg cta agc ctg gcc gcg ctg tgc agg agc        51
           Met Ser Leu Val Leu Leu Ser Leu Ala Ala Leu Cys Arg Ser
                   -15                      -10 gcc gta ccc cga gag ccg acc gtt caa tgt ggc tct gaa act ggg cca          99
Ala Val Pro Arg Glu Pro Thr Val Gln Cys Gly Ser Glu Thr Gly Pro
 -5             -1   1               5                    10 tct cca gag tgg atg cta caa cat gat cta atc ccc gga gac ttg agg         147
Ser Pro Glu Trp Met Leu Gln His Asp Leu Ile Pro Gly Asp Leu Arg
            15                  20                  25 gac ctc cga gta gaa cct gtt aca act agt gtt gca aca ggg gac tat         195
Asp Leu Arg Val Glu Pro Val Thr Thr Ser Val Ala Thr Gly Asp Tyr
        30                  35                  40 tca att ttg atg aat gta agc tgg gta ctc cgg gca gat gcc agc atc         243
Ser Ile Leu Met Asn Val Ser Trp Val Leu Arg Ala Asp Ala Ser Ile
    45                  50                  55 cgc ttg ttg aag gcc acc aag att tgt gtg acg ggc aaa agc aac ttc         291
Arg Leu Leu Lys Ala Thr Lys Ile Cys Val Thr Gly Lys Ser Asn Phe
 60                  65                  70                  75 cag tcc tac agc tgt gtg agg tgc aat tac aca gag gcc ttc cag act         339
Gln Ser Tyr Ser Cys Val Arg Cys Asn Tyr Thr Glu Ala Phe Gln Thr
                 80                  85                  90 cag acc aga ccc tct ggt ggt aaa tgg aca ttt tcc tac atc ggc ttc         387
Gln Thr Arg Pro Ser Gly Gly Lys Trp Thr Phe Ser Tyr Ile Gly Phe
             95                 100                 105 cct gta gag ctg aac aca gtc tat ttc att ggg gcc cat aat att cct         435
Pro Val Glu Leu Asn Thr Val Tyr Phe Ile Gly Ala His Asn Ile Pro
        110                 115                 120 aat gca aat atg aat gaa gat ggc cct tcc atg tct gtg aat ttc acc         483
Asn Ala Asn Met Asn Glu Asp Gly Pro Ser Met Ser Val Asn Phe Thr
    125                 130                 135 tca cca ggc tgc cta gac cac ata atg aaa tat aaa aaa aag tgt gtc         531
Ser Pro Gly Cys Leu Asp His Ile Met Lys Tyr Lys Lys Lys Cys Val
```

```
                        140                 145                 150                 155
aag gcc gga agc ctg tgg gat ccg aac atc act gct tgt aag aag aat      579
Lys Ala Gly Ser Leu Trp Asp Pro Asn Ile Thr Ala Cys Lys Lys Asn
                160                 165                 170 gag gag aca gta gaa gtg aac ttc aca acc act ccc ctg gga aac aga      627
Glu Glu Thr Val Glu Val Asn Phe Thr Thr Thr Pro Leu Gly Asn Arg
            175                 180                 185 tac atg gct ctt atc caa cac agc act atc atc ggg ttt tct cag gtg      675
Tyr Met Ala Leu Ile Gln His Ser Thr Ile Ile Gly Phe Ser Gln Val
        190                 195                 200 ttt gag cca cac cag aag aaa caa acg cga gct tca gtg gtg att cca      723
Phe Glu Pro His Gln Lys Lys Gln Thr Arg Ala Ser Val Val Ile Pro
    205                 210                 215 gtg act ggg gat agt gaa ggt gct acg gtg cag ctg act cca tat ttt      771
Val Thr Gly Asp Ser Glu Gly Ala Thr Val Gln Leu Thr Pro Tyr Phe
220                 225                 230                 235 cct act tgt ggc agc gac tgc atc cga cat aaa gga aca gtt gtg ctc      819
Pro Thr Cys Gly Ser Asp Cys Ile Arg His Lys Gly Thr Val Val Leu
                240                 245                 250 tgc cca caa aca ggc gtc cct ttc cct ctg gat aac aac aaa agc aag      867
Cys Pro Gln Thr Gly Val Pro Phe Pro Leu Asp Asn Asn Lys Ser Lys
            255                 260                 265 ccg gga ggc tgg ctg cct ctc ctc ctg ctg tct ctg ctg gtg gcc aca      915
Pro Gly Gly Trp Leu Pro Leu Leu Leu Leu Ser Leu Leu Val Ala Thr
        270                 275                 280 tgg gtg ctg gtg gca ggg atc tat cta atg tgg agg cac gaa agg atc      963
Trp Val Leu Val Ala Gly Ile Tyr Leu Met Trp Arg His Glu Arg Ile
    285                 290                 295 aag aag act tcc ttt tct acc acc aca cta ctg ccc ccc att aag gtt     1011
Lys Lys Thr Ser Phe Ser Thr Thr Thr Leu Leu Pro Pro Ile Lys Val
300                 305                 310                 315 ctt gtg gtt tac cca tct gaa ata tgt ttc cat cac aca att tgt tac     1059
Leu Val Val Tyr Pro Ser Glu Ile Cys Phe His His Thr Ile Cys Tyr
                320                 325                 330 ttc act gaa ttt ctt caa aac cat tgc aga agt gag gtc atc ctt gaa     1107
Phe Thr Glu Phe Leu Gln Asn His Cys Arg Ser Glu Val Ile Leu Glu
            335                 340                 345 aag tgg cag aaa aag aaa ata gca gag atg ggt cca gtg cag tgg ctt     1155
Lys Trp Gln Lys Lys Lys Ile Ala Glu Met Gly Pro Val Gln Trp Leu
        350                 355                 360 gcc act caa aag aag gca gca gac aaa gtc gtc ttc ctt ctt tcc aat     1203
Ala Thr Gln Lys Lys Ala Ala Asp Lys Val Val Phe Leu Leu Ser Asn
    365                 370                 375 gac gtc aac agt gtg tgc gat ggt acc tgt ggc aag agc gag ggc agt     1251
Asp Val Asn Ser Val Cys Asp Gly Thr Cys Gly Lys Ser Glu Gly Ser
380                 385                 390                 395 ccc agt gag aac tct caa gac tct tcc cct tgc ctt taacctttc           1297
Pro Ser Glu Asn Ser Gln Asp Ser Ser Pro Cys Leu
                400                 405 tgcagtgatc taagaagcca gattcatctg cacaaatacg tggtggtcta ctttagagag   1357
attgatacaa aagacgatta caatgctctc agtgtctgcc ccaagtacca cctcatgaag   1417
gatgccactg ctttctgtgc agaacttctc catgtcaagt agcaggtgtc agcaggaaaa   1477
agatcacaag cctgccacga tggctgctgc tccttgtagc ccacccatga gaagcaagwg   1537
accttaaagg cttcctatcc caccaattac agggaaaaaa cgtgtgatga tcctgaagct   1597
tactatgcag cctacaaaca gccttagtaa ttaaaacatt ttataccaat aaaattttca   1657
aatattgcta actaatgtag cattaactaa cgattggaaa ctacatttac aacttcaaag   1717
```

```
ctgttttata catagaaatc aattacagtt ttaattgaaa actataacca ttttgataat      1777
gcaacaataa agcatcttca gccaaaaaaa aaaaaaaa                              1816
```

<210> SEQ ID NO 2
<211> LENGTH: 426
<212> TYPE: PRT
<213> ORGANISM: Homo sapiens

<400> SEQUENCE: 2

```
Met Ser Leu Val Leu Leu Ser Leu Ala Ala Leu Cys Arg Ser Ala Val
                -15                 -10                  -5

Pro Arg Glu Pro Thr Val Gln Cys Gly Ser Glu Thr Gly Pro Ser Pro
         -1   1                   5                  10

Glu Trp Met Leu Gln His Asp Leu Ile Pro Gly Asp Leu Arg Asp Leu
     15                  20                  25

Arg Val Glu Pro Val Thr Thr Ser Val Ala Thr Gly Asp Tyr Ser Ile
 30                  35                  40                  45

Leu Met Asn Val Ser Trp Val Leu Arg Ala Asp Ala Ser Ile Arg Leu
                 50                  55                  60

Leu Lys Ala Thr Lys Ile Cys Val Thr Gly Lys Ser Asn Phe Gln Ser
                 65                  70                  75

Tyr Ser Cys Val Arg Cys Asn Tyr Thr Glu Ala Phe Gln Thr Gln Thr
             80                  85                  90

Arg Pro Ser Gly Gly Lys Trp Thr Phe Ser Tyr Ile Gly Phe Pro Val
         95                 100                 105

Glu Leu Asn Thr Val Tyr Phe Ile Gly Ala His Asn Ile Pro Asn Ala
110                 115                 120                 125

Asn Met Asn Glu Asp Gly Pro Ser Met Ser Val Asn Phe Thr Ser Pro
                130                 135                 140

Gly Cys Leu Asp His Ile Met Lys Tyr Lys Lys Cys Val Lys Ala
                145                 150                 155

Gly Ser Leu Trp Asp Pro Asn Ile Thr Ala Cys Lys Lys Asn Glu Glu
            160                 165                 170

Thr Val Glu Val Asn Phe Thr Thr Thr Pro Leu Gly Asn Arg Tyr Met
175                 180                 185

Ala Leu Ile Gln His Ser Thr Ile Ile Gly Phe Ser Gln Val Phe Glu
190                 195                 200                 205

Pro His Gln Lys Lys Gln Thr Arg Ala Ser Val Ile Pro Val Thr
                210                 215                 220

Gly Asp Ser Glu Gly Ala Thr Val Gln Leu Thr Pro Tyr Phe Pro Thr
            225                 230                 235

Cys Gly Ser Asp Cys Ile Arg His Lys Gly Thr Val Val Leu Cys Pro
            240                 245                 250

Gln Thr Gly Val Pro Phe Pro Leu Asp Asn Asn Lys Ser Lys Pro Gly
        255                 260                 265

Gly Trp Leu Pro Leu Leu Leu Ser Leu Leu Val Ala Thr Trp Val
270                 275                 280                 285

Leu Val Ala Gly Ile Tyr Leu Met Trp Arg His Glu Arg Ile Lys Lys
                290                 295                 300

Thr Ser Phe Ser Thr Thr Thr Leu Leu Pro Pro Ile Lys Val Leu Val
            305                 310                 315

Val Tyr Pro Ser Glu Ile Cys Phe His His Thr Ile Cys Tyr Phe Thr
        320                 325                 330
```

-continued

```
Glu Phe Leu Gln Asn His Cys Arg Ser Glu Val Ile Leu Glu Lys Trp
    335                 340                 345

Gln Lys Lys Lys Ile Ala Glu Met Gly Pro Val Gln Trp Leu Ala Thr
350                 355                 360                 365

Gln Lys Lys Ala Ala Asp Lys Val Val Phe Leu Ser Asn Asp Val
                370                 375                 380

Asn Ser Val Cys Asp Gly Thr Cys Gly Lys Ser Glu Gly Ser Pro Ser
                385                 390                 395

Glu Asn Ser Gln Asp Ser Ser Pro Cys Leu
                400                 405

<210> SEQ ID NO 3
<211> LENGTH: 426
<212> TYPE: PRT
<213> ORGANISM: Homo sapiens

<400> SEQUENCE: 3

Met Ser Leu Val Leu Leu Ser Leu Ala Ala Leu Cys Arg Ser Ala Val
  1               5                  10                  15

Pro Arg Glu Pro Thr Val Gln Cys Gly Ser Glu Thr Gly Pro Ser Pro
                 20                  25                  30

Glu Trp Met Leu Gln His Asp Leu Ile Pro Gly Asp Leu Arg Asp Leu
             35                  40                  45

Arg Val Glu Pro Val Thr Thr Ser Val Ala Thr Gly Asp Tyr Ser Ile
         50                  55                  60

Leu Met Asn Val Ser Trp Val Leu Arg Ala Asp Ala Ser Ile Arg Leu
 65                  70                  75                  80

Leu Lys Ala Thr Lys Ile Cys Val Thr Gly Lys Ser Asn Phe Gln Ser
                 85                  90                  95

Tyr Ser Cys Val Arg Cys Asn Tyr Thr Glu Ala Phe Gln Thr Gln Thr
                100                 105                 110

Arg Pro Ser Gly Gly Lys Trp Thr Phe Ser Tyr Ile Gly Phe Pro Val
            115                 120                 125

Glu Leu Asn Thr Val Tyr Phe Ile Gly Ala His Asn Ile Pro Asn Ala
        130                 135                 140

Asn Met Asn Glu Asp Gly Pro Ser Met Ser Val Asn Phe Thr Ser Pro
145                 150                 155                 160

Gly Cys Leu Asp His Ile Met Lys Tyr Lys Lys Cys Val Lys Ala
                165                 170                 175

Gly Ser Leu Trp Asp Pro Asn Ile Thr Ala Cys Lys Lys Asn Glu Glu
            180                 185                 190

Thr Val Glu Val Asn Phe Thr Thr Thr Pro Leu Gly Asn Arg Tyr Met
        195                 200                 205

Ala Leu Ile Gln His Ser Thr Ile Ile Gly Phe Ser Gln Val Phe Glu
    210                 215                 220

Pro His Gln Lys Lys Gln Thr Arg Ala Ser Val Val Ile Pro Val Thr
225                 230                 235                 240

Gly Asp Ser Glu Gly Ala Thr Val Gln Leu Thr Pro Tyr Phe Pro Thr
                245                 250                 255

Cys Gly Ser Asp Cys Ile Arg His Lys Gly Thr Val Val Leu Cys Pro
                260                 265                 270

Gln Thr Gly Val Pro Phe Pro Leu Asp Asn Asn Lys Ser Lys Pro Gly
            275                 280                 285

Gly Trp Leu Pro Leu Leu Leu Ser Leu Leu Val Ala Thr Trp Val
        290                 295                 300
```

-continued

Leu Val Ala Gly Ile Tyr Leu Met Trp Arg His Glu Arg Ile Lys Lys
305                 310                 315                 320

Thr Ser Phe Ser Thr Thr Thr Leu Leu Pro Pro Ile Lys Val Leu Val
            325                 330                 335

Val Tyr Pro Ser Glu Ile Cys Phe His His Thr Ile Cys Tyr Phe Thr
            340                 345                 350

Glu Phe Leu Gln Asn His Cys Arg Ser Glu Val Ile Leu Glu Lys Trp
            355                 360                 365

Gln Lys Lys Lys Ile Ala Glu Met Gly Pro Val Gln Trp Leu Ala Thr
            370                 375                 380

Gln Lys Lys Ala Ala Asp Lys Val Val Phe Leu Leu Ser Asn Asp Val
385                 390                 395                 400

Asn Ser Val Cys Asp Gly Thr Cys Gly Lys Ser Glu Gly Ser Pro Ser
            405                 410                 415

Glu Asn Ser Gln Asp Ser Ser Pro Cys Leu
            420                 425

<210> SEQ ID NO 4
<211> LENGTH: 409
<212> TYPE: DNA
<213> ORGANISM: Homo sapiens
<220> FEATURE:
<221> NAME/KEY: misc_feature
<222> LOCATION: (17)
<223> OTHER INFORMATION: n equals a, t, g or c
<220> FEATURE:
<221> NAME/KEY: misc_feature
<222> LOCATION: (65)
<223> OTHER INFORMATION: n equals a, t, g or c
<220> FEATURE:
<221> NAME/KEY: misc_feature
<222> LOCATION: (148)
<223> OTHER INFORMATION: n equals a, t, g or c
<220> FEATURE:
<221> NAME/KEY: misc_feature
<222> LOCATION: (160)
<223> OTHER INFORMATION: n equals a, t, g or c
<220> FEATURE:
<221> NAME/KEY: misc_feature
<222> LOCATION: (362)
<223> OTHER INFORMATION: n equals a, t, g or c
<220> FEATURE:
<221> NAME/KEY: misc_feature
<222> LOCATION: (373)
<223> OTHER INFORMATION: n equals a, t, g or c
<220> FEATURE:
<221> NAME/KEY: misc_feature
<222> LOCATION: (388)
<223> OTHER INFORMATION: n equals a, t, g or c
<220> FEATURE:
<221> NAME/KEY: misc_feature
<222> LOCATION: (406)
<223> OTHER INFORMATION: n equals a, t, g or c

<400> SEQUENCE: 4
aattcggcac gagattnatc tgcacaaata cgtggtggtc tactttagag agattgatac      60
aaaanacgat tacaatgctc tcagtgtctg ccccaagtac cacctcatga aggatgccac    120
tgctttctgt gcagaacttc tccatgtnaa gtagcaggtn tcagcaggaa aaagatcaca    180
agcctgccac gatggctgct gctccttgta gcccacccat gagaagcaag agaccttaaa    240
ggcttcctat cccaccaatt acagggaaaa aacgtgtgat gatcctgaag ctttactatg    300
cagcctacaa acagccttag taattaaaac atttttatac ccataaaatt tttcaaatat    360
tngttaacta atngtagcat taactaangt ttgggaacta catttncaa                409

```
<210> SEQ ID NO 5
<211> LENGTH: 327
<212> TYPE: DNA
<213> ORGANISM: Homo sapiens
<220> FEATURE:
<221> NAME/KEY: misc_feature
<222> LOCATION: (10)
<223> OTHER INFORMATION: n equals a, t, g or c
<220> FEATURE:
<221> NAME/KEY: misc_feature
<222> LOCATION: (39)
<223> OTHER INFORMATION: n equals a, t, g or c
<220> FEATURE:
<221> NAME/KEY: misc_feature
<222> LOCATION: (42)
<223> OTHER INFORMATION: n equals a, t, g or c
<220> FEATURE:
<221> NAME/KEY: misc_feature
<222> LOCATION: (44)
<223> OTHER INFORMATION: n equals a, t, g or c
<220> FEATURE:
<221> NAME/KEY: misc_feature
<222> LOCATION: (53)
<223> OTHER INFORMATION: n equals a, t, g or c
<220> FEATURE:
<221> NAME/KEY: misc_feature
<222> LOCATION: (106)
<223> OTHER INFORMATION: n equals a, t, g or c
<220> FEATURE:
<221> NAME/KEY: misc_feature
<222> LOCATION: (120)
<223> OTHER INFORMATION: n equals a, t, g or c
<220> FEATURE:
<221> NAME/KEY: misc_feature
<222> LOCATION: (128)
<223> OTHER INFORMATION: n equals a, t, g or c
<220> FEATURE:
<221> NAME/KEY: misc_feature
<222> LOCATION: (163)
<223> OTHER INFORMATION: n equals a, t, g or c
<220> FEATURE:
<221> NAME/KEY: misc_feature
<222> LOCATION: (173)
<223> OTHER INFORMATION: n equals a, t, g or c
<220> FEATURE:
<221> NAME/KEY: misc_feature
<222> LOCATION: (210)
<223> OTHER INFORMATION: n equals a, t, g or c
<220> FEATURE:
<221> NAME/KEY: misc_feature
<222> LOCATION: (223)
<223> OTHER INFORMATION: n equals a, t, g or c
<220> FEATURE:
<221> NAME/KEY: misc_feature
<222> LOCATION: (233)
<223> OTHER INFORMATION: n equals a, t, g or c
<220> FEATURE:
<221> NAME/KEY: misc_feature
<222> LOCATION: (238)
<223> OTHER INFORMATION: n equals a, t, g or c
<220> FEATURE:
<221> NAME/KEY: misc_feature
<222> LOCATION: (241)
<223> OTHER INFORMATION: n equals a, t, g or c
<220> FEATURE:
<221> NAME/KEY: misc_feature
<222> LOCATION: (247)
<223> OTHER INFORMATION: n equals a, t, g or c
<220> FEATURE:
<221> NAME/KEY: misc_feature
<222> LOCATION: (251)
<223> OTHER INFORMATION: n equals a, t, g or c
<220> FEATURE:
<221> NAME/KEY: misc_feature
<222> LOCATION: (261)
<223> OTHER INFORMATION: n equals a, t g or c
<220> FEATURE:
<221> NAME/KEY: misc_feature
```

<222> LOCATION: (267)
<223> OTHER INFORMATION: n equals a, t, g or c
<220> FEATURE:
<221> NAME/KEY: misc_feature
<222> LOCATION: (269)
<223> OTHER INFORMATION: n equals a, t, g or c
<220> FEATURE:
<221> NAME/KEY: misc_feature
<222> LOCATION: (274)
<223> OTHER INFORMATION: n equals a, t, g or c
<220> FEATURE:
<221> NAME/KEY: misc_feature
<222> LOCATION: (277)
<223> OTHER INFORMATION: n equals a, t, g or c
<220> FEATURE:
<221> NAME/KEY: misc_feature
<222> LOCATION: (279)
<223> OTHER INFORMATION: n equals a, t, g or c
<220> FEATURE:
<221> NAME/KEY: misc_feature
<222> LOCATION: (285)
<223> OTHER INFORMATION: n equals a, t, g or c
<220> FEATURE:
<221> NAME/KEY: misc_feature
<222> LOCATION: (289)
<223> OTHER INFORMATION: n equals a, t, g or c
<220> FEATURE:
<221> NAME/KEY: misc_feature
<222> LOCATION: (293)
<223> OTHER INFORMATION: n equals a, t, g or c
<220> FEATURE:
<221> NAME/KEY: misc_feature
<222> LOCATION: (295)
<223> OTHER INFORMATION: n equals a, t, g or c
<220> FEATURE:
<221> NAME/KEY: misc_feature
<222> LOCATION: (302)
<223> OTHER INFORMATION: n equals a, t, g or c
<220> FEATURE:
<221> NAME/KEY: misc_feature
<222> LOCATION: (305)
<223> OTHER INFORMATION: n equals a, t, g or c
<220> FEATURE:
<221> NAME/KEY: misc_feature
<222> LOCATION: (312)
<223> OTHER INFORMATION: n equals a, t, g or c

<400> SEQUENCE: 5
aattcggcan agcccggcga tgtcgctcgt gctgctagnc tngnngcgct gtncaggagc      60
gccgtacccc gagagccgac cgttcaatgt ggctctgaaa ctgggncatc tccagagtgn     120
nttgctanaa catgatctaa tcccgggaga cttgagggac ctncgagtag agnctgttac     180
aactagtgtt gcaacagggg actattcaan ttgatgaatg tanctgggta ctncgggnag     240
ntgccancat ncgttttttg naggctnang tttngtntnn cgggnaaang tantntcagt     300
cntanagtgt tngaggtgca ttaaaaa                                         327

<210> SEQ ID NO 6
<211> LENGTH: 35
<212> TYPE: DNA
<213> ORGANISM: Homo sapiens

<400> SEQUENCE: 6
cgcccatggc cgaccgttca atgtggctct gaaac                                35

<210> SEQ ID NO 7
<211> LENGTH: 35
<212> TYPE: DNA
<213> ORGANISM: Homo sapiens

<400> SEQUENCE: 7

-continued

```
cgcccatggc cgaccgttca atgtggctct gaaac                                    35

<210> SEQ ID NO 8
<211> LENGTH: 34
<212> TYPE: DNA
<213> ORGANISM: Homo sapiens

<400> SEQUENCE: 8
cgcggatcca tgtcgctcgt gctgctaagc ctgg                                     34

<210> SEQ ID NO 9
<211> LENGTH: 26
<212> TYPE: DNA
<213> ORGANISM: Homo sapiens

<400> SEQUENCE: 9
cgcggtaccc cagcctcccg gcttgc                                              26

<210> SEQ ID NO 10
<211> LENGTH: 129
<212> TYPE: DNA
<213> ORGANISM: Homo sapiens

<400> SEQUENCE: 10
gccggatccg ccaccatgaa ctccttctcc acaagcgcct tcggtccagt tgccttctcc         60
ctggggctgc tcctggtgtt gcctgctgcc ttccctgccc cagtatgtcg ctcgtgctgc        120
taagcctgg                                                                129

<210> SEQ ID NO 11
<211> LENGTH: 28
<212> TYPE: DNA
<213> ORGANISM: Homo sapiens

<400> SEQUENCE: 11
ggccgggtac cccagcctcc cggcttgc                                            28

<210> SEQ ID NO 12
<211> LENGTH: 43
<212> TYPE: DNA
<213> ORGANISM: Homo sapiens

<400> SEQUENCE: 12
ctagccggat ccgccaccat gtcgctcgtg ctgctaagcc tgg                           43

<210> SEQ ID NO 13
<211> LENGTH: 28
<212> TYPE: DNA
<213> ORGANISM: Homo sapiens

<400> SEQUENCE: 13
ggccgggtac cccagcctcc cggcttgc                                            28

<210> SEQ ID NO 14
<211> LENGTH: 17
<212> TYPE: PRT
<213> ORGANISM: Homo sapiens

<400> SEQUENCE: 14

Pro Arg Glu Pro Thr Val Gln Cys Gly Ser Glu Thr Gly Pro Ser Pro
 1               5                  10                  15

Glu
```

```
<210> SEQ ID NO 15
<211> LENGTH: 10
<212> TYPE: PRT
<213> ORGANISM: Homo sapiens

<400> SEQUENCE: 15

Leu Asp His Ile Met Lys Tyr Lys Lys Lys
 1               5                  10

<210> SEQ ID NO 16
<211> LENGTH: 10
<212> TYPE: PRT
<213> ORGANISM: Homo sapiens

<400> SEQUENCE: 16

Lys Lys Asn Glu Glu Thr Val Glu Val Asn
 1               5                  10

<210> SEQ ID NO 17
<211> LENGTH: 1918
<212> TYPE: DNA
<213> ORGANISM: Homo sapiens
<220> FEATURE:
<221> NAME/KEY: CDS
<222> LOCATION: (111)..(1409)
<220> FEATURE:
<221> NAME/KEY: misc_feature
<222> LOCATION: (29)
<223> OTHER INFORMATION: n equals a, t, g or c
<220> FEATURE:
<221> NAME/KEY: misc_feature
<222> LOCATION: (101)
<223> OTHER INFORMATION: n equals a, t, g or c

<400> SEQUENCE: 17
aagctcgaaa ttaaccctca ctaaagggna acaaaagctg gagctccacc gcggtggcgg      60
ccgctctaga actagtggat cccccgggct gcaggaattc ngcacgagcg atg tcg       116
                                                      Met Ser
                                                        1 ctc gtg ctg cta agc ctg gcc gcg ctg tgc agg agc gcc gta ccc cga     164
Leu Val Leu Leu Ser Leu Ala Ala Leu Cys Arg Ser Ala Val Pro Arg
        5                  10                  15 gag ccg acc gtt caa tgt ggc tct gaa act ggg cca tct cca gag tgg     212
Glu Pro Thr Val Gln Cys Gly Ser Glu Thr Gly Pro Ser Pro Glu Trp
 20                  25                  30 atg cta caa cat gat cta atc ccc gga gac ttg agg gac ctc cga gta     260
Met Leu Gln His Asp Leu Ile Pro Gly Asp Leu Arg Asp Leu Arg Val
 35                  40                  45                  50 gaa cct gtt aca act agt gtt gca aca ggg gac tat tca att ttg atg     308
Glu Pro Val Thr Thr Ser Val Ala Thr Gly Asp Tyr Ser Ile Leu Met
                 55                  60                  65 aat gta agc tgg gta ctc cgg gca gat gcc agc atc cgc ttg ttg aag     356
Asn Val Ser Trp Val Leu Arg Ala Asp Ala Ser Ile Arg Leu Leu Lys
         70                  75                  80 gcc acc aag att tgt gtg acg ggc aaa agc aac ttc cag tcc tac agc     404
Ala Thr Lys Ile Cys Val Thr Gly Lys Ser Asn Phe Gln Ser Tyr Ser
         85                  90                  95 tgt gtg agg tgc aat tac aca gag gcc ttc cag act cag acc aga ccc     452
Cys Val Arg Cys Asn Tyr Thr Glu Ala Phe Gln Thr Gln Thr Arg Pro
    100                 105                 110 tct ggt ggt aaa tgg aca ttt tcc tac atc ggc ttc cct gta gag ctg     500
Ser Gly Gly Lys Trp Thr Phe Ser Tyr Ile Gly Phe Pro Val Glu Leu
115                 120                 125                 130
```

```
                                        -continued aac aca gtc tat ttc att ggg gcc cat aat att cct aat gca aat atg     548
Asn Thr Val Tyr Phe Ile Gly Ala His Asn Ile Pro Asn Ala Asn Met
            135                 140                 145 aat gaa gat ggc cct tcc atg tct gtg aat ttc acc tca cca ggc tgc     596
Asn Glu Asp Gly Pro Ser Met Ser Val Asn Phe Thr Ser Pro Gly Cys
150                 155                 160 cta gac cac ata atg aaa tat aaa aaa aag tgt gtc aag gcc gga agc     644
Leu Asp His Ile Met Lys Tyr Lys Lys Lys Cys Val Lys Ala Gly Ser
        165                 170                 175 ctg tgg gat ccg aac atc act gct tgt aag aag aat gag gag aca gta    692
Leu Trp Asp Pro Asn Ile Thr Ala Cys Lys Lys Asn Glu Glu Thr Val
180                 185                 190 gaa gtg aac ttc aca acc act ccc ctg gga aac aga tac atg gct ctt    740
Glu Val Asn Phe Thr Thr Thr Pro Leu Gly Asn Arg Tyr Met Ala Leu
195                 200                 205                 210 atc caa cac agc act atc atc ggg ttt tct cag gtg ttt gag cca cac    788
Ile Gln His Ser Thr Ile Ile Gly Phe Ser Gln Val Phe Glu Pro His
            215                 220                 225 cag aag aaa caa acg cga gct tca gtg gtg att cca gtg act ggg gat    836
Gln Lys Lys Gln Thr Arg Ala Ser Val Val Ile Pro Val Thr Gly Asp
        230                 235                 240 agt gaa ggt gct acg gtg cag ctg act cca tat ttt cct act tgt ggc    884
Ser Glu Gly Ala Thr Val Gln Leu Thr Pro Tyr Phe Pro Thr Cys Gly
            245                 250                 255 agc gac tgc atc cga cat aaa gga aca gtt gtg ctc tgc cca caa aca    932
Ser Asp Cys Ile Arg His Lys Gly Thr Val Val Leu Cys Pro Gln Thr
260                 265                 270 ggc gtc cct ttc cct ctg gat aac aac aaa agc aag ccg gga ggc tgg    980
Gly Val Pro Phe Pro Leu Asp Asn Asn Lys Ser Lys Pro Gly Gly Trp
275                 280                 285                 290 ctg cct ctc ctc ctg ctg tct ctg ctg gtg gcc aca tgg gtg ctg gtg   1028
Leu Pro Leu Leu Leu Leu Ser Leu Leu Val Ala Thr Trp Val Leu Val
            295                 300                 305 gca ggg atc tat cta atg tgg agg cac gaa agg atc aag aag act tcc   1076
Ala Gly Ile Tyr Leu Met Trp Arg His Glu Arg Ile Lys Lys Thr Ser
        310                 315                 320 ttt tct acc acc aca cta ctg ccc ccc att aag gtt ctt gtg gtt tac   1124
Phe Ser Thr Thr Thr Leu Leu Pro Pro Ile Lys Val Leu Val Val Tyr
            325                 330                 335 cca tct gaa ata tgt ttc cat cac aca att tgt tac ttc act gaa ttt   1172
Pro Ser Glu Ile Cys Phe His His Thr Ile Cys Tyr Phe Thr Glu Phe
340                 345                 350 ctt caa aac cat tgc aga agt gag gtc atc ctt gaa aag tgg cag aaa   1220
Leu Gln Asn His Cys Arg Ser Glu Val Ile Leu Glu Lys Trp Gln Lys
355                 360                 365                 370 aag aaa ata gca gag atg ggt cca gtg cag tgg ctt gcc act caa aag   1268
Lys Lys Ile Ala Glu Met Gly Pro Val Gln Trp Leu Ala Thr Gln Lys
            375                 380                 385 aag gca gca gac aaa gtc gtc ttc ctt ctt tcc aat gac gtc aac agt   1316
Lys Ala Ala Asp Lys Val Val Phe Leu Leu Ser Asn Asp Val Asn Ser
        390                 395                 400 gtg tgc gat ggt acc tgt ggc aag agc gag ggc agt ccc agt gag aac   1364
Val Cys Asp Gly Thr Cys Gly Lys Ser Glu Gly Ser Pro Ser Glu Asn
405                 410                 415 tct caa gac tct tcc ccc ttg cct tta acc ttt tct gca gtg atc       1409
Ser Gln Asp Ser Ser Pro Leu Pro Leu Thr Phe Ser Ala Val Ile
        420                 425                 430 taagaagcca gattcatctg cacaaatacg tggtggtcta ctttagagag attgatacaa 1469 aagacgatta caatgctctc agtgtctgcc ccaagtacca cctcatgaag gatgccactg 1529
```

-continued

```
ctttctgtgc agaacttctc catgtcaagt agcaggtgtc agcaggaaaa agatcacaag    1589
cctgccacga tggctgctgc tccttgtagc ccacccatga gaagcaagag accttaaagg    1649
cttcctatcc caccaattac agggaaaaaa cgtgtgatga tcctgaagct tactatgcag    1709
cctacaaaca gccttagtaa ttaaaacatt ttataccaat aaaattttca aatattgcta    1769
actaatgtag cattaactaa cgattggaaa ctacatttac aacttcaaag ctgttttata    1829
catagaaatc aattacagtt ttaattgaaa actataacca ttttgataat gcaacaataa    1889
agcatcttca gccaaaaaaa aaaaaaaaa                                      1918
```

<210> SEQ ID NO 18
<211> LENGTH: 433
<212> TYPE: PRT
<213> ORGANISM: Homo sapiens

<400> SEQUENCE: 18

```
Met Ser Leu Val Leu Ser Leu Ala Ala Leu Cys Arg Ser Ala Val
 1               5                  10                  15

Pro Arg Glu Pro Thr Val Gln Cys Gly Ser Glu Thr Gly Pro Ser Pro
            20                  25                  30

Glu Trp Met Leu Gln His Asp Leu Ile Pro Gly Asp Leu Arg Asp Leu
        35                  40                  45

Arg Val Glu Pro Val Thr Thr Ser Val Ala Thr Gly Asp Tyr Ser Ile
    50                  55                  60

Leu Met Asn Val Ser Trp Val Leu Arg Ala Asp Ala Ser Ile Arg Leu
65                  70                  75                  80

Leu Lys Ala Thr Lys Ile Cys Val Thr Gly Lys Ser Asn Phe Gln Ser
                85                  90                  95

Tyr Ser Cys Val Arg Cys Asn Tyr Thr Glu Ala Phe Gln Thr Gln Thr
            100                 105                 110

Arg Pro Ser Gly Gly Lys Trp Thr Phe Ser Tyr Ile Gly Phe Pro Val
        115                 120                 125

Glu Leu Asn Thr Val Tyr Phe Ile Gly Ala His Asn Ile Pro Asn Ala
    130                 135                 140

Asn Met Asn Glu Asp Gly Pro Ser Met Ser Val Asn Phe Thr Ser Pro
145                 150                 155                 160

Gly Cys Leu Asp His Ile Met Lys Tyr Lys Lys Cys Val Lys Ala
                165                 170                 175

Gly Ser Leu Trp Asp Pro Asn Ile Thr Ala Cys Lys Lys Asn Glu Glu
            180                 185                 190

Thr Val Glu Val Asn Phe Thr Thr Thr Pro Leu Gly Asn Arg Tyr Met
        195                 200                 205

Ala Leu Ile Gln His Ser Thr Ile Ile Gly Phe Ser Gln Val Phe Glu
    210                 215                 220

Pro His Gln Lys Lys Gln Thr Arg Ala Ser Val Val Ile Pro Val Thr
225                 230                 235                 240

Gly Asp Ser Glu Gly Ala Thr Val Gln Leu Thr Pro Tyr Phe Pro Thr
                245                 250                 255

Cys Gly Ser Asp Cys Ile Arg His Lys Gly Thr Val Val Leu Cys Pro
            260                 265                 270

Gln Thr Gly Val Pro Phe Pro Leu Asp Asn Asn Lys Ser Lys Pro Gly
        275                 280                 285

Gly Trp Leu Pro Leu Leu Leu Leu Ser Leu Leu Val Ala Thr Trp Val
    290                 295                 300
```

-continued

```
Leu Val Ala Gly Ile Tyr Leu Met Trp Arg His Glu Arg Ile Lys Lys
305             310             315             320

Thr Ser Phe Ser Thr Thr Thr Leu Leu Pro Pro Ile Lys Val Leu Val
            325             330             335

Val Tyr Pro Ser Glu Ile Cys Phe His His Thr Ile Cys Tyr Phe Thr
            340             345             350

Glu Phe Leu Gln Asn His Cys Arg Ser Glu Val Ile Leu Glu Lys Trp
        355             360             365

Gln Lys Lys Lys Ile Ala Glu Met Gly Pro Val Gln Trp Leu Ala Thr
    370             375             380

Gln Lys Lys Ala Ala Asp Lys Val Val Phe Leu Leu Ser Asn Asp Val
385             390             395             400

Asn Ser Val Cys Asp Gly Thr Cys Gly Lys Ser Glu Gly Ser Pro Ser
            405             410             415

Glu Asn Ser Gln Asp Ser Ser Pro Leu Pro Leu Thr Phe Ser Ala Val
            420             425             430

Ile
```

INTERLEUKIN 17-LIKE RECEPTOR PROTEIN

This application claims benefit under 35 U.S.C. §120 of the filing date of copending continuation-in-part U.S. application Ser. No. 09/154,219, filed on Sep. 16, 1998, pending, which is hereby incorporated by reference in its entirety. This application also claims benefit under 35 U.S.C. §119(e) of the filing date of copending U.S. Provisional Application Serial No. 60/059,133, filed on Sep. 17, 1997, which is hereby incorporated by reference in its entirety.

FIELD OF THE INVENTION

The present invention relates to a novel human gene encoding a polypeptide which is a member of the interleukin (IL)-17 receptor family. More specifically, isolated nucleic acid molecules are provided encoding a human polypeptide named Interleukin 17-Receptor-Like Protein, hereinafter referred to as IL17RLP. IL17RLP polypeptides are also provided, as are vectors, host cells and recombinant methods for producing the same. Also provided are diagnostic methods for detecting disorders related to the immune system and therapeutic methods for treating such disorders. The invention further relates to screening methods for identifying agonists and antagonists of IL17RLP activity.

BACKGROUND OF THE INVENTION

Cytokines typically exert their respective biochemical and physiological effects by binding to specific receptor molecules. Receptor binding will then stimulate specific signal transduction pathways (Kishimoto, T., et al., *Cell* 76:253–262 (1994). The specific interactions of cytokines with their receptors are often the primary regulators of a wide variety of cellular process including activation, proliferation, and differentiation (Arai, K. -I, et al.,*Ann. Rev. Biochem.* 59:783–836 (1990); Paul, W. and Seder, R., *Cell* 76:241–251 (1994)).

Human interleukin (IL)-17 was only recently identified. IL-17 is a 155 amino acid polypetide which was molecularly cloned from a CD4+ T-cell cDNA library (Yao, Z., et al.,*J. Immunol.* 155:5483–5486 (1995)). The IL-17 polypeptide contains an N-terminal signal peptide and contains approximately 72% identity at the amino acid level with a T-cell trophic herpesvirus saimiri (HVS) gene designated HVS13. High levels of IL-17 are secreted from CD4-positive primary peripheral blood leukocytes (PBL) upon stimulation (Yao, Z., et al.,*Immunity* 3:811–821 (1995)). Treatment of fibroblasts with IL-17, HVS13, or another murine homologue, designated CTLA8, activate signal transduction pathways and result in the stimulation of the NF-κB transcription factor family, the secretion of IL-6, and the costimulation of T-cell proliferation (Yao, Z., et al., *Immunity* 3:811–821 (1995)).

An HVS13-Fc fusion protein was used to isolate a murine IL-17 receptor molecule which does not appear to belong to any of the previously described cytokine receptor families (Yao, Z., et al., *Immunity* 3:811–821 (1995)). The murine IL-17 receptor (mIL-17R) is predicted to encode a type I transmembrane protein of 864 amino acids with an apparent molecular mass of 97.8 kDa. mIL-17R is predicted to possess an N-terminal signal peptide with a cleavage site between alanine-31 and serine-32. The molecule also contains a 291 amino acid extracellular domain, a 21 amino acid transmembrane domain, and a 521 amino acid cytoplasmic tail. A soluble recombinant IL-17R molecule consisting of 323 amino acids of the extracellular domain of IL-17R fused to the Fc portion of human IgG1 was able to significantly inhibit IL-17-induced IL-6 production by murine NIH-3T3 cells (supra).

Interestingly, the expression of the IL-17 gene is highly restricted. It is typically observed primarily in activated T-lymphocyte memory cells (Broxmeyer, H. *J. Exp. Med.* 183:2411–2415 (1996); Fossiez, F., et al., *J. Exp. Med.* 183:2593–2603 (1996)). Conversely, the IL-17 receptor appears to be expressed in a large number of cells and tissues including (Rouvier, E., et al., *J. Immunol.* 150:5445–5456 (1993); Yao, Z., et al.,*J. Immunol.* 155:5483–5486 (1995)). It remains to be seen, however, if IL-17 itself can play an autocrine role in the expression of IL-17. IL-17 has been implicated as a causitive agent in the expression of IL-6, IL-8, G-CSF, Prostaglandin E ($PGE_2$), and intracellular adhesion molecule (ICAM)-1 (Fossiez, F., supra; Yao, Z., et al., *Immunity* 3:811–821 (1995)). Each of these molecules possesses highly relevent and potentially therapeutically valuable properties. For instance, IL-6 is involved in the regulation of hematopoietic stem and progenitor cell growth and expansion (Ikebuchi, K., et al., *Proc. Natl. Acad. Sci. USA* 84:9035–9039 (1987); Gentile, P. and Broxmeyer, H. E. *Ann. N.Y. Acad. Sci. USA* 628:74–83 (1991)). IL-8 exhibits a myelosuppressive activity for stem and immature subsets of myeloid progenitors (Broxmeyer, H. E., et al., *Ann. Hematol.* 71:235–246 (1995); Daly, T. J., et al.,*J. Biol. Chem.* 270:23282–23292 (1995)). G-CSF acts early and late to activate and stimulate hematopoiesis in general (more specifically, neutrophil hematopoiesis) while $PGE_2$ enhances erythropoiesis, suppresses lymphopoiesis and myelopoiesis in general, and strongly suppresses monocytopoiesis (Broxmeyer, H. E. *Amer. J. Ped. Hematol./Oncol.* 14:22–30 (1992); Broxmeyer, H. E. and Williams, D. E. *CRC Crit. Rev. Oncol./Hematol.* 8:173–226 (1988)).

IL-17 receptor appears to be structurally unrelated to any previously described cytokine receptor family. Despite the existence of 12 cysteine residues in the extracellular domain, their relative positions are not characteristic of receptor molecules classified as members of the immunoglobulin superfamily (Williams, A. and Barclay, A. *Annu. Rev. Immunol.* 6:381–405 (1988)), the TNFR family (Smith, C., et al., *Science* 248:1019–1023 (1990)), the hematopoietin receptor family (Cosman, D. *Cytokine* 5:95–106 (1993)), or any previously described tyrosine kinase receptors (Hanks, S., et al., *Science* 241:42–52 (1988)).

Thus, there is a need for polypeptides that function as receptor molecules for cytokines and, thereby, function in the transfer of an extracellular signal ultimately to the nucleus of the cell, since disturbances of such regulation may be involved in disorders relating to cellular activation, hemostasis, angiogenesis, tumor metastasis, cellular migration and ovulation, as well as neurogenesis. Therefore, there is a need for identification and characterization of such human polypeptides which can play a role in detecting, preventing, ameliorating or correcting such disorders.

SUMMARY OF THE INVENTION

The present invention provides isolated nucleic acid molecules comprising a polynucleotide encoding at least a portion of the IL17RLP polypeptide having the complete amino acid sequence shown in SEQ ID NO:2 or the complete amino acid sequence encoded by the cDNA clone deposited as plasmid DNA as ATCC Deposit Number 209198 on Aug. 8, 1997. The nucleotide sequence determined by sequencing the deposited IL17RLP clone, which is shown in FIGS. 1A, 1B, and 1C (SEQ ID NO:1), contains an open reading frame encoding a complete polypeptide of 426 amino acid residues, including an initiation codon encoding an N-terminal methionine at nucleotide positions 10–12, and a predicted molecular weight of about 47.1 kDa. Nucleic acid molecules of the invention include those encoding the complete amino acid sequence excepting the N-terminal methionine shown in SEQ ID NO:2, or the complete amino acid sequence excepting the N-terminal methionine encoded by the cDNA clone in ATCC Deposit Number 209198, which molecules also can encode additional amino acids fused to the N-terminus of the IL17RLP amino acid sequence.

The encoded polypeptide has a predicted leader sequence of 19 amino acids underlined in FIGS. 1A, 1B, and 1C; and the amino acid sequence of the predicted mature IL17RLP protein is also shown in FIGS. 1A, 1B, and 1C as amino acid residues 20–426, and as residues 1–407 in SEQ ID NO:2.

In another embodiment, the encoded polypeptide has a predicted leader sequence from Met-(−19) to Ser-(−6) of SEQ ID NO:2 (i.e., from Met-1 to Ser-14 of the amino acid sequence presented in FIGS. 1A, 1B, and 1C); an extracellular domain from Ala-(−5) to Trp-271 of SEQ ID NO:2 (i.e., from Ala-15 to Tyr-290 of the amino acid sequence presented in FIGS. 1A, 1B, and 1C); a transmembrane domain from Leu-272 to Leu-292 of SEQ ID NO:2 (i.e., from Leu-291 to Leu-311 of the amino acid sequence presented in FIGS. 1A, 1B, and 1C); and an intracellular domain from Met-293 to Leu407 of SEQ ID NO:2 (i.e., from Met-312 to Leu-426 of the amino acid sequence presented in FIGS. 1A, 1B, and 1C). The predicted length of the leader peptide in this embodiment is within the originally predicted range of 14–19 amino acids.

In an additional embodiment, the IL17RLP transmembrane domain may have an N-terminal boundary beginning at amino acid residue Pro-268, Gly-269, Gly-270, Trp-271 or Leu-272 of the IL17RLP sequence as shown in SEQ ID NO:2 (i.e., amino acid residues Pro-287, Gly-288, Gly-289, Trp-290 or Leu-291 of the IL17RLP sequence as shown in FIGS. 1A, 1B, and 1C) and a C-terminal boundary including amino acid residue Tyr-291, Leu-292, Met-293 or Trp-294 of the IL17RLP sequence as shown in SEQ ID NO:2 (i.e., amino acid residues Tyr-310, Leu-311, Met-312 or Trp-313 of the IL17RLP sequence as shown in FIGS. 1A, 1B, and 1C).

Thus, one aspect of the invention provides an isolated nucleic acid molecule comprising a polynucleotide comprising a nucleotide sequence selected from the group consisting of: (a) a nucleotide sequence encoding the IL17RLP polypeptide having the complete amino acid sequence in SEQ ID NO:2 (i.e., positions −19 to 407 of SEQ ID NO:2); (b) a nucleotide sequence encoding the IL17RLP polypeptide having the complete amino acid sequence in SEQ ID NO:2 excepting the N-terminal methionine (i.e., positions −18 to 407 of SEQ ID NO:2); (c) a nucleotide sequence encoding the predicted mature IL17RLP polypeptide having the amino acid sequence at positions 1 to 407 in SEQ ID NO:2; (d) a nucleotide sequence encoding a polypeptide comprising the predicted extracellular domain of the IL17RLP polypeptide having the amino acid sequence at positions 1 to 271 in SEQ ID NO:2; (e) a nucleotide sequence encoding a soluble IL17RLP polypeptide having the predicted extracellular and intracellular domains, but lacking the predicted transmembrane domain; (f) a nucleotide sequence encoding the IL17RLP polypeptide having the complete amino acid sequence encoded by the cDNA clone contained in ATCC Deposit No. 209198; (g) a nucleotide sequence encoding the IL17RLP polypeptide having the complete amino acid sequence excepting the N-terminal methionine encoded by the cDNA clone contained in ATCC Deposit No. 209198; (h) a nucleotide sequence encoding the mature IL17RLP polypeptide having the amino acid sequence encoded by the cDNA clone contained in ATCC Deposit No. 209198; (i) a nucleotide sequence encoding the extracellular domain of the IL17RLP polypeptide having the amino acid sequence encoded by the cDNA clone contained in ATCC Deposit No. 209198; and (j) a nucleotide sequence complementary to any of the nucleotide sequences in (a), (b), (c), (d), (e), (f), (g), (h) or (i) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e), (f), (g), (h) or (i), above, or a polynucleotide which hybridizes under stringent hybridization conditions to a polynucleotide in (a), (b), (c), (d), (e), (f), (g), (h) or (i), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a IL17RLP polypeptide having an amino acid sequence in (a), (b), (c), (d), (e), (f), (g) or (h), above.

An additional nucleic acid embodiment of the invention relates to an isolated nucleic acid molecule comprising a polynucleotide which encodes the amino acid sequence of an epitope-bearing portion of a IL17RLP polypeptide having an amino acid sequence in (a), (b), (c), (d), (e), (f) or (g), above. A further embodiment of the invention relates to an isolated nucleic acid molecule comprising a polynucleotide which encodes the amino acid sequence of a IL17RLP polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polynucleotide which encodes the amino acid sequence of a IL17RLP polypeptide to have an amino acid sequence which contains not more than 10, 9, 8, 7, 6, 5, 4, 3, 2 or 1 amino acid substitutions. Conservative substitutions are preferable.

In another embodiment, the present invention includes a polynucleotide of 1,918 nucleotides (SEQ ID NO:17) which encodes the IL17RLP polypeptide provided in SEQ ID NO:18. The IL17RLP of SEQ ID NO:18 differs from the IL17RLP provided in SEQ ID NO:2 only by the deletion of the C-terminal two residues (Cys-406 and Leu407 of SEQ ID NO:2) and the addition of nine amino acid residues (Leu-425 through Ile-433 of SEQ ID NO:18). The extracellular domain of IL17RLP is identical in SEQ ID NO:2 and SEQ ID NO:18. The IL17RLP polynucleotide sequence shown in SEQ ID NO:17 was derived from sequencing the HAPOR40 cDNA clone deposited with the ATCC with ATCC Deposit No. 209198 on Aug. 8, 1997.

The present invention also relates to recombinant vectors, which include the isolated nucleic acid molecules of the present invention, and to host cells containing the recombinant vectors, as well as to methods of making such vectors and host cells and for using them for production of IL17RLP polypeptides or peptides by recombinant techniques.

In accordance with a further aspect of the present invention, there is provided a process for producing such polypeptide by recombinant techniques comprising culturing recombinant prokaryotic and/or eukaryotic host cells, containing an IL17RLP nucleic acid sequence, under conditions promoting expression of said protein and subsequent recovery of said protein.

The invention further provides an isolated IL17RLP polypeptide comprising an amino acid sequence selected from the group consisting of: (a) the amino acid sequence of the full-length IL17RLP polypeptide having the complete amino acid sequence shown in SEQ ID NO:2 (i.e., positions −19 to 407 of SEQ ID NO:2); (b) the amino acid sequence of the full-length IL17RLP polypeptide having the complete amino acid sequence shown in SEQ ID NO:2 excepting the N-terminal methionine (i.e., positions −18 to 407 of SEQ ID NO:2); (c) the amino acid sequence of the mature IL17RLP polypeptide having the complete amino acid sequence shown in SEQ ID NO:2 (i.e., positions 1 to 407 of SEQ ID NO:2); (d) the amino acid sequence of the predicted extracellular domain of the IL17RLP polypeptide having the complete amino acid sequence shown in SEQ ID NO:2 (i.e., positions 1 to 271 of SEQ ID NO:2); (e) the amino acid sequence of a soluble IL17RLP polypeptide having the predicted extracellular and intracellular domains, but lacking the predicted transmembrane domain; (f) the complete amino acid sequence encoded by the cDNA clone contained in the ATCC Deposit No. 209198; (g) the complete amino acid sequence excepting the N-terminal methionine encoded by the cDNA clone contained in the ATCC Deposit No. 209198; (h) the complete amino acid sequence of the mature IL17RLP encoded by the cDNA clone contained in the ATCC Deposit No. 209198, and; (i) the complete amino acid sequence of the extracellular domain of the IL17RLP encoded by the cDNA clone contained in the ATCC Deposit No. 209198. The polypeptides of the present invention also include polypeptides having an amino acid sequence at least 80% identical, more preferably at least 90% identical, and still more preferably 95%, 96%, 97%, 98% or 99% identical to those described in (a), (b), (c), (d), (e), (f), (g), (h) or (i) above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of a IL17RLP polypeptide having an amino acid sequence described in (a), (b), (c), (d), (e), (f), (g), (h) or (i), above. Peptides or polypeptides having the amino acid sequence of an epitope-bearing portion of an IL17RLP polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

A further embodiment of the invention relates to a polypeptide which comprises the amino acid sequence of an IL17RLP polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of an IL17RLP polypeptide, which contains at least one, but not more than 20, 10, 9, 8, 7, 6, 5, 4, 3, 2 or 1 amino acid substitutions. In specific embodiments, the number of additions, substitutions, and/or deletions in the amino acid sequence of FIGS. 1A, 1B, and 1C, or fragments thereof (e.g., the mature form and/or other fragments described herein), is 1–5, 5–10, 5–25, 5–50, 10–50, 50–150, 50–200 or 100–250, conservative amino acid substitutions are preferable.

In another embodiment, the invention provides an isolated antibody that binds specifically to a IL17RLP polypeptide having an amino acid sequence described in (a), (b), (c), (d), (e), (f), (g), (h) or (i) above. The invention further provides methods for isolating antibodies that bind specifically to a IL17RLP polypeptide having an amino acid sequence as described herein. Such antibodies are useful diagnostically or therapeutically as described below.

The invention also provides for pharmaceutical compositions comprising IL17RLP polypeptides, particularly human IL7RLP polypeptides, which may be employed, for instance, to treat disorders relating to cellular activation, hemostasis, angiogenesis, tumor metastasis, cellular migration and ovulation, as well as neurogenesis. Methods of treating individuals in need of IL17RLP polypeptides are also provided.

The invention further provides compositions comprising an IL17RLP polynucleotide or an IL17RLP polypeptide for administration to cells in vitro, to cells ex vivo and to cells in vivo, or to a multicellular organism. In certain particularly preferred embodiments of this aspect of the invention, the compositions comprise an IL17RLP polynucleotide for expression of an IL17RLP polypeptide in a host organism for treatment of disease. Particularly preferred in this regard is expression in a human patient for treatment of a dysfunction associated with aberrant endogenous activity of an IL17RLP polypeptide.

The present invention also provides a screening method for identifying compounds capable of enhancing or inhibiting a biological activity of the IL17RLP polypeptide, which involves contacting a ligand which is inhibited by the IL17RLP polypeptide with the candidate compound in the presence of an IL17RLP polypeptide, assaying receptor-binding activity of the ligand in the presence of the candidate compound and of IL17RLP polypeptide, and comparing the ligand activity to a standard level of activity, the standard being assayed when contact is made between the ligand itself in the presence of the IL17RLP polypeptide and the absence of the candidate compound In this assay, an increase in ligand activity over the standard indicates that the candidate compound is an agonist of IL17RLP activity and a decrease in ligand activity compared to the standard indicates that the compound is an antagonist of IL17RLP activity.

In another aspect, a screening assay for agonists and antagonists is provided which involves determining the effect a candidate compound has on IL17RLP binding to a ligand. In particular, the method involves contacting the ligand with an IL17RLP polypeptide and a candidate compound and determining whether IL17RLP polypeptide binding to the ligand is increased or decreased due to the presence of the candidate compound. In this assay, an increase in binding of IL17RLP over the standard binding indicates that the candidate compound is an agonist of IL17RLP binding activity and a decrease in IL17RLP binding compared to the standard indicates that the compound is an antagonist of IL17RLP binding activity.

It has been discovered that IL17RLP is expressed not only in adult pulmonary tissue, but also in Crohn's Disease tissue, kidney pyramid, cortex, and medulla tissues, hippocampus, frontal cortex of the brain from a patient with epilepsy, adrenal gland tumor, striatum depression, osteclastoma, endometrial tumor, and hypothalamus from a patient with Schizophrenia. Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of the tissue(s) or cell type(s). In addition, for a number of disorders of the above tissues or cells, particularly of the immune system, significantly higher or lower levels of IL17RLP gene expression may be detected in certain tissues (e.g., cancerous and wounded tissues) or bodily fluids (e.g., serum, plasma, urine, synovial fluid or spinal fluid) taken from an individual having such a disorder, relative to a "standard" IL17RLP gene expression level, i.e., the IL17RLP expression level in healthy tissue from an individual not having the immune system disorder. Thus, the invention provides a diagnostic method useful during diagnosis of such a disorder, which involves: (a) assaying IL17RLP gene expression level in cells or body fluid of an individual; (b) comparing the IL17RLP gene expression level with a standard IL17RLP gene expression level, whereby an increase or decrease in the assayed IL17RLP gene expression level compared to the standard expression level is indicative of disorder in the immune system.

An additional aspect of the invention is related to a method for treating an individual in need of an increased level of IL17RLP activity in the body comprising administering to such an individual a composition comprising a therapeutically effective amount of an isolated IL17RLP polypeptide of the invention or an agonist thereof.

A still further aspect of the invention is related to a method for treating an individual in need of a decreased level of IL17RLP activity in the body comprising, administering to such an individual a composition comprising a therapeutically effective amount of an IL17RLP antagonist. Preferred antagonists for use in the present invention are IL17RLP-specific antibodies.

BRIEF DESCRIPTION OF THE FIGURES

FIGS. 1A, 1B, and 1C show the nucleotide sequence (SEQ ID NO:1) and deduced amino acid sequence (SEQ ID NO:2) of IL17RLP.

Figure 3:
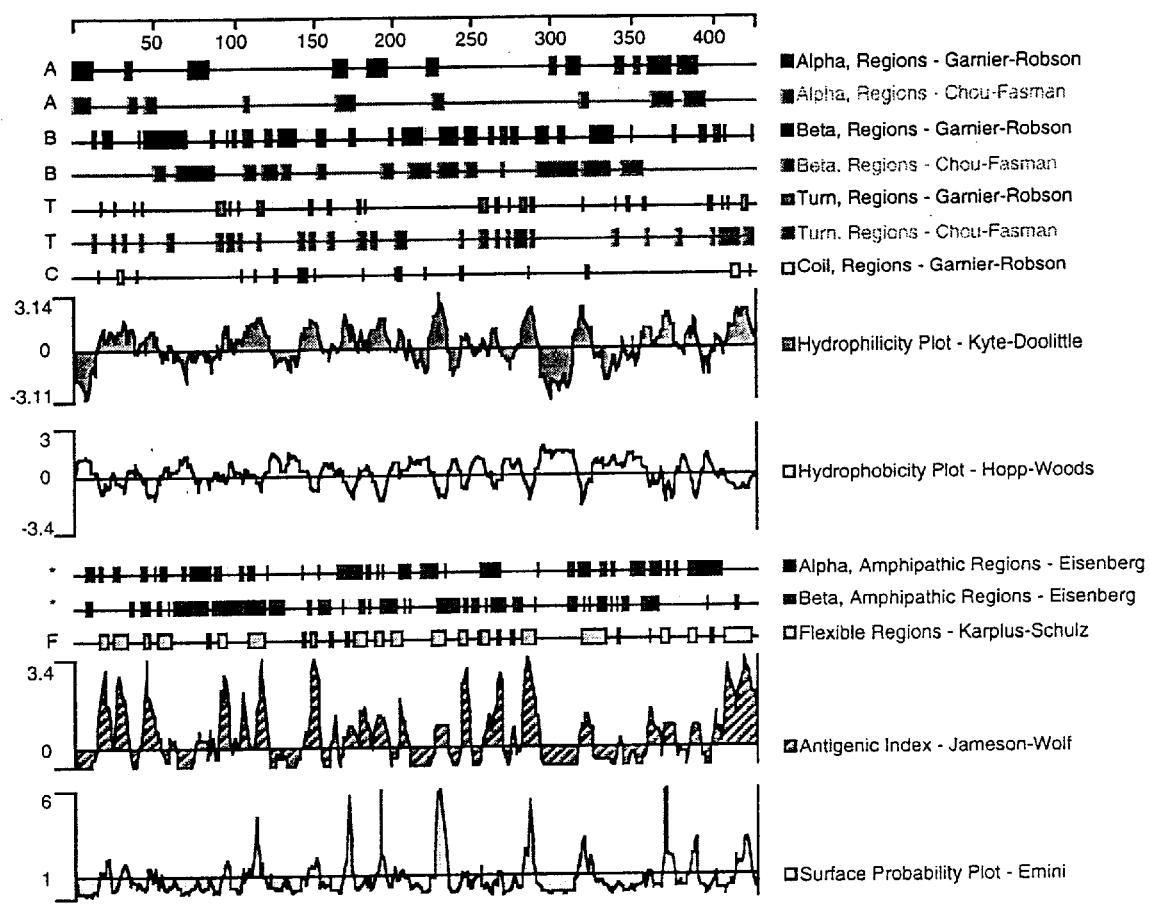

The predicted leader sequence of about 19 amino acids is underlined. Note that the methionine residue at the beginning of the leader sequence in FIGS. 1A, 1B, and 1C is shown in position number (positive) 1, whereas the leader positions in the corresponding sequence of SEQ ID NO:2 are designated with negative position numbers. Thus, the leader sequence positions 1 to 19 in FIGS. 1A, 1B, and 1C correspond to positions −19 to −1 in SEQ ID NO:2.

Six potential asparagine-linked glycosylation sites are marked in the amino acid sequence of IL17RLP. The sites are marked with the bold pound symbol (#) above the nucleotide sequence coupled with a bolded one letter abbreviation for the asparagine (N) in the amino acid sequence in FIGS. 1A, 1B, and 1C; that is, the actual asparagine residues which are potentially glycosylated is bolded in FIGS. 1A, 1B, and 1C. The potential N-linked glycosylation sequences are found at the following locations in the IL17RLP amino acid sequence: N-67 through W-70 (N-67, V-68, S-69, W-70); N-103 through E-106 (N-103, Y-104, T-105, E-106; N-156 through S-159 (N-156, F-157, T-158, S-159); N-183 through A-186 (N-183, I-184, T-185, A-186); N-197 through T-200 (N-197, F-198, T-199, T-200); and N-283 through K-286 (N-283, K-284, S-285, K-286). Two potential cAMP- and cGMP-dependent protein kinase phosphorylation sites are also marked in FIGS. 1A, 1B, and 1C with a bolded lysine symbol (K) in the IL17RLP amino acid sequence and an asterisk (*) above the first nucleotide encoding that lysine residue in the IL17RLP nucleotide sequence. The potential cAMP- and cGMP-dependent protein kinase phosphorylation sequences are found in the IL17RLP amino acid sequence at the following locations: K-141 through threonine-231 (K-228, K-229, Q-230, T-231) and K-319 through S-322 (K-319, K-320, T-321, S-322). Three potential Protein Kinase C (PKC) phosphorylation sites are also marked in FIGS. 1A, 1B, and 1C with a bolded serine or tyrosine symbol (S or T) in the IL17RLP amino acid sequence and an asterisk (*) above the first nucleotide encoding that serine tyrosine residue in the IL17RLP nucleotide sequence. The potential PKC phosphorylation sequences are found in the IL17RLP amino acid sequence at the following locations: S-77 through R-79 (S-77, I-78, R-79); T-89 through K-91 (T-89, G-90, K-91); and T-384 through K-386 (T-384, Q-385, K-386). Three potential Casein Kinase II (CK2) phosphorylation sites are also marked in FIGS. 1A, 1B, and 1C with a bolded serine symbol (S) in the IL17RLP amino acid sequence and an asterisk (*) above the first nucleotide encoding the appropriate serine residue in the IL17RLP nucleotide sequence. The potential CK2 phosphorylation sequences are found at the following locations in the IL17RLP amino acid sequence: S-178 through D-181 (S-178, L-179, W-180, D181); S-402 through D-405 (S-402, V-403, C-404, D-405); and S-414 through E-417 (S-414, P-415, S-416, E-417). A single potential myristylation site is found in the IL17RLP amino acid sequence shown in FIGS. 1A, 1B, and 1C. The potential myristylation site is marked in FIGS. 1A, 1B, and 1C with a double underline delineating the amino acid residues representing the potential myristolation site in the IL17RLP amino acid sequence. The potential myristolation site is located at the following postion in the IL17RLP amino acid sequence: G-116 through F-121 (G-116, G-117, K-118, W-119, T-120, F-121).

Mutations in one or more of the amino acid residues in the above-recited potential structural features of the IL17RLP polypeptide are contemplated as mutations which may affect biological, structural, binding or other characteristics of an IL17RLP DNA or polypeptide of the invention.

FIG. 2 shows the regions of identity between the amino acid sequences of the IL17RLP protein (SEQ ID NO:2) and translation product of the murine mRNA for IL-17 receptor (SEQ ID NO:3), determined by the computer program Bestfit (Wisconsin Sequence Analysis Package, Version 8 for Unix, Genetics Computer Group, University Research Park, 575 Science Drive, Madison, Wis. 53711) using the default parameters.

FIG. 3 shows an analysis of the IL17RLP amino acid sequence. Alpha, beta, turn and coil regions; hydrophilicity and hydrophobicity; amphipathic regions; flexible regions; antigenic index and surface probability are shown. In the "Antigenic Index or Jameson-Wolf" graph, the positive peaks indicate locations of the highly antigenic regions of the IL17RLP protein, i.e., regions from which epitope-bearing peptides of the invention can be obtained.

In the "Antigenic Index or Jameson-Wolf" graph, the positive peaks indicate locations of the highly antigenic regions of the IL17RLP protein, i.e., regions from which epitope-bearing peptides of the invention can be obtained. Non-limiting examples of antigenic polypeptides or peptides that can be used to generate IL17RLP-specific antibodies include: a polypeptide comprising amino acid residues from about a polypeptide comprising amino acid residues from about Ser-14 to about Val-22 in SEQ ID NO:2, a polypeptide comprising amino acid residues from about Cys-24 to about Pro-32 in SEQ ID NO:2, a polypeptide comprising amino acid residues from about Ile-41 to about Arg-49 in SEQ ID NO:2, a polypeptide comprising amino acid residues from about Thr-89 to about Val-97 in SEQ ID NO:2, a polypeptide comprising amino acid residues from about Thr-110 to about Lys-118 in SEQ ID NO:2, a polypeptide comprising amino acid residues from about Ala-144 to about Ser-152 in SEQ ID NO:2, a polypeptide comprising amino acid residues from about Thr-240 to about Val-248 in SEQ ID NO:2, a polypeptide comprising amino acid residues from about Gly-258 to about Thr-267 in SEQ ID NO:2, a polypeptide comprising amino acid residues from about Leu-280 to about Gly-288 in SEQ ID NO:2, a polypeptide comprising amino acid residues from about Cys-404 to about Glu-412 in SEQ ID NO:2, a polypeptide comprising amino acid residues from about Pro-415 to about Ser-423 in SEQ ID NO:2, a polypeptide comprising amino acid residues from about Gly-409 to about Glu417 in SEQ ID NO:2, and a polypeptide comprising amino acid residues from about Cys-404 to about Leu-426 in FIGS. 1A, 1B, and 1C (which is identical to the sequence shown in SEQ ID NO:2 with exception to the numbering schemes as detailed above).

The data presented in FIG. 3 are also represented in tabular form in Table I. The data presented in Table I is identical to that originally presented in FIG. 3. The columns are labeled with the headings "Res", "Position", and Roman Numerals I–XIV. The column headings refer to the following features of the amino acid sequence presented in FIG. 3 and Table I: "Res": amino acid residue of SEQ ID NO:2 or FIGS. 1A, 1B, and 1C (which is the identical sequence shown in SEQ ID NO:2, with the exception that the residues are numbered 1–426 in FIGS. 1A, 1B, and 1C and –19 through 407 in SEQ ID NO:2); "Position": position of the corresponding residue within SEQ ID NO:2 or FIGS. 1A, 1B, and 1C (which is the identical sequence shown in SEQ ID NO:2, with the exception that the residues are numbered 1–366 in FIGS. 1A, 1B, and 1C and –19 through 407 in SEQ ID NO:2); I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

DETAILED DESCRIPTION

The present invention provides isolated nucleic acid molecules comprising a polynucleotide encoding a IL17RLP polypeptide having the amino acid sequence shown in SEQ ID NO:2, which was determined by sequencing a cloned cDNA. The nucleotide sequence shown in FIGS. 1A, 1B, and 1C (SEQ ID NO:1) was obtained by sequencing the HAPOR40 clone, which was deposited on Aug. 8, 1997 at the American Type Culture Collection, 10801 University Boulevard, Manassas, Va. 20110-2209, and given accession number ATCC 209198. The deposited clone is contained in the pBluescript SK(–) plasmid (Stratagene, La Jolla, Calif.).

The IL17RLP protein of the present invention shares sequence homology with the translation product of the murine mRNA for IL-17 receptor (FIG. 2; SEQ ID NO:3). Murine IL-17 receptor is thought to be an important component of the IL-17 cytokine signal transduction pathway. IL-17 receptor appears to be structurally unrelated to any members of previously described cytokine receptor families. The IL-17/IL-17 receptor complex activates NF-kappaB activity. NF-kappaB is a transcription factor known to regulate a large number of gene products involved in growth control. NF-kappaB-induced gene products include molecules involved in immune, inflammatory, or actute phase responses, such as immunoglobulin light chain, major histocompatibility complex (MHC), IL-2R alpha chain, and cytokines such as IL-1beta, IL-6, and TNFalpha. NF-kappaB directly stimulates the HIV enhancer in T-cells and can itself be activated by different viral proteins with oncogenic potential, such as the hepatitis B virus HBX protein, EBV LMP1, and HTLV-1 Tax protein. The induction of NF-kappaB by Tax results in up-regulation of IL-2 and IL-2R and subsequently uncontrolled T-cell growth. IL-17 and HVS13, a gene product of HVS and a murine counterpart of IL-17, strongly induce IL-6 expression. IL-6 is a potent growth factor for myelomas, plasmacytomas, and-hybridomas and is involved in the growth of Lennert's Lymphoma T-cells.

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIGS. 1A, 1B, and 1C (SEQ ID NO:1), a nucleic acid molecule of the present invention encoding a IL17RLP polypeptide may be obtained using standard cloning and screening procedures, such as those for cloning cDNAs using mRNA as starting material. Illustrative of the invention, the nucleic acid molecule described in FIGS. 1A, 1B, and 1C (SEQ ID NO:1) was discovered in a cDNA library derived from human adult pulmonary tissue.

Additional clones of the same gene were also identified in cDNA libraries from the following tissues: Crohn's Disease tissue, kidney pyramid, cortex, and medulla tissues, hippocampus, frontal cortex of the brain from a patient with epilepsy, adrenal gland tumor, striatum depression, osteclastoma, endometrial tumor, and hypothalamus from a patient with Schizophrenia.

The determined nucleotide sequence of the IL17RLP cDNA of FIGS. 1A, 1B, and 1C (SEQ ID NO:1) contains an open reading frame encoding a protein of 426 amino acid residues, with an initiation codon at nucleotide positions 10–12 of the nucleotide sequence in FIGS. 1A, 1B, and 1C (SEQ ID NO:1), and a deduced molecular weight of about 47.1 kDa. The amino acid sequence of the IL17RLP protein shown in SEQ ID NO:2 is about 28.6% identical to the murine mRNA for IL-17 receptor (FIG. 2; Yao, Z., et al., Immunity 3:811–821 (1995); GenBank Accession No. U31993).

The open reading frame of the IL17RLP gene shares sequence homology with the translation product of the murine mRNA for IL-17 receptor (FIG. 2; SEQ ID NO:3). The murine IL-17 receptor is thought to be important in regulation of immune cell signal transduction cascades and the resulting regulation of cell growth, differentiation, and activation-state. The homology between the murine IL-17 receptor and IL17RLP indicates that IL17RLP may also be involved in regulation of immune cell signal transduction cascades and the resulting regulation of cell growth, differentiation, and activation-state.

As one of ordinary skill would appreciate, due to the possibilities of sequencing errors discussed above, the actual complete IL17RLP polypeptide encoded by the deposited cDNA, which comprises about 426 amino acids, may be somewhat longer or shorter. More generally, the actual open reading frame may be anywhere in the range of ±20 amino acids, more likely in the range of ±10 amino acids, of that predicted from either the first methionine codon from the N-terminus shown in FIGS. 1A, 1B, and 1C (SEQ ID NO:1). It will further be appreciated that, depending on the analytical criteria used for identifying various functional domains, the exact "address" of the extracellular, intracellular and transmembrane domains of the IL17RLP polypeptide may differ slightly from the predicted positions above. For example, the exact location of the IL17RLP extracellular domain in SEQ ID NO:2 may vary slightly (e.g., the address may "shift" by about 1 to about 20 residues, more likely about 1 to about 5 residues) depending on the criteria used to define the domain. In this case, the ends of the transmembrane domain and the beginning of the extracellular domain were predicted on the basis of the identification of the hydrophobic amino acid sequence in the above indicated positions, as shown in FIG. 3. In any event, as discussed further below, the invention further provides polypeptides having various residues deleted from the N-terminus of the complete polypeptide, including polypeptides lacking one or more amino acids from the N-terminus of the extracellular domain described herein, which constitute soluble forms of the extracellular domain of the IL17RLP protein.

In another embodiment, the present invention includes a polynucleotide of 1,918 nucleotides (SEQ ID NO:17) which encodes the IL17RLP polypeptide provided in SEQ ID NO:18. The IL17RLP of SEQ ID NO:18 differs from the IL17RLP provided in SEQ ID NO:2 only by the deletion of the C-terminal two residues (Cys-406 and Leu-407 of SEQ ID NO:2) and the addition of nine amino acid residues (Leu-425 through Ile-433 of SEQ ID NO:18). The extracellular domain of IL17RLP is identical in SEQ ID NO:2 and SEQ ID NO:18. The IL17RLP polynucleotide sequence shown in SEQ ID NO:17 was derived from sequencing the HAPOR40 cDNA clone deposited with the ATCC with ATCC Deposit No. 209198 on Aug. 8, 1997.

It will further be appreciated that, depending on the analytical criteria used for identifying the exact location of the cleavage site of the precursor form of the mature IL17RLP molecule shown in SEQ ID NO:2 may vary slightly, depending on the criteria used to define the cleavage site. In this case, the ends of the signal peptide and the beginning of the mature IL17RLP molecule were predicted using the HGSI SignalP computer algorithm. One of skill in the art will realize that another widely accepted computer algorithm used to predict potential sites of polypeptide cleavage, PSORT, will predict the cleavage of an N-terminal signal peptide from the IL17RLP polypeptide at a point slightly different from that predicted by the HGSI SignalP algorithm. In either case, as discussed further below, the invention further provides polypeptides having various residues deleted from the N-terminus of the complete polypeptide, including polypeptides corresponding to either of the predicted mature IL17RLP polypeptides described herein.

Leader and Mature Sequences

The amino acid sequence of the complete IL17RLP protein includes a leader sequence and a mature protein, as shown in SEQ ID NO:2. More in particular, the present invention provides nucleic acid molecules encoding a mature form of the IL17RLP protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature IL17RLP polypeptide having the amino acid sequence encoded by the cDNA clone identified as ATCC Deposit No. 209198. By the "mature IL17RLP polypeptide having the amino acid sequence encoded by the cDNA clone in ATCC Deposit No. 209198" is meant the mature form(s) of the IL17RLP protein produced by expression in a mammalian cell (e.g., COS cells, as described below) of the complete open reading frame encoded by the human DNA sequence of the clone contained in the deposited clone HAPOR40.

In addition, methods for predicting whether a protein has a secretory leader as well as the cleavage point for that leader sequence are available. For instance, the method of McGeoch (*Virus Res.* 3:271–286 (1985)) uses the information from a short N-terminal charged region and a subsequent uncharged region of the complete (uncleaved) protein. The method of von Heinje (*Nucleic Acids Res.* 14:4683–4690 (1986)) uses the information from the residues surrounding the cleavage site, typically residues −13 to +2 where +1 indicates the amino terminus of the mature protein. The accuracy of predicting the cleavage points of known mammalian secretory proteins for each of these methods is in the range of 75–80% (von Heinje, supra). However, the two methods do not always produce the same predicted cleavage point(s) for a given protein.

In the present case, the deduced amino acid sequence of the complete IL17RLP polypeptide was analyzed by a variation of the computer program "PSORT", available from Dr. Kenta Nakai of the Institute for Chemical Research, Kyoto University (Nakai, K. and Kanehisa, M. *Genomics* 14:897–911 (1992)), which is an expert system for predicting the cellular location of a protein based on the amino acid sequence. As part of this computational prediction of localization, the methods of McGeoch and von Heinje are incorporated. Thus, the computation analysis above predicted a single cleavage site within the complete amino acid sequence shown in SEQ ID NO:2 (see above discussion).

As one of ordinary skill would appreciate from the above discussions, due to the possibilities of sequencing errors as well as the variability of cleavage sites in different known proteins, the mature IL17RLP polypeptide encoded by the deposited cDNA is expected to consist of about 407 amino acids (presumably residues 1 to 407 of SEQ ID NO:2, but may consist of any number of amino acids in the range of about 407–412 amino acids; and the actual leader sequence (s) of this protein is expected to be 14–19 amino acids (presumably residues −19 through −1 of SEQ ID NO:2), but may consist of any number of amino acids in the range of 14–19 amino acids.

In another embodiment, the encoded polypeptide has a predicted leader sequence from Met-(−19) to Ser-(−6) of SEQ ID NO:2 (i.e., from Met-1 to Ser-14 of the amino acid sequence presented in FIGS. 1A, 1B, and 1C); an extracellular domain from Ala-(−5) to Trp-271 of SEQ ID NO:2 (i.e., from Ala-15 to Trp-290 of the amino acid sequence presented in FIGS. 1A, 1B, and 1C); a transmembrane domain from Leu-272 to Leu-292 of SEQ ID NO:2 (i.e., from Leu-291 to Leu-311 of the amino acid sequence presented in FIGS. 1A, 1B, and 1C); and an intracellular domain from Met-293 to Leu-407 of SEQ ID NO:2 (i.e., from Met-312 to Leu-426 of the amino acid sequence presented in FIGS. 1A, 1B, and 1C). The predicted leader peptide in this embodiment is within the originally predicted range of 14–19 amino acids.

In an additional embodiment, the IL17RLP transmembrane domain may have an N-terminal boundary beginning at amino acid residue Pro-268, Gly-269, Gly-270, Trp-271 or Leu-272 of the IL17RLP sequence as shown in SEQ ID NO:2 (i.e., amino acid residues Pro-287, Gly-288, Gly-289, Trp-290 or Leu-291 of the IL17RLP sequence as shown in FIGS. 1A, 1B, and 1C) and a C-terminal boundary including amino acid residue Tyr-291, Leu-292, Met-293 or Trp-294 of the IL17RLP sequence as shown in SEQ ID NO:2 (i.e., amino acid residues Tyr-310, Leu-31 1, Met-312 or Trp-313 of the IL17RLP sequence as shown in FIGS. 1A, 1B, and 1C).

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 10–12 of the nucleotide sequence shown in FIGS. 1A, 1B, and 1C (SEQ ID NO:1).

Also included are DNA molecules comprising the coding sequence for the predicted mature IL17RLP protein shown at positions 1–407 of SEQ ID NO:2.

In addition, isolated nucleic acid molecules of the invention include DNA molecules which comprise a sequence substantially different from those described above but which, due to the degeneracy of the genetic code, still encode the IL17RLP protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*).

In another aspect, the invention provides isolated nucleic acid molecules encoding the IL17RLP polypeptide having an amino acid sequence encoded by the cDNA clone contained in the plasmid deposited as ATCC Deposit No. 209198 on Aug. 8, 1997.

Preferably, this nucleic acid molecule will encode the mature polypeptide encoded by the above-described deposited cDNA clone.

The invention further provides an isolated nucleic acid molecule having the nucleotide sequence shown in FIGS. 1A, 1B, and 1C (SEQ ID NO:1) or the nucleotide sequence of the IL17RLP cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the IL17RLP gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 1–1290 of SEQ ID NO:1.

In addition, the invention provides nucleic acid molecules having nucleotide sequences related to extensive portions of SEQ ID NO:1 which have been determined from the following related cDNA clones: HHPCH63R (SEQ ID NO:4) and HETCC45RA (SEQ ID NO:5). Such polynucleotides may preferably be excluded from the invention.

Further, the invention includes a polynucleotide comprising any portion of at least about 30 nucleotides, preferably at least about 50 nucleotides, of SEQ ID NO:1 from residue 50–1800, 100–1800, 200–1800, 300–1800, 400–1800, 500–1800, 600–1800, 50–650, 100–650, 200–650, 300–650, 400–650, 500–650, 50–500, 100–500, 200–500, 300–500, 400–500, 50–400, 100–400, 200–400, 300–400, 50–300, 100–300, 200–300, 50–200, 100–200, and 50–100.

More generally, by a fragment of an isolated nucleic acid molecule having the nucleotide sequence of the deposited cDNA or the nucleotide sequence shown in FIGS. 1A, 1B, and 1C (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIGS. 1A, 1B, and 1C (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A, 1B, and 1C (SEQ ID NO:1). Preferred nucleic acid fragments of the present invention include nucleic acid molecules encoding epitope-bearing portions of the IL17RLP polypeptide as identified in FIG. 3 and described in more detail below.

In specific embodiments, the polynucleotide fragments of the invention encode a polypeptide which demonstrates a functional activity. By a polypeptide demonstrating "functional activity" is meant, a polypeptide capable of displaying one or more known functional activities associated with a complete, mature or active form of the IL17RLP polypeptide. Such functional activities include, but are not limited to, biological activity ((e.g., activation of signal transduction pathways resulting in the stimulation of the NF-kappaB transcription factor family, the secretion of IL-6, and the costimulation of T-cell proliferation; induction of IL-6, IL-8, G-CSF, Prostaglandin E (PGE$_2$), and intracellular adhesion molecule (ICAM)-1 expression; regulation of hematopoietic stem and progenitor cell growth and expansion; myelosuppressive activity for stem and immature subsets of myeloid progenitors; activation and stimulation of hematopoiesis in general (more specifically, neutrophil hematopoiesis); enhancement of erythropoiesis; suppression of lymphopoiesis and myelopoiesis; and strong suppression of monocytopoiesis)), antigenicity [ability to bind (or compete with a IL17RLP polypeptide for binding) to an anti-IL17RLP antibody], immunogenicity (ability to generate antibody which binds to an IL17RLP polypeptide), the ability to form polymers with other IL17RLP or IL17RLP-like polypeptides, and ability to bind to a receptor or ligand for an IL17RLP polypeptide.

Preferred nucleic acid fragments of the present invention also include nucleic acid molecules encoding one or more of the following domains of IL17RLP: Domain I (i.e., Val-49 through Leu-62 of SEQ ID NO:2 (Val-68 through Leu-81 of FIGS. 1A, 1B, and 1C)); Domain II (Cys-154 through Thr-166 of SEQ ID NO:2 (i.e., Cys-173 through Thr-185 of FIGS. 1A, 1B, and 1C)); Domain III (Gln-202 through Gln-208 of SEQ ID NO:2 (i.e., Gln-221 through Gln-227 of FIGS. 1A, 1B, and 1C)); Domain IV (Asp-241 through Val-249 of SEQ ID NO:2 (i.e., Asp-260 through Val-268 of FIGS. 1A, 1B, and 1C)); Domain V (Thr-255 through Leu-261 of SEQ ID NO:2 (i.e., Thr-274 through Leu-280 of FIGS. 1A, 1B, and 1C)); Domain VI (Leu-310 through Tyr-319 of SEQ ID NO:2 (i.e., Leu-329 through Tyr-338 of FIGS. 1A, 1B, and 1C)); Domain VII (Cys-340 through Leu-346 of SEQ ID NO:2 (i.e., Cys-359 through Leu-365 of FIGS. 1A, 1B, and 1C)); and Domain VIII (Ile-354 through Gly-358 of SEQ ID NO:2 (i.e., Ile-373 through Gly-377 of FIGS. 1A, 1B, and 1C)).

In specific embodiments, the polynucleotide fragments of the invention encode antigenic regions. Non-limiting examples of antigenic polypeptides or peptides that can be used to generate IL17RLP-specific antibodies include: a polypeptide comprising amino acid residues from about from about Ser-14 to about Val-22, from about Cys-24 to about Pro-32, from about Ile-41 to about Arg-49, from about Thr-89 to about, from about Thr-110 to about Lys-118, from about Ala-144 to about Ser-152, from about Thr-240 to about Val-248, from about Gly-258 to about Thr-267, from about Leu-280 to about Gly-288, from about Cys-404 to about Glu-412, from about Pro-415 to about Ser-423, from about Gly-409 to about Glu-417, and from about Cys-404 to about Leu-426 in FIGS. 1A, 1B, and 1C (which is the identical sequence to that shown in SEQ ID NO:2, with the exception of the numbering schemes as described above).

In additional embodiments, the polynucleotides of the invention encode functional attributes of IL17RLP. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of IL17RLP.

The data representing the structural or functional attributes of IL17RLP set forth in FIG. 3 and/or Table I, as described above, was generated using the various modules and algorithms of the DNA*STAR set on default parameters. In a preferred embodiment, the data presented in columns VIII, IX, XIII, and XIV of Table I can be used to determine regions of IL17RLP which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table I, be represented or identified by using tabular representations of the data presented in FIG. 3. The DNA*STAR computer algorithm used to generate FIG. 3 (set on the original default parameters) was used to present the data in FIG. 3 in a tabular format (See Table I). The tabular format of the data in FIG. 3 may be used to easily determine specific boundaries of a preferred region.

The above-mentioned preferred regions set out in FIG. 3 and in Table I include, but are not limited to, regions of the aforementioned types identified by analysis of the amino acid sequence set out in FIGS. 1A, 1B, and 1C. As set out in FIG. 3 and in Table I, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

TABLE I

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | A | . | . | . | . | . | −1.43 | 0.61 | . | . | . | −0.60 | 0.30 |
| Ser | 2 | A | A | . | . | . | . | . | −1.86 | 0.87 | . | . | . | −0.60 | 0.20 |
| Leu | 3 | A | A | . | . | . | . | . | −1.77 | 1.13 | . | . | . | −0.60 | 0.13 |
| Val | 4 | A | A | . | . | . | . | . | −2.19 | 1.09 | . | . | . | −0.60 | 0.17 |
| Leu | 5 | A | A | . | . | . | . | . | −2.39 | 1.16 | . | . | . | −0.60 | 0.11 |
| Leu | 6 | A | A | . | . | . | . | . | −2.38 | 1.27 | . | . | . | −0.60 | 0.13 |
| Ser | 7 | A | A | . | . | . | . | . | −2.89 | 1.09 | . | . | . | −0.60 | 0.18 |
| Leu | 8 | A | A | . | . | . | . | . | −2.74 | 1.13 | * | * | . | −0.60 | 0.18 |
| Ala | 9 | A | A | . | . | . | . | . | −1.78 | 1.01 | * | * | . | −0.60 | 0.11 |
| Ala | 10 | A | A | . | . | . | . | . | −1.27 | 0.33 | * | * | . | −0.30 | 0.17 |
| Leu | 11 | A | A | . | . | . | . | . | −1.04 | 0.33 | * | * | . | −0.30 | 0.27 |
| Cys | 12 | A | . | B | . | . | T | . | −1.60 | 0.14 | * | . | . | 0.10 | 0.27 |
| Arg | 13 | . | . | B | . | . | T | . | −1.00 | 0.29 | * | . | . | 0.40 | 0.20 |
| Ser | 14 | . | . | B | . | . | T | . | −0.30 | 0.21 | . | . | . | 0.70 | 0.37 |
| Ala | 15 | . | . | B | . | . | T | . | 0.29 | −0.47 | . | . | . | 1.75 | 1.37 |
| Val | 16 | . | . | . | . | . | . | C | 0.89 | −1.04 | * | . | F | 2.50 | 1.21 |
| Pro | 17 | . | . | . | . | T | . | . | 1.24 | −0.61 | * | . | F | 3.00 | 1.39 |
| Arg | 18 | . | . | . | . | T | . | . | 0.28 | −0.51 | . | . | F | 2.70 | 1.99 |
| Glu | 19 | . | . | B | . | . | . | . | 0.58 | −0.37 | . | . | F | 1.70 | 1.99 |
| Pro | 20 | . | . | B | . | . | . | . | 0.50 | −0.61 | . | . | F | 1.70 | 2.23 |
| Thr | 21 | . | . | B | . | . | . | . | 1.01 | −0.47 | . | . | F | 0.95 | 0.61 |
| Val | 22 | . | . | B | . | . | . | . | 0.92 | −0.04 | . | . | . | 0.50 | 0.35 |
| Gln | 23 | . | . | B | . | . | . | . | 0.81 | 0.34 | . | . | . | 0.18 | 0.30 |
| Cys | 24 | . | . | B | . | . | T | . | 0.50 | −0.09 | * | . | F | 1.41 | 0.36 |
| Gly | 25 | . | . | B | . | . | T | . | 0.37 | −0.09 | * | . | F | 1.69 | 0.71 |
| Ser | 26 | . | . | . | . | T | T | . | 0.47 | −0.30 | * | . | F | 2.37 | 0.40 |
| Glu | 27 | . | . | . | . | T | T | . | 1.02 | −0.27 | * | . | F | 2.80 | 1.16 |
| Thr | 28 | . | . | . | . | . | . | C | 0.81 | −0.46 | * | . | F | 2.12 | 1.57 |
| Gly | 29 | . | . | . | . | . | . | C | 1.48 | −0.46 | . | . | F | 1.84 | 1.82 |
| Pro | 30 | . | . | . | . | . | . | C | 1.53 | −0.84 | . | . | F | 1.86 | 1.82 |
| Ser | 31 | . | . | . | . | . | T | C | 1.23 | 0.07 | . | . | F | 0.88 | 1.32 |
| Pro | 32 | . | . | . | . | . | T | C | 0.42 | 0.20 | . | * | F | 0.60 | 1.32 |
| Glu | 33 | A | . | . | . | . | T | . | 0.73 | 0.46 | . | . | F | −0.05 | 0.71 |
| Trp | 34 | A | . | . | . | . | T | . | 1.04 | 0.43 | * | . | . | −0.20 | 0.91 |
| Met | 35 | A | A | . | . | . | . | . | 1.26 | 0.54 | . | * | . | −0.60 | 0.80 |
| Leu | 36 | A | A | . | . | . | . | . | 0.74 | 0.11 | . | * | . | −0.30 | 0.77 |
| Gln | 37 | A | A | . | . | . | . | . | 0.07 | 0.80 | . | * | . | −0.60 | 0.61 |
| His | 38 | . | A | B | . | . | . | . | −0.14 | 0.57 | . | * | . | −0.60 | 0.43 |
| Asp | 39 | . | A | . | . | T | . | . | −0.20 | 0.39 | . | . | . | 0.10 | 0.81 |
| Leu | 40 | . | A | . | . | . | . | C | 0.40 | 0.13 | . | . | . | 0.24 | 0.46 |
| Ile | 41 | . | . | B | . | . | T | . | 0.40 | −0.27 | * | * | . | 1.38 | 0.57 |
| Pro | 42 | . | . | B | . | . | T | . | 0.51 | −0.09 | * | * | F | 1.87 | 0.28 |
| Gly | 43 | . | . | . | . | T | T | . | 0.54 | −0.09 | * | * | F | 2.61 | 0.66 |
| Asp | 44 | . | . | . | . | T | T | . | −0.27 | −0.77 | * | . | F | 3.40 | 1.58 |
| Leu | 45 | . | A | B | . | . | . | . | 0.66 | −0.77 | * | * | F | 2.11 | 0.84 |
| Arg | 46 | . | A | B | . | . | . | . | 0.69 | −1.20 | * | * | F | 1.92 | 1.67 |
| Asp | 47 | . | A | B | . | . | . | . | 0.90 | −0.99 | * | * | F | 1.43 | 0.74 |
| Leu | 48 | . | A | B | . | . | . | . | 1.03 | −0.99 | . | . | . | 1.09 | 1.56 |
| Arg | 49 | . | A | B | . | . | . | . | 0.18 | −1.24 | . | . | . | 0.75 | 1.23 |
| Val | 50 | . | A | B | B | . | . | . | 0.68 | −0.60 | * | . | . | 0.60 | 0.55 |
| Glu | 51 | . | A | B | B | . | . | . | 0.26 | −0.11 | * | . | F | 0.45 | 0.96 |
| Pro | 52 | . | A | B | B | . | . | . | −0.04 | −0.31 | * | * | F | 0.45 | 0.70 |
| Val | 53 | . | . | B | B | . | . | . | −0.09 | 0.07 | * | * | F | 0.00 | 1.27 |
| Thr | 54 | . | . | B | B | . | . | . | −0.79 | 0.07 | * | * | F | −0.15 | 0.55 |
| Thr | 55 | . | . | B | B | . | . | . | −0.24 | 0.57 | * | . | F | −0.45 | 0.36 |
| Ser | 56 | . | . | B | B | . | . | . | −0.59 | 0.63 | * | . | F | −0.45 | 0.69 |
| Val | 57 | . | . | B | B | . | . | . | −0.38 | 0.41 | . | . | F | −0.45 | 0.47 |
| Ala | 58 | . | . | B | B | . | . | . | 0.23 | −0.07 | . | . | F | 0.45 | 0.55 |
| Thr | 59 | . | . | B | . | . | T | . | 0.24 | 0.20 | . | * | F | 0.25 | 0.64 |
| Gly | 60 | . | . | B | . | . | T | . | −0.33 | 0.20 | . | . | F | 0.40 | 1.16 |
| Asp | 61 | . | . | B | . | . | T | . | −0.84 | 0.24 | . | . | F | 0.25 | 0.80 |
| Tyr | 62 | . | . | B | . | . | T | . | −0.59 | 0.43 | . | * | . | −0.20 | 0.46 |
| Ser | 63 | . | . | B | B | . | . | . | −0.00 | 0.56 | . | * | . | −0.60 | 0.46 |
| Ile | 64 | . | . | B | B | . | . | . | −0.54 | 0.53 | . | * | . | −0.60 | 0.44 |
| Leu | 65 | . | . | B | B | . | . | . | −0.50 | 1.17 | . | * | . | −0.60 | 0.21 |
| Met | 66 | . | . | B | B | . | . | . | −0.79 | 0.80 | . | * | . | −0.60 | 0.21 |
| Asn | 67 | . | . | B | B | . | . | . | −1.40 | 1.33 | . | * | . | −0.60 | 0.31 |
| Val | 68 | . | . | B | B | . | . | . | −1.91 | 1.29 | * | * | . | −0.60 | 0.28 |
| Ser | 69 | . | . | B | B | . | . | . | −0.91 | 1.29 | * | * | . | −0.60 | 0.24 |
| Trp | 70 | . | . | B | B | . | . | . | −0.69 | 0.67 | * | * | . | −0.60 | 0.29 |
| Val | 71 | . | . | B | B | . | . | . | −0.09 | 0.77 | . | * | . | −0.60 | 0.39 |
| Leu | 72 | . | A | . | B | . | . | . | −0.68 | 0.13 | . | * | . | −0.30 | 0.49 |
| Arg | 73 | . | A | . | B | . | . | . | −0.12 | 0.24 | * | * | . | −0.30 | 0.47 |
| Ala | 74 | . | A | . | B | . | . | . | −0.71 | −0.29 | * | * | . | 0.30 | 0.85 |
| Asp | 75 | . | A | . | B | . | . | . | −0.31 | −0.24 | * | . | . | 0.30 | 0.72 |
| Ala | 76 | . | A | . | B | . | . | . | −0.27 | −0.93 | * | * | . | 0.60 | 0.72 |
| Ser | 77 | . | A | . | B | . | . | . | −0.27 | −0.24 | * | * | . | 0.30 | 0.59 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Ile | 78 | A | . | . | B | . | . | . | −0.33 | −0.06 | * | * | . | 0.30 | 0.29 |
| Arg | 79 | A | . | . | B | . | . | . | −0.33 | −0.06 | * | * | . | 0.30 | 0.57 |
| Leu | 80 | A | . | . | B | . | . | . | −0.64 | −0.06 | * | * | . | 0.30 | 0.43 |
| Leu | 81 | A | . | . | B | . | . | . | −0.01 | 0.04 | * | * | . | −0.30 | 0.89 |
| Lys | 82 | A | . | . | B | . | . | . | −0.60 | −0.64 | * | * | F | 0.75 | 0.91 |
| Ala | 83 | A | . | . | B | . | . | . | −0.38 | 0.04 | * | * | F | −0.15 | 0.77 |
| Thr | 84 | A | . | . | B | . | . | . | −1.34 | −0.07 | * | . | F | 0.45 | 0.50 |
| Lys | 85 | . | . | B | B | . | . | . | −0.84 | −0.11 | * | . | F | 0.45 | 0.19 |
| Ile | 86 | . | . | B | B | . | . | . | −0.38 | 0.37 | . | * | . | −0.30 | 0.27 |
| Cys | 87 | . | . | B | B | . | . | . | −0.38 | 0.30 | * | * | . | −0.30 | 0.18 |
| Val | 88 | . | . | B | B | . | . | . | −0.09 | −0.19 | * | * | . | 0.58 | 0.18 |
| Thr | 89 | . | . | B | B | . | . | . | 0.22 | 0.20 | * | * | F | 0.41 | 0.35 |
| Gly | 90 | . | . | . | . | . | T | T | . | −0.52 | −0.09 | * | * | F | 2.24 | 1.05 |
| Lys | 91 | . | . | . | . | . | T | T | . | 0.37 | 0.13 | * | * | F | 1.92 | 1.22 |
| Ser | 92 | . | . | . | . | . | T | T | . | 0.73 | −0.11 | . | * | F | 2.80 | 1.47 |
| Asn | 93 | . | . | . | . | . | T | T | . | 1.34 | −0.21 | * | * | F | 2.52 | 1.99 |
| Phe | 94 | . | . | . | . | . | T | . | . | 1.36 | 0.11 | * | * | F | 1.44 | 1.56 |
| Gln | 95 | . | . | . | . | . | T | . | . | 1.03 | 0.50 | * | * | F | 0.86 | 1.56 |
| Ser | 96 | . | . | . | . | . | T | T | . | 0.13 | 0.69 | * | * | . | 0.48 | 0.52 |
| Tyr | 97 | . | . | . | B | . | . | T | . | 0.54 | 0.93 | . | * | . | −0.20 | 0.44 |
| Ser | 98 | . | . | . | . | . | T | T | . | −0.12 | 0.14 | . | * | . | 0.50 | 0.50 |
| Cys | 99 | . | . | . | B | . | . | T | . | 0.58 | 0.31 | . | * | . | 0.10 | 0.20 |
| Val | 100 | . | . | . | B | . | . | . | . | 0.33 | 0.33 | . | * | . | 0.12 | 0.21 |
| Arg | 101 | . | . | . | B | . | . | . | . | 0.32 | 0.33 | . | * | . | 0.34 | 0.24 |
| Cys | 102 | . | . | . | B | . | . | T | . | 0.57 | 0.43 | * | * | . | 0.46 | 0.65 |
| Asn | 103 | . | . | . | . | . | T | T | . | 0.28 | −0.14 | * | * | . | 2.13 | 1.52 |
| Tyr | 104 | . | . | . | . | . | T | T | . | 0.24 | −0.29 | * | * | . | 2.20 | 0.78 |
| Thr | 105 | . | . | . | . | . | . | T | C | 1.10 | 0.50 | * | * | . | 1.03 | 1.26 |
| Glu | 106 | . | . | A | B | B | . | . | . | 0.68 | 0.33 | . | * | . | 0.51 | 1.36 |
| Ala | 107 | . | . | A | B | B | . | . | . | 1.34 | 0.41 | . | . | . | −0.01 | 1.25 |
| Phe | 108 | . | . | A | B | B | . | . | . | 1.03 | 0.06 | * | * | F | 0.22 | 1.50 |
| Gln | 109 | . | . | A | B | B | . | . | . | 1.39 | 0.06 | * | * | F | 0.00 | 1.25 |
| Thr | 110 | . | . | A | B | B | . | . | . | 1.49 | 0.06 | * | * | F | 0.00 | 2.43 |
| Gln | 111 | . | . | . | B | B | . | . | . | 1.19 | −0.01 | * | * | F | 0.94 | 4.34 |
| Thr | 112 | . | . | . | . | B | . | . | C | 1.43 | −0.41 | * | * | F | 1.48 | 3.36 |
| Arg | 113 | . | . | . | . | B | . | . | C | 1.79 | −0.39 | . | * | F | 1.82 | 2.30 |
| Pro | 114 | . | . | . | . | . | T | T | . | 1.83 | −0.44 | . | * | F | 2.76 | 1.32 |
| Ser | 115 | . | . | . | . | . | T | T | . | 1.86 | −0.84 | . | * | F | 3.40 | 1.82 |
| Gly | 116 | . | . | . | . | . | T | T | . | 1.54 | −0.41 | . | * | F | 2.61 | 0.98 |
| Gly | 117 | . | . | . | . | . | T | T | . | 1.16 | 0.07 | . | * | F | 1.67 | 0.91 |
| Lys | 118 | . | . | . | B | T | . | . | . | 0.74 | 0.43 | . | * | F | 0.63 | 0.59 |
| Trp | 119 | . | . | B | B | . | . | . | . | 0.71 | 0.43 | * | . | . | −0.26 | 0.80 |
| Thr | 120 | . | . | B | B | . | . | . | . | 0.12 | 0.76 | . | * | . | −0.45 | 1.26 |
| Phe | 121 | . | . | B | B | . | . | . | . | 0.12 | 1.01 | . | * | . | −0.60 | 0.44 |
| Ser | 122 | . | . | B | B | . | . | . | . | −0.23 | 1.44 | . | * | . | −0.60 | 0.42 |
| Tyr | 123 | . | . | B | B | . | . | . | . | −0.49 | 1.31 | . | * | . | −0.60 | 0.25 |
| Ile | 124 | . | . | . | B | T | . | . | . | −1.06 | 1.26 | . | * | . | −0.20 | 0.45 |
| Gly | 125 | . | . | . | . | B | . | . | C | −0.74 | 1.11 | . | * | . | −0.40 | 0.25 |
| Phe | 126 | . | . | . | . | B | . | . | C | −0.86 | 0.73 | . | * | . | −0.40 | 0.27 |
| Pro | 127 | . | . | B | . | . | . | . | . | −0.56 | 0.66 | . | * | . | −0.40 | 0.32 |
| Val | 128 | . | . | B | . | . | . | . | . | −0.62 | 0.37 | . | * | . | −0.10 | 0.52 |
| Glu | 129 | . | . | B | . | . | . | . | . | −0.59 | 0.43 | . | * | . | −0.40 | 0.87 |
| Leu | 130 | . | . | B | B | . | . | . | . | −0.49 | 0.29 | . | * | . | −0.30 | 0.42 |
| Asn | 131 | . | . | B | B | . | . | . | . | −0.49 | 0.61 | . | * | . | −0.60 | 0.88 |
| Thr | 132 | . | . | B | B | . | . | . | . | −1.17 | 0.76 | . | . | . | −0.60 | 0.44 |
| Val | 133 | . | . | B | B | . | . | . | . | −0.66 | 1.44 | . | . | . | −0.60 | 0.38 |
| Tyr | 134 | . | . | B | B | . | . | . | . | −1.24 | 1.19 | . | . | . | −0.60 | 0.23 |
| Phe | 135 | . | . | B | B | . | . | . | . | −0.47 | 1.29 | . | . | . | −0.60 | 0.16 |
| Ile | 136 | . | . | B | B | . | . | . | . | −0.47 | 1.30 | . | . | . | −0.60 | 0.30 |
| Gly | 137 | . | . | B | . | . | . | . | . | −1.04 | 1.06 | . | . | . | −0.40 | 0.30 |
| Ala | 138 | . | . | B | . | . | . | . | . | −0.40 | 0.99 | . | . | . | −0.40 | 0.25 |
| His | 139 | . | . | . | . | . | . | . | C | −0.16 | 0.63 | * | . | . | −0.20 | 0.54 |
| Asn | 140 | . | . | . | . | . | . | . | C | −0.04 | 0.34 | . | . | . | 0.10 | 0.88 |
| Ile | 141 | . | . | . | . | . | . | T | C | 0.84 | 0.41 | . | . | . | 0.00 | 0.88 |
| Pro | 142 | . | . | . | . | . | . | T | C | 0.59 | 0.31 | * | . | F | 0.60 | 1.04 |
| Asn | 143 | . | . | . | . | . | T | T | . | 1.18 | 0.43 | * | . | F | 0.35 | 0.64 |
| Ala | 144 | . | . | . | . | . | T | T | C | 1.21 | 0.43 | . | . | F | 0.64 | 1.47 |
| Asn | 145 | . | . | . | . | . | . | . | C | 1.21 | −0.26 | . | * | . | 1.53 | 1.65 |
| Met | 146 | . | . | B | . | . | . | . | . | 1.76 | −0.69 | . | * | . | 1.97 | 1.71 |
| Asn | 147 | . | . | . | . | . | . | T | C | 1.76 | −0.66 | . | * | F | 2.86 | 1.68 |
| Glu | 148 | . | . | . | . | . | T | T | . | 1.46 | −0.73 | . | * | F | 3.40 | 1.61 |
| Asp | 149 | . | . | . | . | . | T | T | . | 1.44 | −0.74 | . | . | F | 3.06 | 2.19 |
| Gly | 150 | . | . | . | . | . | . | T | C | 1.14 | −0.74 | . | . | F | 2.52 | 1.35 |
| Pro | 151 | . | . | . | . | . | . | . | C | 0.89 | −0.76 | . | . | F | 1.98 | 1.04 |
| Ser | 152 | . | . | . | B | . | . | . | C | 0.89 | −0.11 | . | * | F | 0.99 | 0.46 |
| Met | 153 | . | . | B | B | . | . | . | . | 0.19 | 0.29 | * | * | . | −0.30 | 0.75 |
| Ser | 154 | . | . | B | B | . | . | . | . | −0.12 | 0.64 | . | * | . | −0.60 | 0.42 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Val | 155 | . | . | B | B | . | . | . | −0.08 | 0.70 | . | * | . | −0.60 | 0.45 |
| Asn | 156 | . | . | B | B | . | . | . | −0.08 | 0.70 | . | * | . | −0.60 | 0.61 |
| Phe | 157 | . | . | B | B | . | . | . | −0.12 | 0.51 | . | * | . | −0.60 | 0.71 |
| Thr | 158 | . | . | . | B | T | . | . | −0.19 | 0.56 | . | * | F | −0.05 | 0.94 |
| Ser | 159 | . | . | . | . | . | . | C | −0.70 | 0.49 | . | * | F | 0.15 | 0.31 |
| Pro | 160 | . | . | . | . | . | T | T | 0.16 | 0.77 | . | * | F | 0.35 | 0.30 |
| Gly | 161 | . | . | . | . | . | T | T | 0.12 | −0.01 | . | . | F | 1.25 | 0.35 |
| Cys | 162 | A | . | . | . | . | . | T | . | −0.07 | −0.00 | . | . | . | 0.70 | 0.35 |
| Leu | 163 | A | A | . | . | . | . | . | −0.36 | 0.30 | * | . | . | −0.30 | 0.16 |
| Asp | 164 | A | A | . | . | . | . | . | −0.01 | 0.49 | * | . | . | −0.60 | 0.16 |
| His | 165 | A | A | . | . | . | . | . | −0.04 | 0.06 | * | * | . | −0.30 | 0.60 |
| Ile | 166 | A | A | . | . | . | . | . | 0.34 | 0.24 | * | . | . | −0.15 | 1.13 |
| Met | 167 | A | A | . | . | . | . | . | 1.06 | −0.44 | * | * | . | 0.45 | 1.36 |
| Lys | 168 | A | A | . | . | . | . | . | 1.91 | −0.44 | * | * | . | 0.45 | 1.99 |
| Tyr | 169 | A | A | . | . | . | . | . | 1.24 | −0.94 | * | . | F | 0.90 | 5.69 |
| Lys | 170 | A | A | . | . | . | . | . | 0.42 | −1.06 | * | . | F | 0.90 | 3.08 |
| Lys | 171 | A | A | . | . | . | . | . | 1.36 | −1.03 | * | * | F | 0.90 | 1.14 |
| Lys | 172 | A | A | . | . | . | . | . | 1.37 | −1.03 | * | * | F | 0.90 | 1.46 |
| Cys | 173 | . | A | B | . | . | . | . | 0.98 | −1.29 | * | . | . | 0.60 | 0.74 |
| Val | 174 | . | A | B | . | . | . | . | 0.92 | −0.86 | * | . | . | 0.60 | 0.36 |
| Lys | 175 | . | A | B | . | . | . | . | 0.07 | −0.47 | * | . | F | 0.45 | 0.24 |
| Ala | 176 | . | A | B | . | . | . | . | −0.27 | 0.21 | * | . | F | 0.01 | 0.38 |
| Gly | 177 | . | . | B | . | . | . | T | . | −0.31 | 0.56 | * | . | F | 0.27 | 0.53 |
| Ser | 178 | . | . | . | . | . | T | C | 0.14 | −0.09 | . | * | F | 1.53 | 0.44 |
| Leu | 179 | . | . | . | . | T | T | . | 1.00 | 0.34 | * | * | F | 1.29 | 0.68 |
| Trp | 180 | . | . | . | . | T | T | . | 0.07 | 0.24 | * | * | F | 1.60 | 1.11 |
| Asp | 181 | . | . | . | . | . | T | C | 0.34 | 0.50 | * | * | F | 0.79 | 0.58 |
| Pro | 182 | . | . | . | . | T | T | . | 0.10 | 0.60 | . | * | F | 0.98 | 1.01 |
| Asn | 183 | . | . | . | . | T | T | . | −0.27 | 0.41 | * | . | F | 0.67 | 0.97 |
| Ile | 184 | A | . | . | . | . | . | T | . | 0.59 | 0.07 | * | * | . | 0.26 | 0.31 |
| Thr | 185 | A | . | . | . | . | . | . | 0.92 | 0.07 | * | * | . | −0.10 | 0.40 |
| Ala | 186 | A | . | . | . | . | . | . | 0.92 | −0.36 | . | * | . | 0.50 | 0.50 |
| Cys | 187 | A | . | . | . | . | . | T | . | 1.13 | −0.36 | . | . | . | 0.85 | 1.15 |
| Lys | 188 | A | . | . | . | . | . | T | . | 1.13 | −1.04 | . | . | F | 1.30 | 1.38 |
| Lys | 189 | A | . | . | . | . | . | T | . | 1.71 | −1.53 | * | . | F | 1.30 | 2.37 |
| Asn | 190 | A | . | . | . | . | . | T | . | 1.17 | −1.54 | * | . | F | 1.30 | 6.38 |
| Glu | 191 | A | . | . | . | . | . | . | 1.76 | −1.47 | . | . | F | 1.10 | 2.37 |
| Glu | 192 | A | . | . | . | . | . | . | 1.57 | −1.47 | . | * | F | 1.10 | 2.05 |
| Thr | 193 | A | . | . | B | . | . | . | 1.52 | −0.83 | * | * | F | 0.75 | 0.95 |
| Val | 194 | A | . | . | B | . | . | . | 0.78 | −0.83 | . | * | F | 0.75 | 0.88 |
| Glu | 195 | A | . | . | B | . | . | . | 0.47 | −0.04 | . | * | . | 0.30 | 0.44 |
| Val | 196 | A | . | . | B | . | . | . | 0.16 | 0.44 | . | * | . | −0.60 | 0.44 |
| Asn | 197 | . | . | B | B | . | . | . | −0.16 | 0.44 | . | * | . | −0.60 | 0.85 |
| Phe | 198 | . | . | B | B | . | . | . | −0.06 | 0.29 | . | * | . | −0.30 | 0.71 |
| Thr | 199 | . | . | B | B | . | . | . | −0.01 | 0.71 | . | * | F | −0.30 | 1.48 |
| Thr | 200 | . | . | B | B | . | . | . | −0.36 | 0.76 | . | * | F | −0.33 | 0.76 |
| Thr | 201 | . | . | . | . | . | T | C | 0.50 | 0.79 | . | * | F | 0.39 | 0.87 |
| Pro | 202 | . | . | . | . | . | T | C | 0.61 | 0.40 | . | . | F | 0.81 | 0.97 |
| Leu | 203 | . | . | . | . | T | T | . | 1.07 | −0.09 | * | . | F | 1.88 | 1.32 |
| Gly | 204 | . | . | . | . | . | T | C | 0.78 | 0.19 | * | . | F | 1.20 | 1.43 |
| Asn | 205 | . | . | . | . | . | T | C | 0.50 | 0.31 | * | . | F | 0.93 | 0.91 |
| Arg | 206 | . | . | B | . | . | T | . | 0.00 | 0.39 | * | . | . | 0.61 | 1.12 |
| Tyr | 207 | . | . | B | . | . | T | . | −0.68 | 0.39 | * | * | . | 0.34 | 0.93 |
| Met | 208 | . | . | B | . | . | T | . | 0.13 | 0.64 | * | . | . | −0.08 | 0.41 |
| Ala | 209 | . | . | B | B | . | . | . | 0.44 | 0.64 | * | . | . | −0.60 | 0.36 |
| Leu | 210 | . | . | B | B | . | . | . | 0.14 | 1.14 | * | . | . | −0.60 | 0.31 |
| Ile | 211 | . | . | B | B | . | . | . | −0.28 | 0.77 | * | * | . | −0.60 | 0.42 |
| Gln | 212 | . | . | B | B | . | . | . | −0.92 | 0.64 | . | . | . | −0.60 | 0.60 |
| His | 213 | . | . | B | B | . | . | . | −1.21 | 0.83 | . | . | . | −0.60 | 0.51 |
| Ser | 214 | . | . | B | B | . | . | . | −0.97 | 0.83 | . | . | . | −0.60 | 0.51 |
| Thr | 215 | . | . | B | B | . | . | . | −0.86 | 0.57 | . | . | . | −0.60 | 0.29 |
| Ile | 216 | . | . | B | B | . | . | . | −0.27 | 0.96 | . | . | . | −0.60 | 0.19 |
| Ile | 217 | . | . | B | B | . | . | . | −0.27 | 0.84 | . | . | . | −0.60 | 0.19 |
| Gly | 218 | . | . | B | B | . | . | . | −1.09 | 0.86 | * | . | . | −0.60 | 0.22 |
| Phe | 219 | . | . | B | B | . | . | . | −1.49 | 1.01 | * | . | . | −0.60 | 0.24 |
| Ser | 220 | . | . | . | B | . | . | C | −1.18 | 1.11 | * | . | . | −0.40 | 0.29 |
| Gln | 221 | . | . | B | B | . | . | . | −0.50 | 0.43 | * | . | . | −0.60 | 0.51 |
| Val | 222 | . | . | B | B | . | . | . | 0.36 | 0.43 | * | . | . | −0.60 | 0.92 |
| Phe | 223 | A | . | . | B | . | . | . | 0.70 | 0.14 | * | . | . | −0.30 | 0.93 |
| Glu | 224 | A | . | . | B | . | . | . | 1.44 | 0.16 | * | . | F | −0.15 | 0.93 |
| Pro | 225 | A | A | . | . | . | . | . | 1.79 | −0.24 | * | . | F | 0.60 | 2.51 |
| His | 226 | A | A | . | . | . | . | . | 1.79 | −0.89 | * | . | F | 0.90 | 5.79 |
| Gln | 227 | A | A | . | . | . | . | . | 2.33 | −1.27 | * | * | F | 0.90 | 5.79 |
| Lys | 228 | A | A | . | . | . | . | . | 3.14 | −0.79 | * | * | F | 0.90 | 5.40 |
| Lys | 229 | A | A | . | B | . | . | . | 2.56 | −1.21 | * | * | F | 0.90 | 7.77 |
| Gln | 230 | A | A | . | B | . | . | . | 2.47 | −1.21 | . | * | F | 0.90 | 4.53 |
| Thr | 231 | . | A | B | B | . | . | . | 1.64 | −1.23 | . | . | F | 0.90 | 3.04 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Arg | 232 | . | A | B | B | . | . | . | 0.79 | −0.59 | * | * | F | 0.90 | 1.13 |
| Ala | 233 | . | A | B | B | . | . | . | −0.14 | 0.06 | * | * | F | −0.15 | 0.48 |
| Ser | 234 | . | . | B | B | . | . | . | −0.40 | 0.34 | . | * | . | −0.30 | 0.23 |
| Val | 235 | . | . | B | B | . | . | . | −1.26 | 0.29 | . | * | . | −0.30 | 0.19 |
| Val | 236 | . | . | B | B | . | . | . | −1.26 | 0.93 | . | * | . | −0.60 | 0.14 |
| Ile | 237 | . | . | B | B | . | . | . | −1.71 | 0.91 | * | * | . | −0.60 | 0.15 |
| Pro | 238 | . | . | B | B | . | . | . | −1.12 | 0.96 | . | * | . | −0.60 | 0.20 |
| Val | 239 | . | . | B | B | . | . | . | −1.12 | 0.31 | . | * | . | −0.30 | 0.44 |
| Thr | 240 | . | . | B | B | . | . | . | −0.27 | 0.06 | . | * | F | 0.15 | 0.84 |
| Gly | 241 | . | . | . | B | . | . | C | 0.24 | −0.63 | . | * | F | 1.55 | 0.94 |
| Asp | 242 | . | . | . | . | . | T | C | 0.54 | −0.63 | . | * | F | 2.40 | 1.26 |
| Ser | 243 | . | . | . | . | . | T | C | 0.44 | −0.77 | . | * | F | 2.55 | 0.88 |
| Glu | 244 | . | . | . | . | . | T | C | 0.44 | −0.77 | . | * | F | 3.00 | 1.28 |
| Gly | 245 | . | . | B | . | . | T | . | 0.76 | −0.56 | . | * | F | 2.35 | 0.57 |
| Ala | 246 | . | . | B | B | . | . | . | 0.29 | −0.16 | . | * | F | 1.35 | 0.74 |
| Thr | 247 | . | . | B | B | . | . | . | −0.02 | 0.14 | . | * | . | 0.30 | 0.35 |
| Val | 248 | . | . | B | B | . | . | . | 0.07 | 0.63 | . | . | . | −0.30 | 0.51 |
| Gln | 249 | . | . | B | B | . | . | . | −0.18 | 0.63 | . | * | . | −0.60 | 0.78 |
| Leu | 250 | . | . | B | B | . | . | . | −0.53 | 0.89 | . | * | . | −0.60 | 0.85 |
| Thr | 251 | . | . | B | B | . | . | . | −0.16 | 1.19 | . | * | . | −0.60 | 0.99 |
| Pro | 252 | . | . | B | B | . | . | . | −0.16 | 0.97 | . | * | F | −0.45 | 0.89 |
| Tyr | 253 | . | . | . | B | T | . | . | 0.03 | 1.06 | * | * | F | 0.10 | 1.55 |
| Phe | 254 | . | . | B | . | . | T | . | −0.31 | 0.94 | * | . | . | −0.20 | 0.58 |
| Pro | 255 | . | . | . | . | T | T | . | 0.20 | 0.89 | * | . | F | 0.35 | 0.37 |
| Thr | 256 | . | . | . | . | T | T | . | 0.51 | 0.84 | * | . | F | 0.35 | 0.31 |
| Cys | 257 | . | . | . | . | T | T | . | 0.06 | 0.09 | * | . | F | 0.65 | 0.61 |
| Gly | 258 | . | . | . | . | T | T | . | −0.59 | −0.13 | * | * | F | 1.25 | 0.21 |
| Ser | 259 | . | . | . | . | T | T | . | 0.22 | 0.13 | * | . | F | 0.65 | 0.10 |
| Asp | 260 | . | . | B | . | . | T | . | 0.40 | −0.36 | * | * | F | 0.85 | 0.37 |
| Cys | 261 | . | . | B | . | . | T | . | 0.76 | −0.43 | * | * | . | 0.98 | 0.51 |
| Ile | 262 | . | . | B | . | . | . | . | 1.08 | −0.86 | * | * | . | 1.36 | 0.77 |
| Arg | 263 | . | . | B | . | . | . | . | 1.11 | −0.81 | * | * | . | 1.64 | 0.45 |
| His | 264 | . | . | . | . | T | T | . | 0.56 | −0.33 | * | * | . | 2.37 | 1.22 |
| Lys | 265 | . | . | . | . | T | T | . | −0.30 | −0.26 | * | * | F | 2.80 | 1.30 |
| Gly | 266 | . | . | . | . | T | T | . | −0.44 | −0.30 | * | * | F | 2.37 | 0.49 |
| Thr | 267 | . | . | B | . | . | T | . | −0.22 | 0.39 | * | * | F | 1.09 | 0.30 |
| Val | 268 | . | . | B | B | . | . | . | −0.54 | 0.46 | . | * | . | −0.04 | 0.08 |
| Val | 269 | . | . | B | B | . | . | . | −0.51 | 0.89 | . | * | . | −0.32 | 0.12 |
| Leu | 270 | . | . | B | B | . | . | . | −0.87 | 0.86 | . | * | . | −0.60 | 0.15 |
| Cys | 271 | . | . | B | . | . | T | . | −0.87 | 0.86 | . | . | . | −0.20 | 0.29 |
| Pro | 272 | . | . | B | . | . | T | . | −1.41 | 0.64 | . | . | F | −0.05 | 0.39 |
| Gln | 273 | . | . | . | . | T | T | . | −0.77 | 0.64 | . | . | F | 0.35 | 0.35 |
| Thr | 274 | . | . | . | . | T | T | . | −0.61 | 0.39 | . | . | F | 0.80 | 1.01 |
| Gly | 275 | . | . | B | . | . | . | . | −0.01 | 0.60 | . | * | F | −0.25 | 0.56 |
| Val | 276 | . | . | B | . | . | T | . | −0.16 | 0.60 | . | * | . | −0.20 | 0.50 |
| Pro | 277 | . | . | B | . | . | T | . | 0.06 | 0.89 | . | * | . | −0.20 | 0.29 |
| Phe | 278 | . | . | B | . | . | T | . | 0.06 | 0.40 | . | * | . | 0.14 | 0.49 |
| Pro | 279 | . | . | B | . | . | T | . | 0.37 | 0.37 | . | . | . | 0.93 | 1.05 |
| Leu | 280 | . | . | B | . | . | . | . | 0.76 | 0.13 | . | . | F | 1.22 | 1.09 |
| Asp | 281 | . | . | . | . | T | T | . | 1.31 | −0.30 | . | * | F | 2.76 | 2.52 |
| Asn | 282 | . | . | . | . | T | T | . | 1.57 | −0.70 | . | . | F | 3.40 | 2.19 |
| Asn | 283 | . | . | . | . | T | T | . | 2.06 | −1.13 | . | . | F | 3.06 | 5.31 |
| Lys | 284 | . | . | . | . | T | T | . | 1.92 | −1.39 | . | . | F | 2.85 | 4.91 |
| Ser | 285 | . | . | . | . | . | . | C | 2.39 | −0.96 | . | . | F | 2.24 | 3.02 |
| Lys | 286 | . | . | . | . | . | . | C | 2.10 | −0.93 | . | . | F | 2.23 | 1.86 |
| Pro | 287 | . | . | . | . | T | T | . | 1.29 | −0.41 | . | . | F | 1.77 | 0.98 |
| Gly | 288 | . | . | . | . | T | T | . | 1.08 | 0.27 | . | . | F | 1.30 | 0.60 |
| Gly | 289 | . | . | . | . | T | T | . | 0.22 | 0.31 | . | * | F | 1.17 | 0.47 |
| Trp | 290 | . | . | B | B | . | . | . | −0.29 | 1.00 | * | . | . | −0.21 | 0.25 |
| Leu | 291 | . | . | B | B | . | . | . | −1.14 | 1.26 | . | . | . | −0.34 | 0.21 |
| Pro | 292 | . | . | B | B | . | . | . | −1.74 | 1.51 | . | . | . | −0.47 | 0.17 |
| Leu | 293 | . | . | B | B | . | . | . | −1.70 | 1.77 | . | . | . | −0.60 | 0.14 |
| Leu | 294 | . | . | B | B | . | . | . | −2.17 | 1.24 | . | . | . | −0.60 | 0.22 |
| Leu | 295 | . | . | B | B | . | . | . | −2.69 | 1.24 | . | . | . | −0.60 | 0.12 |
| Leu | 296 | . | . | B | B | . | . | . | −2.73 | 1.50 | . | . | . | −0.60 | 0.12 |
| Ser | 297 | . | . | B | B | . | . | . | −3.11 | 1.46 | . | . | . | −0.60 | 0.11 |
| Leu | 298 | . | . | B | B | . | . | . | −2.61 | 1.27 | . | . | . | −0.60 | 0.13 |
| Leu | 299 | A | . | . | B | . | . | . | −2.09 | 1.07 | . | . | . | −0.60 | 0.23 |
| Val | 300 | A | . | . | B | . | . | . | −2.13 | 1.30 | . | . | . | −0.60 | 0.18 |
| Ala | 301 | A | . | . | B | . | . | . | −2.13 | 1.56 | . | . | . | −0.60 | 0.16 |
| Thr | 302 | A | . | . | B | . | . | . | −2.69 | 1.56 | . | . | . | −0.60 | 0.16 |
| Trp | 303 | . | . | B | B | . | . | . | −2.47 | 1.51 | . | . | . | −0.60 | 0.16 |
| Val | 304 | . | . | B | B | . | . | . | −2.00 | 1.37 | . | . | . | −0.60 | 0.16 |
| Leu | 305 | . | . | B | B | . | . | . | −2.03 | 1.30 | . | . | . | −0.60 | 0.11 |
| Val | 306 | . | . | B | B | . | . | . | −1.69 | 1.50 | . | . | . | −0.60 | 0.07 |
| Ala | 307 | . | . | B | B | . | . | . | −2.19 | 1.34 | . | . | . | −0.60 | 0.15 |
| Gly | 308 | . | . | B | B | . | . | . | −2.50 | 1.39 | . | . | . | −0.60 | 0.15 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Ile | 309 | A | . | . | B | . | . | . | −1.93 | 1.31 | * | * | . | −0.60 | 0.21 |
| Tyr | 310 | A | . | . | B | . | . | . | −1.01 | 1.59 | * | * | . | −0.60 | 0.21 |
| Leu | 311 | A | . | . | B | . | . | . | −0.19 | 1.09 | * | * | . | −0.60 | 0.42 |
| Met | 312 | A | . | . | B | . | . | . | 0.40 | 1.16 | * | * | . | −0.60 | 0.82 |
| Trp | 313 | A | . | . | B | . | . | . | 0.86 | 0.47 | * | * | . | −0.60 | 0.91 |
| Arg | 314 | A | . | . | B | . | . | . | 0.86 | −0.29 | . | * | . | 0.45 | 2.16 |
| His | 315 | A | . | . | B | . | . | . | 1.14 | −0.29 | * | . | . | 0.45 | 1.53 |
| Glu | 316 | A | . | . | B | . | . | . | 2.00 | −0.90 | * | . | . | 0.75 | 2.91 |
| Arg | 317 | A | A | . | . | . | . | . | 2.29 | −1.81 | * | . | F | 0.90 | 2.97 |
| Ile | 318 | A | A | . | . | . | . | . | 2.28 | −1.33 | * | . | F | 0.90 | 3.15 |
| Lys | 319 | . | A | . | . | T | . | . | 1.47 | −1.44 | * | . | F | 1.30 | 2.43 |
| Lys | 320 | . | A | . | B | T | . | . | 1.20 | −0.66 | * | * | F | 1.30 | 1.08 |
| Thr | 321 | . | A | . | B | . | . | C | 0.89 | −0.27 | * | . | F | 0.80 | 2.06 |
| Ser | 322 | . | A | . | B | . | . | C | 0.47 | −0.47 | * | * | F | 0.80 | 1.48 |
| Phe | 323 | . | . | B | B | . | . | . | 1.04 | 0.01 | * | . | F | 0.00 | 1.07 |
| Ser | 324 | . | . | B | B | . | . | . | 0.19 | 0.50 | . | . | F | −0.30 | 1.07 |
| Thr | 325 | . | . | B | B | . | . | . | −0.67 | 0.70 | . | . | F | −0.45 | 0.66 |
| Thr | 326 | . | . | B | B | . | . | . | −0.57 | 1.00 | . | . | F | −0.45 | 0.63 |
| Thr | 327 | . | . | B | B | . | . | . | −0.48 | 0.64 | . | . | F | −0.45 | 0.72 |
| Leu | 328 | . | . | B | B | . | . | . | −0.67 | 0.69 | . | * | F | −0.45 | 0.78 |
| Leu | 329 | . | . | B | B | . | . | . | −0.32 | 0.89 | * | * | F | −0.45 | 0.38 |
| Pro | 330 | . | . | B | B | . | . | . | −0.87 | 0.40 | * | . | F | −0.15 | 0.52 |
| Pro | 331 | . | . | B | B | . | . | . | −1.37 | 0.56 | * | * | F | −0.45 | 0.47 |
| Ile | 332 | . | . | B | B | . | . | . | −1.91 | 0.56 | * | * | F | −0.45 | 0.47 |
| Lys | 333 | . | . | B | B | . | . | . | −1.96 | 0.51 | * | * | F | −0.45 | 0.23 |
| Val | 334 | . | . | B | B | . | . | . | −1.39 | 0.73 | . | . | . | −0.60 | 0.11 |
| Leu | 335 | . | . | B | B | . | . | . | −1.39 | 1.06 | . | * | . | −0.60 | 0.24 |
| Val | 336 | . | . | B | B | . | . | . | −1.48 | 0.80 | * | * | . | −0.60 | 0.19 |
| Val | 337 | . | . | B | B | . | . | . | 0.59 | 1.19 | * | * | . | −0.60 | 0.34 |
| Tyr | 338 | . | . | . | B | . | T | . | −1.52 | 0.54 | * | . | . | −0.20 | 0.71 |
| Pro | 339 | A | . | . | . | . | T | . | −1.33 | 0.54 | . | . | F | −0.05 | 0.67 |
| Ser | 340 | A | . | . | . | T | T | . | −1.22 | 0.47 | . | * | F | 0.35 | 0.48 |
| Glu | 341 | A | . | . | . | . | T | . | −0.40 | 0.61 | . | . | F | −0.05 | 0.27 |
| Ile | 342 | A | . | . | B | . | . | . | 0.42 | 0.36 | . | . | . | −0.30 | 0.24 |
| Cys | 343 | A | . | . | B | . | . | . | 0.36 | 0.43 | . | * | . | −0.60 | 0.24 |
| Phe | 344 | A | . | . | B | . | . | . | −0.32 | 0.53 | . | * | . | −0.60 | 0.20 |
| His | 345 | A | . | . | B | . | . | . | −0.69 | 1.21 | . | * | . | −0.60 | 0.20 |
| His | 346 | . | . | B | B | . | . | . | −0.93 | 1.10 | . | * | . | −0.60 | 0.20 |
| Thr | 347 | . | . | . | B | T | . | . | −0.74 | 1.29 | . | * | . | −0.20 | 0.36 |
| Ile | 348 | . | . | . | B | T | . | . | −0.39 | 1.29 | * | . | . | −0.20 | 0.23 |
| Cys | 349 | . | . | . | B | T | . | . | 0.31 | 1.27 | * | . | . | −0.20 | 0.24 |
| Tyr | 350 | . | . | . | B | T | . | . | −0.36 | 0.77 | * | . | . | −0.20 | 0.29 |
| Phe | 351 | . | . | B | B | . | . | . | −1.13 | 1.07 | * | . | . | −0.60 | 0.36 |
| Thr | 352 | A | . | . | B | . | . | . | −0.82 | 1.07 | * | . | . | −0.60 | 0.56 |
| Glu | 353 | A | . | . | B | . | . | . | 0.07 | 0.90 | * | . | . | −0.60 | 0.61 |
| Phe | 354 | A | . | . | B | . | . | . | 0.70 | 0.54 | * | . | . | −0.45 | 1.14 |
| Leu | 355 | A | . | . | B | . | . | . | 0.28 | 0.26 | * | * | . | −0.15 | 1.07 |
| Gln | 356 | A | . | . | B | . | . | . | 1.09 | 0.34 | * | * | . | −0.30 | 0.33 |
| Asn | 357 | . | . | . | B | T | . | . | 1.10 | 0.34 | * | * | . | 0.10 | 0.75 |
| His | 358 | . | . | . | B | . | . | C | 1.10 | −0.06 | * | * | . | 0.65 | 1.22 |
| Cys | 359 | . | . | . | . | T | T | . | 0.94 | −0.74 | . | * | . | 1.55 | 1.22 |
| Arg | 360 | A | . | . | . | . | T | . | 0.87 | −0.50 | * | * | F | 1.15 | 0.56 |
| Ser | 361 | A | . | . | . | . | T | . | 0.06 | −0.21 | . | * | F | 0.85 | 0.29 |
| Glu | 362 | A | . | . | . | . | T | . | 0.06 | −0.03 | . | * | F | 0.85 | 0.45 |
| Val | 363 | A | A | . | . | . | . | . | 0.13 | −0.60 | * | * | . | 0.60 | 0.40 |
| Ile | 364 | A | A | . | . | . | . | . | 0.51 | −0.60 | * | * | . | 0.60 | 0.59 |
| Leu | 365 | A | A | . | . | . | . | . | 0.40 | −0.07 | * | * | . | 0.30 | 0.36 |
| Glu | 366 | A | A | . | . | . | . | . | 0.74 | 0.33 | * | . | . | −0.30 | 0.84 |
| Lys | 367 | A | A | . | . | . | . | . | 0.79 | −0.31 | * | * | F | 0.60 | 2.38 |
| Trp | 368 | A | A | . | . | . | . | . | 1.69 | −1.00 | * | . | F | 0.90 | 5.78 |
| Gln | 369 | A | A | . | . | . | . | . | 1.69 | −1.69 | . | . | F | 0.90 | 6.68 |
| Lys | 370 | A | A | . | . | . | . | . | 1.91 | −1.00 | * | . | F | 0.90 | 2.34 |
| Lys | 371 | A | A | . | . | . | . | . | 1.91 | −0.50 | * | . | F | 0.90 | 2.25 |
| Lys | 372 | A | A | . | . | . | . | . | 1.27 | −1.41 | * | . | F | 0.90 | 2.25 |
| Ile | 373 | A | A | . | . | . | . | . | 1.21 | −1.20 | . | . | . | 0.75 | 1.11 |
| Ala | 374 | . | A | B | . | . | . | . | 1.00 | −0.77 | . | . | . | 0.60 | 0.55 |
| Glu | 375 | . | A | B | . | . | . | . | 0.10 | −0.34 | . | . | . | 0.30 | 0.43 |
| Met | 376 | . | A | B | . | . | . | . | 0.06 | 0.30 | * | . | . | −0.30 | 0.45 |
| Gly | 377 | . | . | B | . | . | T | . | −0.28 | 0.01 | . | . | . | 0.10 | 0.77 |
| Pro | 378 | A | . | . | . | . | T | . | −0.20 | 0.43 | . | . | . | −0.20 | 0.47 |
| Val | 379 | A | . | . | . | . | T | . | −0.20 | 1.11 | . | . | . | −0.20 | 0.39 |
| Gln | 380 | A | . | . | . | . | T | . | −0.51 | 1.00 | . | . | . | −0.20 | 0.40 |
| Trp | 381 | A | A | . | . | . | . | . | 0.09 | 1.06 | . | . | . | −0.60 | 0.37 |
| Leu | 382 | A | A | . | . | . | . | . | 0.48 | 1.03 | . | . | . | −0.60 | 0.87 |
| Ala | 383 | A | A | . | . | . | . | . | 0.73 | 0.39 | . | . | . | −0.15 | 1.00 |
| Thr | 384 | A | A | . | . | . | . | . | 1.00 | −0.01 | * | . | F | 0.60 | 1.91 |
| Gln | 385 | A | A | . | . | . | . | . | 0.41 | −0.43 | * | . | F | 0.60 | 2.34 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Lys | 386 | A | A | . | . | . | . | . | 0.70 | −0.61 | * | . | F | 0.90 | 2.34 |
| Lys | 387 | A | A | . | . | . | . | . | 1.56 | −1.11 | * | . | F | 0.90 | 2.71 |
| Ala | 388 | A | A | . | . | . | . | . | 1.29 | −1.60 | * | . | F | 0.90 | 3.12 |
| Ala | 389 | A | A | . | . | . | . | . | 0.74 | −1.36 | * | . | F | 0.90 | 1.16 |
| Asp | 390 | A | A | . | . | . | . | . | 0.04 | −0.71 | * | . | F | 0.75 | 0.43 |
| Lys | 391 | A | A | . | . | . | . | . | −0.81 | 0.07 | * | . | . | −0.30 | 0.37 |
| Val | 392 | . | A | B | . | . | . | . | −1.67 | 0.26 | * | . | . | −0.30 | 0.30 |
| Val | 393 | . | A | B | . | . | . | . | −1.38 | 0.44 | * | . | . | −0.60 | 0.15 |
| Phe | 394 | . | A | B | . | . | . | . | −0.79 | 0.83 | * | . | . | −0.60 | 0.10 |
| Leu | 395 | . | A | B | . | . | . | . | −0.79 | 1.23 | * | . | . | −0.60 | 0.22 |
| Leu | 396 | . | A | B | . | . | . | . | −1.69 | 0.59 | * | * | . | −0.60 | 0.49 |
| Ser | 397 | . | A | . | . | T | . | . | −0.83 | 0.59 | * | . | F | −0.05 | 0.42 |
| Asn | 398 | . | . | . | . | T | . | . | −0.28 | 0.20 | * | . | F | 0.45 | 0.81 |
| Asp | 399 | . | . | . | . | T | T | . | −0.43 | −0.10 | * | . | F | 1.40 | 1.32 |
| Val | 400 | . | . | . | . | T | T | . | −0.29 | −0.14 | * | . | F | 1.25 | 0.73 |
| Asn | 401 | . | . | B | . | T | T | . | 0.52 | 0.04 | * | * | F | 0.65 | 0.24 |
| Ser | 402 | . | . | B | . | . | T | . | 0.48 | −0.36 | * | . | . | 0.70 | 0.24 |
| Val | 403 | . | . | B | . | . | . | . | 0.17 | 0.07 | * | . | . | 0.21 | 0.32 |
| Cys | 404 | . | . | B | . | . | T | . | −0.50 | −0.09 | * | . | . | 1.32 | 0.29 |
| Asp | 405 | . | . | B | . | . | T | . | 0.01 | 0.09 | . | . | F | 1.18 | 0.12 |
| Gly | 406 | . | . | . | . | T | T | . | 0.06 | 0.13 | . | . | F | 1.89 | 0.16 |
| Thr | 407 | . | . | . | . | T | T | . | 0.06 | −0.51 | . | . | F | 3.10 | 0.58 |
| Cys | 408 | . | . | B | . | . | T | . | 0.91 | −0.70 | . | . | F | 2.39 | 0.47 |
| Gly | 409 | . | . | . | . | T | T | . | 1.23 | −0.70 | . | . | F | 2.48 | 0.81 |
| Lys | 410 | . | . | . | . | T | T | . | 0.93 | −0.70 | . | . | F | 2.17 | 0.56 |
| Ser | 411 | . | . | . | . | . | T | C | 1.07 | −0.80 | . | . | F | 1.81 | 1.40 |
| Glu | 412 | . | . | . | . | . | . | C | 1.08 | −0.94 | . | . | F | 1.30 | 2.18 |
| Gly | 413 | . | . | . | . | . | . | C | 1.74 | −0.99 | . | * | F | 1.64 | 1.46 |
| Ser | 414 | . | . | . | . | . | T | C | 2.09 | −0.99 | . | * | F | 2.18 | 1.89 |
| Pro | 415 | . | . | . | . | . | T | C | 1.74 | −0.97 | . | * | F | 2.52 | 1.75 |
| Ser | 416 | . | . | . | . | . | T | C | 2.04 | −0.59 | . | . | F | 2.86 | 2.38 |
| Glu | 417 | . | . | . | . | T | T | . | 2.04 | −0.61 | . | . | F | 3.40 | 3.07 |
| Asn | 418 | . | . | . | . | T | . | . | 2.09 | −1.00 | . | . | F | 2.86 | 3.32 |
| Ser | 419 | . | . | . | . | T | T | . | 2.09 | −1.04 | . | . | F | 2.93 | 3.32 |
| Gln | 420 | . | . | . | . | T | T | . | 2.09 | −1.04 | . | . | F | 2.80 | 2.57 |
| Asp | 421 | . | . | . | . | T | T | . | 1.72 | −0.61 | . | . | F | 2.67 | 2.47 |
| Ser | 422 | . | . | . | . | T | T | . | 0.91 | −0.44 | . | . | F | 2.09 | 0.99 |
| Ser | 423 | . | . | . | . | . | T | C | 0.52 | −0.14 | . | . | F | 2.10 | 0.47 |
| Pro | 424 | . | . | B | . | . | T | . | 0.43 | −0.11 | . | . | . | 1.54 | 0.36 |
| Cys | 425 | . | . | B | . | . | T | . | 0.04 | 0.31 | . | . | . | 0.73 | 0.34 |
| Leu | 426 | . | . | B | . | . | T | . | −0.34 | 0.36 | . | . | . | 0.52 | 0.33 |

Among highly preferred fragments in this regard are those that comprise reigons of IL17RLP that combine several structural features, such as several features set out above.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 209198. By "stringent hybridization conditions" is intended overnight incubation at 42° C. in a solution comprising: 50% formamide, 5× SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1× SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A, 1B, and 1C (SEQ ID NO:1)). Of course, a polynucleotide which hybridizes only to a poly A sequence (such as the 3' terminal poly(A) tract of the IL17RLP cDNA shown in FIGS. 1A, 1B, and 1C (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

In preferred embodiments, polynucleotides which hybridize to the reference polynucleotides disclosed herein encode polypeptides which either retain substantially the same biological function or activity as the mature form of the IL17RLP polypeptide encoded by the polynucleotide sequence depicted in FIGS. 1A, 1B, and 1C (SEQ ID NO:1) or the clone contained in the deposit (HAPOR40).

Alternative embodiments are directed to polynucleotides which hybridize to the reference polynucleotide (i.e., a polynucleotide sequence disclosed herein), but do not retain biological activity. While these polynucleotides do not retain biological activity, they have uses, such as, for example, as probes for the polynucleotides of SEQ ID NO:1, for recovery of the polynucleotides, as diagnostic probes, and as PCR primers.

As indicated, nucleic acid molecules of the present invention which encode a IL17RLP polypeptide may include, but are not limited to those encoding the amino acid sequence of the mature polypeptide, by itself; and the coding sequence for the mature polypeptide and additional sequences, such as those encoding the about 19 amino acid leader or secretory sequence, such as a pre-, or pro- or prepro-protein sequence; the coding sequence of the mature polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described by Gentz and colleagues (*Proc. Natl. Acad. Sci. USA* 86:821–824 (1989)), for instance, hexa-histidine provides for convenient purification of the fusion protein. The "HA" tag is another peptide useful for purification which corresponds to an epitope derived from the influenza hemagglutinin protein, which has been described by Wilson and coworkers (*Cell* 37:767 (1984)). As discussed below, other such fusion proteins include the IL17RLP fused to Fc at the N- or C-terminus.

The present invention further relates to variants of the nucleic acid molecules of the present invention, which encode portions, analogs or derivatives of the IL17RLP protein. Variants may occur naturally, such as a natural allelic variant. By an "allelic variant" is intended one of several alternate forms of a gene occupying a given locus on a chromosome of an organism (*Genes II*, Lewin, B., ed., John Wiley & Sons, New York (1985)). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the IL17RLP protein or portions thereof. Also especially preferred in this regard are conservative substitutions.

Most highly preferred are nucleic acid molecules encoding the mature protein having the amino acid sequence shown in SEQ ID NO:2 or the mature IL17RLP amino acid sequence encoded by the deposited cDNA clone.

Most highly preferred are nucleic acid molecules encoding the extracellular domain of the protein having the amino acid sequence shown in SEQ ID NO:2 or the extracellular domain of the IL17RLP amino acid sequence encoded by the deposited cDNA clone.

Thus, one aspect of the invention provides an isolated nucleic acid molecule comprising a polynucleotide having a nucleotide sequence selected from the group consisting of:

(a) a nucleotide sequence encoding the IL17RLP polypeptide having the complete amino acid sequence in SEQ ID NO:2 (i.e., positions −19 to 407 of SEQ ID NO:2); (b) a nucleotide sequence encoding the IL17RLP polypeptide having the complete amino acid sequence in SEQ ID NO:2 excepting the N-terminal methionine (i.e., positions −18 to 407 of SEQ ID NO:2); (c) a nucleotide sequence encoding the predicted mature IL17RLP polypeptide having the amino acid sequence at positions 1 to 407 in SEQ ID NO:2; (d) a nucleotide sequence encoding a polypeptide comprising the predicted extracellular domain of the IL17RLP polypeptide having the amino acid sequence at positions 1 to 271 in SEQ ID NO:2; (e) a nucleotide sequence encoding a soluble IL17RLP polypeptide having the predicted extracellular and intracellular domains, but lacking the predicted transmembrane domain; (f) a nucleotide sequence encoding the IL17RLP polypeptide having the complete amino acid sequence encoded by the human cDNA contained in ATCC Deposit No. 209198; (g) a nucleotide sequence encoding the IL17RLP polypeptide having the complete amino acid sequence excepting the N-terminal methionine encoded by the human cDNA contained in ATCC Deposit No. 209198; (h) a nucleotide sequence encoding the mature IL17RLP polypeptide having the amino acid sequence encoded by the human cDNA contained in ATCC Deposit No. 209198; (i) a nucleotide sequence encoding the extracellular domain of the IL17RLP polypeptide having the amino acid sequence encoded by the human cDNA contained in ATCC Deposit No. 209198; and () a nucleotide sequence complementary to any of the nucleotide sequences in (a), (b), (c), (d), (e), (f), (g), (h) or (i) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e), (f), (g), (h) or (i), above, or a polynucleotide which hybridizes under stringent hybridization conditions to a polynucleotide in (a), (b), (c), (d), (e), (f), (g), (h) or (i), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a IL17RLP polypeptide having an amino acid sequence in (a), (b), (c), (d), (e), (f), (g) or (h), above. A further nucleic acid embodiment of the invention relates to an isolated nucleic acid molecule comprising a polynucleotide which encodes the amino acid sequence of a IL17RLP polypeptide having an amino acid sequence which contains at least one conservative amino acid substitution, but not more than 50 conservative amino acid substitutions, even more preferably, not more than 40 conservative amino acid substitutions, still more preferably not more than 30 conservative amino acid substitutions, and still even more preferably not more than 20 conservative amino acid substitutions. Of course, in order of ever-increasing preference, it is highly preferable for a polynucleotide which encodes the amino acid sequence of a IL17RLP polypeptide to have an amino acid sequence which contains not more than 10–20, 10–15, 7–15, 7–10, 5–10, 3–7, 3–5, 2–5, 1–5, 1–3, 10, 9, 8, 7, 6, 5, 4, 3, 2 or 1 conservative amino acid substitutions.

The present invention also relates to recombinant vectors, which include the isolated nucleic acid molecules of the present invention, and to host cells containing the recombinant vectors, as well as to methods of making such vectors and host cells and for using them for production of IL17RLP polypeptides or peptides by recombinant techniques.

By a polynucleotide having a nucleotide sequence at least, for example, 95% "identical" to a reference nucleotide sequence encoding a IL17RLP polypeptide is intended that the nucleotide sequence of the polynucleotide is identical to the reference sequence except that the polynucleotide sequence may include up to five point mutations per each 100 nucleotides of the reference nucleotide sequence encoding the IL17RLP polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIGS. 1A, 1B, and 1C or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman to find the best segment of homology between two sequences (*Advances in Applied Mathematics* 2:482–489 (1981)). When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed. A preferred method for determing the best overall match between a query sequence (a sequence of the present invention) and a subject sequence, also referred to as a global sequence alignment, can be determined using the FASTDB computer program based on the algorithm of Brutlag and colleagues (*Comp. App. Biosci.* 6:237–245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is becuase the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignement of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequnce are manually corrected for. No other manual corrections are to made for the purposes of the present invention.

In certain preferred embodiments, IL17RLP proteins of the invention comprise fusion proteins as described herein wherein the IL17RLP polypeptides are those described as $n^1$–$m^1$, $n^2$–$m^2$, and/or $n^3$–$m^3$ herein. In preferred embodiments, the application is directed to nucleic acid molecules at least 90%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

The present application is directed to nucleic acid molecules at least 90%, 95%, 96%, 97%, 98% or 99% identical to the nucleic acid sequence shown in FIGS. 1A, 1B, and 1C (SEQ ID NO:1) or to the nucleic acid sequence of the deposited cDNA, irrespective of whether they encode a polypeptide having IL17RLP activity. This is because even where a particular nucleic acid molecule does not encode a polypeptide having IL17RLP activity, one of skill in the art would still know how to use the nucleic acid molecule, for instance, as a hybridization probe or a polymerase chain reaction (PCR) primer. Uses of the nucleic acid molecules of the present invention that do not encode a polypeptide having IL17RLP activity include, inter alia, (1) isolating the IL17RLP gene or allelic variants thereof in a cDNA library; (2) in situ hybridization (e.g., "FISH") to metaphase chromosomal spreads to provide precise chromosomal location of the IL17RLP gene, as described by Verma and colleagues (*Human Chromosomes: A Manual of Basic Techniques*, Pergamon Press, New York (1988)); and Northern Blot analysis for detecting IL17RLP mRNA expression in specific tissues.

Preferred, however, are nucleic acid molecules having sequences at least 90%, 95%, 96%, 97%, 98% or 99% identical to the nucleic acid sequence shown in FIGS. 1A, 1B, and 1C (SEQ ID NO:1) or to the nucleic acid sequence of the deposited cDNA which do, in fact, encode a polypeptide having IL17RLP protein activity. By "a polypeptide having IL17RLP activity" is intended polypeptides exhibiting activity similar, but not necessarily identical, to an activity of the mature or soluble form of the IL17RLP protein of the invention, as measured in a particular biological assay. For example, the IL17RLP protein of the present invention modulates IL-6 secretion from NIH-3T3 cells. An in vitro ELISA assay which quantitates the amount of IL-6 secreted from cells in response to treatment with cytokines or the soluble extracellular domains of cytokine receptors has been described (Yao, Z., et al., *Immunity* 3:811–821 (1995)). Briefly, the assay involves plating the target cells at a density of approximately $5 \times 10^6$ cells/mL in a volume of 500 μL in the wells of a 24 well flat-bottomed culture plate (Costar). The cultures are then treated with various concentrations of the cytokine or the soluble extracellular domain of cytokine receptor in question The cells are then cultured for 24 hours at 37° C. At this time, 50 μL of supernatant is removed and assayed for the quantity of IL-6 essentially as described by the manufacturer (Genzyme, Boston, Mass.). IL-6 levels are then calculated by reference to a standard curve constructed with recombinant IL-17 cytokine. Such activity is useful for determining the level of IL17RLP-mediated IL-6 secretion.

IL17RLP protein modulates immune system cell proliferation and differentiation in a dose-dependent manner in the above-described assay. Thus, "a polypeptide having IL17RLP protein activity" includes polypeptides that also exhibit any of the same stimulatory activities in the above-described assays in a dose-dependent manner. Although the degree of dose-dependent activity need not be identical to that of the IL17RLP protein, preferably, "a polypeptide having IL17RLP protein activity" will exhibit substantially similar dose-dependence in a given activity as compared to the IL17RLP protein (i.e., the candidate polypeptide will exhibit greater activity or not more than about 25-fold less and, preferably, not more than about tenfold less activity relative to the reference IL17RLP protein).

Lymphocyte proliferation is another in vitro assay which may be performed to determine the activity of IL17RLP and soluble, extracellular domains of IL17RLP. For example, Yao and colleagues (*Immunity* 3:811–821 (1995)) have recently described an in vitro assay for determining the effects of various cytokines and soluble cytokine receptors on the proliferation of murine leukocytes. Briefly, lymphoid organs are harvested aseptically, lymphocytes are isolated from the harvested organs, and the resulting collection of lymphoid cells are suspended in standard culture medium as described by Fanslow and coworkers (J. Immunol. 147:535–5540 (1991)). The lymphoid cell suspensions may then be divided into several different subclasses of lymphoid cells including splenic T-cells, lymph node B-cells, $CD4^+$ and $CD8^+$ T-cells, and mature adult thymocytes. For splenic T-cells, spleen cell suspensions ($200 \times 10^6$ cells) are incubated with CD11b mAb and class II MHC mAb for 30 min at 4° C., loaded on a T-cell purification column (Pierce, Rockford, Ill.), and the T-cells eluted according to the manufacturer's instructions. Using this method, purity of the resulting T-cell populations should be >95% $CD3^+$ and <1% $sIgM^+$. For purification of lymph node subsets, B-cells are removed from by adherence to tissue culture dishes previously coated with goat anti-mouse IgG (10 μg/mL). Remaining cells were then incubated with anti-CD4 or anti-CD8 for 30 min at 4° C. then washed and placed on tissue culture dishes previously coated with goat anti-rat IgG (20 μg/mL). After 45 min, nonadherent cells are removed and tested for purity by flow cytometry. CD4 and surface Ig-depleted cells should be >90% TCR-ab, $CD8^+$, whereas CD8 and surface Ig-depleted cells should be >95% TCR-ab, $CD4^+$. Finally, to enrich for mature adult thymocytes, cells are suspended at $10^8$/mL in 10% anti-HSA and 10% low tox rabbit complement (Cedarlane, Ontario, Canada), incubated for 45 min at 37° C., and remaining viable cells isolated over Ficoll-Hypaque (Pharmacia, Piscataway, N.J.). This procedure should yield between 90 and 95% $CD3^{hi}$ cells that are either $CD4^+8^-$ or $CD4^-8^+$.

To analyze the proliferative response of the above-described primary cell cultures, in vitro proliferation assays are set up in round bottom or flat bottom 96-well plates using $0.5–1.5 \times 10^5$ cells/well. For stimulation, T-cells are incubated with suboptimal concentrations (0.25–0.5 μg/mL) of Con A (Sigma, St. Louis, Mo.), PHA (0.25–0.5%; Difco, Detroit, Mich.), immobilized anti-CD3, or immobilized anti-TCR-ab. Anti-CD3 and anti-TCR-ab are immobilized for >2 hours at 37° C. before the addition of effector cells. Incubations are done in the presence and absence of fixed CV-1/EBNA cells transfected with IL17RLP, muteins thereof, a control vector, or a control antigen such as rCD40L (Armitage, et al., *Nature* 357:80 (1992)); Spriggs, et al., *J. Exp. Med.* 176:1543 (1992)). Surface expression of CD40L is monitored by flow cytometry using a human CD40-Fc fusion protein. Cell cultures are pulsed overnight with $[^3H]$-thymidine (1 μCi/well) for the last 18 hours of a 3 day culture. Labeled cultures are then harvested on a 96-well Inotech harvester and radioactive counts detected using a scintillation counter.

Like other cytokine receptors, IL17RLP exhibits activity on leukocytes including for example monocytes, lymphocytes and neutrophils. For this reason IL17RLP is active in directing the proliferation and differentiation of these cell types. Such activity is useful for immune enhancement or suppression, myeloprotection, stem cell mobilization, acute and chronic inflammatory control and treatment of leukemia. Assays for measuring such activity are well known in the art (Peters, et al., *Immun. Today* 17:273 (1996); Young, et al., *J. Exp. Med.* 182:1111 (1995); Caux, et al., *Nature* 390:258 (1992); and Santiago-Schwarz, et al., *Adv. Exp. Med. Biol.* 378:7 (1995).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIGS. 1A, 1B, and 1C (SEQ ID NO:1) will encode a polypeptide "having IL17RLP protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having IL17RLP protein activity. This is because the skilled artisan is fully aware of amino acid substitutions that are either less likely or not likely to significantly effect protein function (e.g., replacing one aliphatic amino acid with a second aliphatic amino acid), as further described below.

In specific embodiments, antagonists according to the present invention are nucleic acids corresponding to the sequences contained in IL17RLP, or the complementary strand thereof, and/or to nucleotide sequences contained in the deposited clone HAPOR40. In one embodiment, antisense sequence is generated internally by the organism, in another embodiment, the antisense sequence is separately administered (see, for example, O'Connor, J., Neurochem. 56:560 (1991), and Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the IL17RLP antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the IL17RLP antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding IL17RLP, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:39–42 (1982)), etc.

The antisense nucleic acids of the invention comprise a sequence complementary to at least a portion of an RNA transcript of aN IL17RLP gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded IL17RLP antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a IL17RLP RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'- non-translated, non-coding regions of the IL17RLP shown in FIGS. 1A, 1B, and 1C could be used in an antisense approach to inhibit translation of endogenous IL17RLP mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of IL17RLP mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553–6556 (1989); Lemaitre et al., Proc. Natl. Acad. Sci. 84:648–652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., BioTechniques 6:958–976 (1988)) or intercalating agents. (See, e.g., Zon, Pharm. Res. 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res. 15:6625–6641 (1987)). The oligonucleotide is a 2-0-methylribonucleotide (Inoue et al., Nucl. Acids Res. 15:6131–6148 (1987)), or a chimeric RNA-DNA analogue (Inoue et al., FEBS Lett. 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res. 16:3209 (1988)), methylphosphonate oligonucleotides can be prepared by use of controlled pore glass polymer supports (Sarin et al., Proc. Natl. Acad. Sci. U.S.A. 85:7448–7451 (1988)), etc.

While antisense nucleotides complementary to the IL17RLP coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222–1225 (1990). While ribozymes that cleave mRNA at site specific recognition sequences can be used to destroy IL17RLP mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of IL17RLP (FIGS. 1A, 1B, and 1C (SEQ ID NO:1)). Preferably, the ribozyme is engineered so that the cleavage recognition site is located near the 5' end of the IL17RLP mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express IL17RLP in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous IL17RLP messages and inhibit translation. Since ribozymes unlike antisense molecules, are catalytic, a lower intracellular concentration is required for efficiency.

Endogenous gene expression can also be reduced by inactivating or "knocking out" the IL17RLP gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be. apparent to those of skill in the art. The contents of each of the documents recited in this paragraph is herein incorporated by reference in its entirety.

In other embodiments, antagonists according to the present invention include soluble forms of IL17RLP (e.g., fragments of the IL17RLP shown in FIGS. 1A, 1B, and 1C (SEQ ID NO:2) that include the ligand binding domain from the extracellular region of the full length receptor). Such soluble forms of the IL17RLP, which may be naturally occurring or synthetic, antagonize IL17RLP-mediated signaling by competing with the cell surface bound forms of the receptor for binding to IL-20 or IL-20-like ligands. Antagonists of the present invention also include antibodies specific for IL17RLP ligands and IL17RLP-Fc fusion proteins.

The present invention also relates to vectors which include the isolated DNA molecules of the present invention, host cells which are genetically engineered with the recombinant vectors, and the production of IL17RLP polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Vectors preferred for use in bacteria include pHE4-5, pQE70, pQE60 and pQE-9 (QIAGEN, Inc., supra); pBS vectors, Phagescript vectors, Bluescript vectors, pNH8A, pNH16a, pNH18A, pNH46A (Stratagene); and ptrc99a, pKK223-3, pKK233-3, pDR540, pRIT5 (Pharmacia). Among preferred eukaryotic vectors are pWLNEO, pSV2CAT, pOG44, pXT1, and pSG (Stratagene); and pSVK3, pBPV, pMSG and pSVL (Pharmacia). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals (for example, Davis, et al., *Basic Methods In Molecular Biology* (1986)).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5 (Bennett, D., et al., *J. Molecular Recognition* 8:52–58 (1995); Johanson, K., et al., *J. Biol. Chem.* 270:9459–9471 (1995)).

The IL17RLP protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., IL17RLP coding sequence), and/or to include genetic material (e.g., heterologous polynucleotide sequences) that is operably associated with IL17RLP polynucleotides of the invention, and which activates, alters, and/or amplifies endogenous IL17RLP polynucleotides. For example, techniques known in the art may be used to operably associate heterologous control regions (e.g., promoter and/or enhancer) and endogenous IL17RLP polynucleotide sequences via homologous recombination (see, e.g., U.S. Pat. No. 5,641,670, issued Jun. 24, 1997; International Publication Number WO 96/29411, published Sep. 26, 1996; International Publication Number WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

Polypeptides and Fragments

The invention further provides an isolated IL17RLP polypeptide having the amino acid sequence encoded by the deposited cDNA, or the amino acid sequence in SEQ ID NO:2, or a peptide or polypeptide comprising a portion of the above polypeptides.

To improve or alter the characteristics of IL17RLP polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron and colleagues (*J. Biol. Chem.*, 268:2984–2988 (1993)) reported modified KGF proteins that had heparin binding activity even if 3, 8, or 27 N-terminal amino acid residues were missing. In the present case, since the protein of the invention is a member of the interleukin (IL)-17 receptor polypeptide family, deletions of N-terminal amino acids up to the cysteine at position 5 of SEQ ID NO:2 may retain some biological activity such as ligand binding or modulation of target cell activities. Polypeptides having further N-terminal deletions including the cysteine residue at position 5 in SEQ ID NO:2 would not be expected to retain such biological activities because it is known that this residue in the murine IL-17 receptor polypeptide is likely required for forming a disulfide bridge to provide structural stability which is needed for ligand binding and the initiation of the appropriate signal transduction pathways.

However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete, mature or extracellular domain of the protein generally will be retained when less than the majority of the residues of the complete, mature or extracellular domain of the protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the IL17RLP shown in SEQ ID NO:2, up to the cysteine residue at position number 5, and polynucleotides encoding such polypeptides. In particular, the present invention provides polypeptides comprising the amino acid sequence of residues $n^1$–407 of SEQ ID NO:2, where $n^1$ is an integer in the range of –19 to 5, and 5 is the position of the first residue from the N-terminus of the complete IL17RLP polypeptide (shown in SEQ ID NO:2) believed to be required for ligand binding activity of the IL17RLP protein.

More in particular, the invention provides polynucleotides encoding polypeptides having the amino acid sequence of residues of –18–407, –17–407, –16–407, –15–407, –14–407, –13–407, –12–407, –11–407, –10–407, –9–407, –8–407, –7–407, –6–407, –5–407, –4–407, –3–407, –2–407, –1–407, 1–407, 2–407, 3–407, 4–407, and 5–407 of SEQ ID NO:2. Polynucleotides encoding these polypeptides also are provided.

Similarly, many examples of biologically functional C-terminal deletion muteins are known. For instance, Interferon gamma shows up to ten times higher activities by deleting 8–10 amino acid residues from the carboxy terminus of the protein (Dobeli, et al., *J. Biotechnology* 7:199–216 (1988)). In the present case, since the protein of the invention is a member of the interleukin (IL)-17 receptor polypeptide family, deletions of C-terminal amino acids up to the cysteine at position 340 of SEQ ID NO:2 may retain some biological activity such as ligand-binding. Polypeptides having further C-terminal deletions including the cysteine residue at position 340 of SEQ ID NO:2 would not be expected to retain such biological activities because it is known that this residue in the murine IL-17 receptor polypeptide is likely required for forming a disulfide bridge to provide structural stability which is needed for receptor binding and signal transduction.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete, mature or extracellular domain of the protein generally will be retained when less than the majority of the residues of complete, mature or extracellular domain of the protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the IL17RLP shown in SEQ ID NO:2, up to the cysteine residue at position 340 of SEQ ID NO:2, and polynucleotides encoding such polypeptides. In particular, the present invention provides polypeptides having the amino acid sequence of residues –19–$m^1$ of the amino acid sequence in SEQ ID NO:2, where $m^1$ is any integer in the range of 340 to 407, and residue 340 is the position of the first residue from the C-terminus of the complete IL17RLP polypeptide (shown in SEQ ID NO:2) believed to be required for the IL17RLP protein to transfer its extracellular signal to the interior of the cell.

More in particular, the invention provides polynucleotides encoding polypeptides having the amino acid sequence of residues –19–340, –19–341, –19–342, –19–343, –19–344, –19–345, –19–346, –19–347, –19–348, –19–349, –19–350, –19–351, –19–352, –19–353, –19–354, –19–355, –19–356, –19–357, –19–358, –19–359, –19–360, –19–361, –19–362, –19–363, –19–364, –19–365, –19–366, –19–367, –19–368, –19–369, –19–370, –19–371, –19–372, –19–373, –19–374, –19–375, –19–376, –19–377, –19–378, –19–379, –19–380, –19–381, –19–382, –19–383, –19–384, –19–385, –19–386, –19–387, –19–388, –19–389, –19–390, –19–391, –19–392, –19–393, –19–394, –19–395, –19–396, –19–397, –19–398, –19–399, –19–400, –19–401, –19–402, –19–403, –19–404, –19–405, –19–406, and –19–407 of SEQ ID NO:2. Polypeptides encoded by these polynucleotides are also encompassed by the invention.

The invention also provides polypeptides having one or more amino acids deleted from both the amino and the carboxyl termini, which may be described generally as having residues $n^1$–$m^1$ of SEQ ID NO:2, where $n^1$ and $m^1$ are integers as described above.

Also included are a nucleotide sequence encoding a polypeptide consisting of a portion of the complete IL17RLP amino acid sequence encoded by the cDNA clone contained in ATCC Deposit No. 209198, where this portion excludes from 1 to about 23 amino acids from the amino terminus of the complete amino acid sequence encoded by the cDNA clone contained in ATCC Deposit No. 209198, or from 1 to about 67 amino acids from the carboxy terminus, or any combination of the above amino terminal and carboxy terminal deletions, of the complete amino acid sequence encoded by the cDNA clone contained in ATCC Deposit No. 209198. Polynucleotides encoding all of the above deletion mutant polypeptide forms also are provided.

As mentioned above, even if deletion of one or more amino acids from the N-terminus of a protein results in modification of loss of one or more biological functions of the protein, other biological activities may still be retained. Thus, the ability of the shortened IL17RLP mutein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art. It is not unlikely that a IL17RLP mutein with a large number of deleted N-terminal amino acid residues may retain some biological or immungenic activities. In fact, peptides composed of as few as six IL17RLP amino acid residues may often evoke an immune response.

Accordingly, the present invention further provides polypeptides having one or more residues deleted from the amino terminus of the IL17RLP amino acid sequence shown in SEQ ID NO:2, up to the aspartic acid residue at position number 421 and polynucleotides encoding such polypeptides. In particular, the present invention provides polypeptides comprising the amino acid sequence of residues $n^2$–426 of FIGS. 1A, 1B, and 1C (SEQ ID NO:2), where $n^2$ is an integer in the range of 2 to 421, and 422 is the position of the first residue from the N-terminus of the complete IL17RLP polypeptide believed to be required for at least immunogenic activity of the IL17RLP protein.

More in particular, the invention provides polynucleotides encoding polypeptides comprising, or alternatively consisting of, the amino acid sequence of residues of S-2 to L-426; L-3 to L-426; V-4 to L-426; L-5 to L-426; L-6 to L-426; S-7 to L-426; L-8 to L-426; A-9 to L-426; A-10 to L-426; L-11 to L-426; C-12 to L-426; R-13 to L-426; S-14 to L-426; A-15 to L-426; V-16 to L-426; P-17 to L-426; R-18 to L-426; E-19 to L-426; P-20 to L-426; T-21 to L-426; V-22 to L-426; Q-23 to L-426; C-24 to L-426; G-25 to L-426; S-26 to L-426; E-27 to L-426; T-28 to L-426; G-29 to L-426; P-30 to L-426; S-31 to L-426; P-32 to L-426; E-33 to L-426; W-34 to L-426; M-35 to L-426; L-36 to L-426; Q-37 to L-426; H-38 to L-426; D-39 to L-426; L-40 to L-426; I-41 to L-426; P42 to L-426; G-43 to L-426; D-44 to L-426; L-45 to L-426; R-46 to L-426; D-47 to L-426; L-48 to L-426; R-49 to L-426; V-50 to L-426; E-51 to L-426; P-52 to L-426; V-53 to L-426; T-54 to L-426; T-55 to L-426; S-56 to L-426; V-57 to L-426; A-58 to L-426; T-59 to L-426; G-60 to L-426; D-61 to L-426; Y-62 to L-426; S-63 to L-426; I-64 to L-426; L-65 to L-426; M-66 to L-426; N-67 to L-426; V-68 to L-426; S-69 to L-426; W-70 to L426; V-71 to L-426; L-72 to L-426; R-73 to L-426; A-74 to L-426; D-75 to L-426; A-76 to L-426; S-77 to L-426; I-78 to L-426; R-79 to L-426; L-80 to L-426; L-81 to L-426; K-82 to L-426; A-83 to L-426; T-84 to L-426; K-85 to L-426; I-86 to L-426; C-87 to L-426; V-88 to L426; T-89 to L-426; G-90 to L-426; K-91 to L-426; S-92 to L-426; N-93 to L-426; F-94 to L-426; Q-95 to L-426; S-96 to L-426; Y-97 to L-426; S-98 to L-426; C-99 to L-426; V-100 to L-426; R-101 to L-426; C-102 to L-426; N-103 to L-426; Y-104 to L-426; T-105 to L-426; E-106 to L-426; A-107 to L-426; F-108 to L-426; Q-109 to L-426; T-110 to L-426; Q-111 to L-426; T-112 to L-426; R-113 to L-426; P-114 to L-426; S-115 to L-426; G-116 to L-426; G-117 to L-426; K-118 to L-426; W-119 to L-426; T-120 to L-426; F-121 to L-426; S-122 to L-426; Y-123 to L-426; I-124 to L-426; G-125 to L-426; F-126 to L-426; P-127 to L-426; V-128 to L-426; E-129 to L-426; L-130 to L-426; N-131 to L-426; T-132 to L-426; V-133 to L-426; Y-134 to L-426; F-135 to L-426; I-136 to L-426; G-137 to L-426; A-138 to L-426; H-139 to L-426; N-140 to L-426; I-141 to L-426; P-142 to L-426; N-143 to L-426; A-144 to L-426; N-145 to L-426; M-146 to L-426; N-147 to L-426; E-148 to L-426; D-149 to L-426; G-150 to L-426; P-151 to L-426; S-152 to L-426; M-153 to L-426; S-154 to L-426; V-155 to L-426; N-156 to L-426; F-157 to L-426; T-158 to L-426; S-159 to L-426; P-160 to L-426; G-161 to L-426; C-162 to L-426; L-163 to L-426; D-164 to L-426; H-165 to L-426; I-166 to L-426; M-167 to L-426; K-168 to L-426; Y-169 to L-426; K-170 to L-426; K-171 to L-426; K-172 to L-426; C-173 to L-426; V-174 to L-426; K-175 to L-426; A-176 to L-426; G-177 to L-426; S-178 to L-426; L-179 to L-426; W-180 to L-426; D-181 to L-426; P-182 to L-426; N-183 to L-426; I-184 to L-426; T-185 to L-426; A-186 to L-426; C-187 to L-426; K-188 to L-426; K-189 to L-426; N-190 to L-426; E-191 to L-426; E-192 to L-426; T-193 to L-426; V-194 to L-426; E-195 to L-426; V-196 to L-426; N-197 to L-426; F-198 to L-426; T-199 to L-426; T-200 to L-426; T-201 to L-426; P-202 to L-426; L-203 to L-426; G-204 to L-426; N-205 to L-426; R-206 to L-426; Y-207 to L-426; M-208 to L-426; A-209 to L-426; L-210 to L-426; I-211 to L-426; Q-212 to L-426; H-213 to L-426; S-214 to L-426; T-215 to L-426; I-216 to L-426; I-217 to L-426; G-218 to L-426; F-219 to L-426; S-220 to L-426; Q-221 to L-426; V-222 to L-426; F-223 to L-426; E-224 to L-426; P-225 to L-426; H-226 to L-426; Q-227 to L-426; K-228 to L-426; K-229 to L-426; Q-230 to L-426; T-231 to L-426; R-232 to L-426; A-233 to L-426; S-234 to L-426; V-235 to L-426; V-236 to L-426; I-237 to L-426; P-238 to L-426; V-239 to L-426; T-240 to L-426; G-241 to L-426; D-242 to L-426; S-243 to L-426; E-244 to L-426; G-245 to L-426; A-246 to L-426; T-247 to L-426; V-248 to L-426; Q-249 to L-426; L-250 to L-426; T-251 to L-426; P-252 to L-426; Y-253 to L-426; F-254 to L-426; P-255 to L-426; T-256 to L-426; C-257 to L-426; G-258 to L-426; S-259 to L-426; D-260 to L-426; C-261 to L-426; I-262 to L-426; R-263 to L-426; H-264 to L-426; K-265 to L-426; G-266 to L-426; T-267 to L-426; V-268 to L-426; V-269 to L-426; L-270 to L-426; C-271 to L-426; P-272 to L-426; Q-273 to L-426; T-274 to L-426; G-275 to L-426; V-276 to L-426; P-277 to L-426; F-278 to L-426; P-279 to L-426; L-280 to L-426; D-281 to L-426; N-282 to L-426; N-283 to L-426; K-284 to L-426; S-285 to L-426; K-286 to L-426; P-287 to L-426; G-288 to L-426; G-289 to L-426; W-290 to L-426; L-291 to L-426; P-292 to L-426; L-293 to L-426; L-294 to L-426; L-295 to L-426; L-296 to L-426; S-297 to L-426; L-298 to L-426; L-299 to L-426; V-300 to L-426; A-301 to L-426; T-302 to L-426; W-303 to L-426; V-304 to L-426; L-305 to L-426; V-306 to L-426; A-307 to L-426; G-308 to L-426; I-309 to L-426; Y-310 to L-426; L-311 to L-426; M-312 to L-426; W-313 to L-426; R-314 to L-426; H-315 to L-426; E-316 to L-426; R-317 to L-426; I-318 to L-426; K-319 to L-426; K-320 to L-426; T-321 to L-426; S-322 to L-426; F-323 to L-426; S-324 to L-426; T-325 to L-426; T-326 to L-426; T-327 to L-426; L-328 to L-426; L-329 to L-426; P-330 to L-426; P-331 to L-426; I-332 to L-426; K-333 to L-426; V-334 to L-426; L-335 to L-426; V-336 to L-426; V-337 to L-426; Y-333 to L-426; P-339 to L-426; S-340 to L-426; E-341 to L-426; I-342 to L-426; C-343 to L-426; F-344 to L-426; H-345 to L-426; H-346 to L-426; T-347 to L-426; I-348 to L-426; C-349 to L-426; Y-350 to L-426; F-351 to L-426; T-352 to L-426; E-353 to L-426; F-354 to L-426; L-355 to L-426; Q-356 to L-426; N-357 to L-426; H-358 to L-426; C-359 to L-426; R-360 to L-426; S-361 to L-426; E-362 to L-426; V-363 to L-426; I-364 to L-426; L-365 to L-426; E-366 to L-426; K-367 to L-426; W-368 to L-426; Q-369 to L-426; K-370 to L-426; K-371 to L-426; K-372 to L-426; I-373 to L-426; A-374 to L-426; E-375 to L-426; M-376 to L-426; G-377 to L-426; P-378 to L-426; V-379 to L-426; Q-380 to L-426; W-381 to L-426; L-382 to L-426; A-383 to L-426; T-384 to L-426; Q-385 to L-426; K-386 to L-426; K-367 to L-426; A-388 to L-426;

A-389 to L-426; D-390 to L-426; K-391 to L-426; V-392 to L-426; V-393 to L-426; F-394 to L-426; L-395 to L-426; L-396 to L-426; S-397 to L-426; N-398 to L-426; D-399 to L-426; V-400 to L-426; N-401 to L-426; S-402 to L-426; V-403 to L-426; C-404 to L-426; D-405 to L-426; G-406 to L-426; T-407 to L-426; C-408 to L-426; G-409 to L-426; K-410 to L-426; S-411 to L-426; E-412 to L-426; G-413 to L-426; S-414 to L-426; P-415 to L-426; S-416 to L-426; E-417 to L-426; N-418 to L-426; S-419 to L-426; Q-420 to L-426; and D-421 to L-426 of the IL17RLP amino acid sequence shown in FIGS. 1A, 1B, and 1C (which is identical to the sequence shown as SEQ ID NO:2, with the exception that the amino acid residues in FIGS. 1A, 1B, and 1C are numbered consecutively from 1 through 426 from the N-terminus to the C-terminus, while the amino acid residues in SEQ ID NO:2 are numbered consecutively from −19 through 407 to reflect the position of the predicted signal peptide). Polypeptides encoded by these polynucleotides are also encompassed by the invention.

Also as mentioned above, even if deletion of one or more amino acids from the C-terminus of a protein results in modification of loss of one or more biological functions of the protein, other biological activities may still be retained. Thus, the ability of the shortened IL17RLP mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that a IL17RLP mutein with a large number of deleted C-terminal amino acid residues may retain some biological or immungenic activities. In fact, peptides composed of as few as six IL17RLP amino acid residues may often evoke an immune response.

Accordingly, the present invention further provides polypeptides having one or more residues deleted from the carboxy terminus of the amino acid sequence of the IL17RLP shown in SEQ ID NO:2, up to the leucine residue at position number 6, and polynucleotides encoding such polypeptides. In particular, the present invention provides polypeptides comprising the amino acid sequence of residues 1–$m^2$ of SEQ ID NO:2, where $m^2$ is an integer in the range of 6 to 426, and 6 is the position of the first residue from the C-terminus of the complete IL17RLP polypeptide believed to be required for at least immunogenic activity of the IL17RLP protein.

More in particular, the invention provides polynucleotides encoding polypeptides comprising, or alternatively consisting of, the amino acid sequence of residues M-1 to C-425; M-1 to P-424; M-1 to S-423; M-1 to S-422; M-1 to D-421; M-1 to Q-420; M-1 to S-419; M-1 to N-418; M-1 to E-417; M-1 to S-416; M-1 to P-415; M-1 to S-414; M-1 to G-413; M-1 to E-412; M-1 to S-411; M-1 to K-410; M-1 to G-409; M-1 to C-408; M-1 to T-407; M-1 to G-406; M-1 to D-405; M-1 to C-404; M-1 to V-403; M-1 to S-402; M-1 to N-401; M-1 to V-400; M-1 to D-399; M-1 to N-398; M-1 to S-397; M-1 to L-396; M-1 to L-395; M-1 to F-394; M-1 to V-393; M-1 to V-392; M-1 to K-391; M-1 to D-390; M-1 to A-389; M-1 to A-388; M-1 to K-387; M-1 to K-386; M-1 to Q-385; M-1 to T-384; M-1 to A-383; M-1 to L-382; M-1 to W-381; M-1 to Q-380; M-1 to V-379; M-1 to P-378; M-1 to G-377; M-1 to M-376; M-1 to E-375; M-1 to A-374; M-1 to I-373; M-1 to K-372; M-1 to K-371; M-1 to K-370; M-1 to Q-369; M-1 to W-368; M-1 to K-367; M-1 to E-366; M-1 to L-365; M-1 to I-364; M-1 to V-363; M-1 to E-362; M-1 to S-361; M-1 to R-360; M-1 to C-359; M-1 to H-358; M-1 to N-357; M-1 to Q-356; M-1 to L-355; M-1 to F-354; M-1 to E-353; M-1 to T-352; M-1 to F-351; M-1 to Y-350; M-1 to C-349; M-1 to I-348; M-1 to T-347; M-1 to H-346; M-1 to H-345; M-1 to F-344; M-1 to C-343; M-1 to I-342; M-1 to E-341; M-1 to S-340; M-1 to P-339; M-1 to Y-338; M-1 to V-337; M-1 to V-336; M-1 to L-335; M-1 to V-334; M-1 to K-333; M-1 to I-332; M-1 to P-331; M-1 to P-330; M-1 to L-329; M-1 to L-328; M-1 to T-327; M-1 to T-326; M-1 to T-325; M-1 to S-324; M-1 to F-323; M-1 to S-322; M-1 to T-321; M-1 to K-320; M-1 to K-319; M-1 to I-318; M-1 to R-317; M-1 to E-316; M-1 to H-315; M-1 to R-314; M-1 to W-313; M-1 to M-312; M-1 to L-311; M-1 to Y-310; M-1 to I-309; M-1 to G-308; M-1 to A-307; M-1 to V-306; M-1 to L-305; M-1 to V-304; M-1 to W-303; M-1 to T-302; M-1 to A-301; M-1 to V-300; M-1 to L-299; M-1 to L-298; M-1 to S-297; M-1 to L-296; M-1 to L-295; M-1 to L-294; M-1 to L-293; M-1 to P-292; M-1 to L-291; M-1 to W-290; M-1 to G-289; M-1 to G-288; M-1 to P-287; M-1 to K-286; M-1 to S-285; M-1 to K-284; M-1 to N-283; M-1 to N-282; M-1 to D-281; M-1 to L-280; M-1 to P-279; M-1 to F-278; M-1 to P-277; M-1 to V-276; M-1 to G-275; M-1 to T-274; M-1 to Q-273; M-1 to P-272; M-1 to C-271; M-1 to L-270; M-1 to V-269; M-1 to V-268; M-1 to T-267; M-1 to G-266; M-1 to K-265; M-1 to H-264; M-1 to R-263; M-1 to I-262; M-1 to C-261; M-1 to D-260; M-1 to S-259; M-1 to G-258; M-1 to C-257; M-1 to T-256; M-1 to P-255; M-1 to F-254; M-1 to Y-253; M-1 to P-252; M-1 to T-251; M-1 to L-250; M-1 to Q-249; M-1 to V-248; M-1 to T-247; M-1 to A-246; M-1 to G-245; M-1 to E-244; M-1 to Q -243; M-1 to D-242; M-1 to 0–241; M-1 to T-240; M-1 to V-239; M-1 to P-238; M-1 to I-237; M-1 to V-236; M-1 to V-235; M-1 to S-234; M-1 to A-233; M-1 to R-232; M-1 to T-231; M-1 to Q-230; M-1 to K-229; M-1 to K-288; M-1 to Q-227; M-1 to H-226; M-1 to P-225; M-1 to E-224; M-1 to F-223; M-1 to V-222; M-1 to Q-221; M-1 to S-220; M-1 to F-219; M-1 to G-218; M-1 to I-217; M-1 to I-216; M-1 to T-215; M-1 to S-214; M-1 to H-213; M-1 to Q-212; M-1 to I-211; M-1 to L-210; M-1 to A-209; M-1 to M-208; M-1 to Y-207; M-1 to R-206; M-1 to N-205; M-1 to G-204; M-1 to L-203; M-1 to P-202; M-1 to T-201; M-1 to T-200; M-1 to T-199; M-1 to F-198; M-1 to N-197; M-1 to V-196; M-1 to E-195; M-1 to V-194; M-1 to T-193; M-1 to E-192; M-1 to E-191; M-1 to N-190; M-1 to K-189; M-1 to K-188; M-1 to C-187; M-1 to A-186; M-1 to T-185; M-1 to I-184; M-1 to N-183; M-1 to P-182; M-1 to D-181; M-1 to W-180; M-1 to L-179; M-1 to S-178; M-1 to G-177; M-1 to A-176; M-1 to K-175; M-1 to V-174; M-1 to C-173; M-1 to K-172; M-1 to K-171; M-1 to K-170; M-1 to Y-169; M-1 to K-168; M-1 to M-167; M-1 to I-166; M-1 to H-165; M-1 to D-164; M-1 to L-163; M-1 to C-162; M-1 to G-161; M-1 to P-160; M-1 to S-159; M-1 to T-158; M-1 to F-157; M-1 to N-156; M-1 to V-155; M-1 to S-154; M-1 to M-153; M-1 to S-152; M-1 to P-151; M-1 to G-150; M-1 to D-149; M-1 to E-148; M-1 to N-147; M-1 to M-146; M-1 to N-145; M-1 to A-144; M-1 to N-143; M-1 to P-142; M-1 to I-141; M-1 to N-140; M-1 to H-139; M-1 to A-138; M-1 to G-137; M-1 to I-136; M-1 to F-135; M-1 to Y-134; M-1 to V-133; M-1 to T-132; M-1 to N-131; M-1 to L-130; M-1 to E-129; M-1 to V-128; M-1 to P-127; M-1 to F-126; M-1 to G-125; M-1 to I-124; M-1 to Y-123; M-1 to S-122; M-1 to F-121; M-1 to T-120; M-1 to W-119; M-1 to K-118; M-1 to G-117; M-1 to G-116; M-1 to S-115; M-1 to P-114; M-1 to R-113; M-1 to T-112; M-1 to Q-111; M-1 to T-110; M-1 to Q-109; M-1 to F-108; M-1 to A-107; M-1 to E-106; M-1 to T-105; M-1 to Y-104; M-1 to N-103; M-1 to C-102; M-1 to R-101; M-1 to V-100; M-1 to C-99; M-1 to S-98; M-1 to Y-97; M-1 to S-96; M-1 to Q-95; M-1 to F-94; M-1 to N-93; M-1 to S-92; M-1 to K-91; M-1 to G-90; M-1 to T-89; M-1 to V-88; M-1 to C-87; M-1 to I-86; M-1 to K-85; M-1 to T-84; M-1 to A-83; M-1 to K-82; M-1 to L-81; M-1 to L-80; M-1 to R-79; M-1 to I-78; M-1 to S-77; M-1 to A-76; M-1 to D-75; M-1 to A-74; M-1 to R-73; M-1 to L-72; M-1 to V-71; M-1 to W-70; M-1 to S-69; M-1 to V-68; M-1 to N-67; M-1 to M-66; M-1 to L-65; M-1 to I-64; M-1 to S-63; M-1 to Y-62; M-1 to D-61; M-1 to G-60; M-1 to T-59; M-1 to A-58; M-1 to V-57; M-1 to S-56; M-1 to T-55; M-1 to T-54; M-1 to V-53; M-1 to P-52; M-1 to E-51; M-1 to V-50; M-1 to R-49; M-1 to L-48; M-1 to D-47; M-1 to R-46; M-1 to L-45; M-1 to D-44; M-1 to G-43; M-1 to P-42; M-1 to I-41; M-1 to L-40; M-1 to D-39; M-1 to H-38; M-1 to Q-37; M-1 to L-36; M-1 to M-35; M-1 to W-34; M-1 to E-33; M-1 to P-32; M-1 to S-31; M-1 to P-30; M-1 to G-29; M-1 to T-28; M-1 to E-27; M-1 to S-26; M-1 to G-25; M-1 to C-24; M-I to Q-23; M-1 to V-22; M-1 to T-21; M-1 to P-20; M-1 to E-19; M-1 to R-18; M-1 to P-17; M-1 to V-16; M-1 to A-15; M-1 to S-14; M-1 to R-13; M-1 to C-12; M-1 to L-1 l; M-1 to A-10; M-1 to A-9; M-1 to L-8; M-1 to S-7; and M-1 to L-6 of the sequence of the IL17RLP sequence shown in FIGS. 1A, 1B, and 1C (which is identical to the sequence shown as SEQ ID NO:2, with the exception that the amino acid residues in FIGS. 1A, 1B, and 1C are numbered consecutively from 1 through 426 from the N-terminus to the C-terminus, while the amino acid residues in SEQ ID NO:2 are numbered consecutively from −19 through 407 to reflect the position of the predicted signal peptide). Polypeptides encoded by these polynucleotides are also encompassed by the invention.

The invention also provides polypeptides having one or more amino acids deleted from both the amino and the carboxyl termini of an IL17RLP polypeptide, which may be described generally as having residues $n^2$–$m^2$ of FIGS. 1A, 1B, and 1C (SEQ ID NO:2), where $n^2$ and $m^2$ are integers as described above.

Also as mentioned above, even if deletion of one or more amino acids from the N-terminus of a protein results in modification of loss of one or more biological functions of the protein, other biological activities may still be retained. Thus, the ability of the shortened extracellular domain of the IL17RLP mutein to induce and/or bind to antibodies which recognize the extracellular domain of the IL17RLP protein generally will be retained when less than the majority of the residues of the extracellular domain of the IL17RLP protein are removed from the N-terminus. Whether a particular polypeptide lacking N-terminal residues of an extracellular domain of the IL17RLP protein retains such immunologic activities can readily be determined by routine methods described herein and otherwise known in the art. It is not unlikely that a IL17RLP mutein with a large number of deleted N-terminal amino acid residues may retain some biological or immungenic activities. In fact, peptides composed of as few as six amino acid residues of the extracellular domain of the IL17RLP protein may often evoke an immune response.

Accordingly, the present invention further provides polypeptides having one or more residues deleted from the amino terminus of the extracellular domain of the IL17RLP amino acid sequence shown in SEQ ID NO:2, up to the aspartic acid residue at position number 421 and polynucleotides encoding such polypeptides. In particular, the present invention provides polypeptides comprising the amino acid sequence of residues $n^3$–426 of FIGS. 1A, 1B, and 1C (SEQ ID NO:2), where $n^3$ is an integer in the range of 2 to 421, and 422 is the position of the first residue from the N-terminus of the complete IL17RLP polypeptide believed to be required for at least immunogenic activity of the IL17RLP protein.

More in particular, the invention provides polynucleotides encoding polypeptides comprising, or alternatively consisting of, the amino acid sequence of residues of A-15 to W-290; V-16 to W-290; P-17 to W-290; R-18 to W-290; E-19 to W-290; P-20 to W-290; T-21 to W-290; V-22 to W-290; Q-23 to W-290; C-24 to W-290; G-25 to W-290; S-26 to W-290; E-27 to W-290; T-28 to W-290; G-29 to W-290; P-30 to W-290; S-31 to W-290; P-32 to W-290; E-33 to W-290; W-34 to W-290; M-35 to W-290; L-36 to W-290; Q-37 to W-290; H-38 to W-290; D-39 to W-290; L-40 to W-290; I-41 to W-290; P-42 to W-290; G-43 to W-290; D-44 to W-290; L-45 to W-290; R-46 to W-290; D-47 to W-290; L-48 to W-290; R-49 to W-290; V-50 to W-290; E-51 to W-290; P-52 to W-290; V-53 to W-290; T-54 to W-290; T-55 to W-290; S-56 to W-290; V-57 to W-290; A-58 to W-290; T-59 to W-290; G-60 to W-290; D-61 to W-290; Y-62 to W-290; S-63 to W-290; I-64 to W-290; L-65 to W-290; M-66 to W-290; N-67 to W-290; V-68 to W-290; S-69 to W-290; W-70 to W-290; V-71 to W-290; L-72 to W-290; R-73 to W-290; A-74 to W-290; D-75 to W-290; A-76 to W-290; S-77 to W-290; I-78 to W-290; R-79 to W-290; L-80 to W-290; L-81 to W-290; K-82 to W-290; A-83 to W-290; T-84 to W-290; K-85 to W-290; I-86 to W-290; C-87 to W-290; V-88 to W-290; T-89 to W-290; G-90 to W-290; K-91 to W-290; S-92 to W-290; N-93 to W-290; F-94 to W-290; Q-95 to W-290; S-96 to W-290; Y-97 to W-290; S-98 to W-290; C-99 to W-290; V-100 to W-290; R-101 to W-290; C-102 to W-290; N-103 to W-290; Y-104 to W-290; T-105 to W-290; E-106 to W-290; A-107 to W-290; F-108 to W-290; Q-109 to W-290; T-110 to W-290; Q-111 to W-290; T-112 to W-290; R-113 to W-290; P-114 to W-290; S-115 to W-290; G-116 to W-290; G-117 to W-290; K-118 to W-290; W-119 to W-290; T-120 to W-290; F-121 to W-290; S-122 to W-290; Y-123 to W-290; I-124 to W-290; G-125 to W-290; F-126 to W-290; P-127 to W-290; V-128 to W-290; E-129 to W-290; L-130 to W-290; N-131 to W-290; T-132 to W-290; V-133 to W-290; Y-134 to W-290; F-135 to W-290; I-136 to W-290; G-137 to W-290; A-138 to W-290; H-139 to W-290; N-140 to W-290; I-141 to W-290; P-142 to W-290; N-143 to W-290; A-144 to W-290; N-145 to W-290; M-146 to W-290; N-147 to W-290; E-148 to W-290; D-149 to W-290; G-150 to W-290; P-151 to W-290; S-152 to W-290; M-153 to W-290; S-154 to W-290; V-155 to W-290; N-156 to W-290; F-157 to W-290; T-158 to W-290; S-159 to W-290; P-160 to W-290; G-161 to W-290; C-162 to W-290; L-163 to W-290; D-164 to W-290; H-165 to W-290; I-166 to W-290; M-167 to W-290; K-168 to W-290; Y-169 to W-290; K-170 to W-290; K-171 to W-290; K-172 to W-290; C-173 to W-290; V-174 to W-290; K-175 to W-290; A-176 to W-290; G-177 to W-290; S-178 to W-290; L-179 to W-290; W-180 to W-290; D-181 to W-290; P-182 to W-290; N-183 to W-290; I-184 to W-290; T-185 to W-290; A-186 to W-290; C-187 to W-290; K-188 to W-290; K-189 to W-290; N-190 to W-290; E-191 to W-290; E-192 to W-290; T-193 to W-290; V-194 to W-290; E-195 to W-290; V-196 to W-290; N-197 to W-290; F-198 to W-290; T-199 to W-290; T-200 to W-290; T-201 to W-290; P-202 to W-290; L-203 to W-290; G-204 to W-290; N-205 to W-290; R-206 to W-290; Y-207 to W-290; M-208 to W-290; A-209 to W-290; L-210 to W-290; I-211 to W-290; Q-212 to W-290; H-213 to W-290; S-214 to W-290; T-215 to W-290; I-216 to W-290; I-217 to W-290; G-218 to W-290; F-219 to W-290; S-220 to W-290; Q-221 to W-290; V-222 to W-290; F-223 to W-290; E-224 to W-290; P-225 to W-290; H-226 to W-290; Q-227 to W-290; K-228 to W-290; K-229 to W-290; Q-230 to W-290; T-231 to W-290; R-232 to W-290; A-233 to W-290; S-234 to W-290; V-235 to W-290; V-236 to W-290; I-237 to W-290; P-238 to W-290; V-239 to W-290; T-240 to W-290; G-241 to W-290; D-242 to W-290; S-243 to W-290; E-244 to W-290; G-245 to W-290; A-246 to W-290; T-247 to W-290; V-248 to W-290; Q-249 to W-290; L-250 to W-290; T-251 to W-290; P-252 to W-290; Y-253 to W-290; F-254 to W-290; P-255 to W-290; T-256 to W-290; C-257 to W-290; G-258 to W-290; S-259 to W-290; D-260 to W-290; C-261 to W-290; I-262 to W-290; R-263 to W-290; H-264 to W-290; K-265 to W-290; G-266 to W-290; T-267 to W-290; V-268 to W-290; V-269 to W-290; L-270 to W-290; C-271 to W-290; P-272 to W-290; Q-273 to W-290; T-274 to W-290; G-275 to W-290; V-276 to W-290; P-277 to W-290; F-278 to W-290; P-279 to W-290; L-280 to W-290; D-281 to W-290; N-282 to W-290; N-283 to W-290; K-284 to W-290; and S-285 to W-290 of the IL17RLP amino acid sequence shown in FIGS. 1A, 1B, and 1C (which is identical to the sequence shown as SEQ ID NO:2, with the exception that the amino acid residues in FIGS. 1A, 1B, and 1C are numbered consecutively from 1 through 426 from the N-terminus to the C-terminus, while the amino acid residues in SEQ ID NO:2 are numbered consecutively from −19 through 407 to reflect the position of the predicted signal peptide). Polypeptides encoded by these polynucleotides are also encompassed by the invention.

Also as mentioned above, even if deletion of one or more amino acids from the C-terminus of the extracellular domain of an IL17RLP protein results in modification of loss of one or more biological functions of the protein, other biological activities may still be retained. Thus, the ability of the shortened extracellular domain of an IL17RLP mutein to induce and/or bind to antibodies which recognize the extracellular domain of an IL17RLP protein generally will be retained when less than the majority of the residues of the extracellular domain of an IL17RLP protein are removed from the C-terminus. Whether a particular polypeptide lacking C-terminal residues of a extracellular domain of an IL17RLP protein retains such immunologic activities can readily be determined by routine methods described herein and otherwise known in the art. It is not unlikely that an extracellular domain of an IL17RLP mutein with a large number of deleted C-terminal amino acid residues may retain some biological or immungenic activities. In fact, peptides composed of as few as six extracellular IL17RLP amino acid residues may often evoke an immune response.

Accordingly, the present invention further provides polypeptides having one or more residues deleted from the carboxy terminus of the amino acid sequence of the extracellular domain of the IL17RLP shown in SEQ ID NO:2, up to the leucine residue at position number 6, and polynucleotides encoding such polypeptides. In particular, the present invention provides polypeptides comprising the amino acid sequence of residues 1–m$^3$ of SEQ ID NO:2, where m$^3$ is an integer in the range of 6 to 426, and 6 is the position of the first residue from the C-terminus of the complete IL17RLP polypeptide believed to be required for at least immunogenic activity of the IL17RLP protein.

More in particular, the invention provides polynucleotides encoding polypeptides comprising, or alternatively consisting of, the amino acid sequence of residues A-15 to W-290; A-15 to G-289; A-15 to G-288; A-15 to P-287; A-15 to K-286; A-15 to S-285; A-15 to K-284; A-15 to N-283; A-15 to N-282; A-15 to D-281; A-15 to L-280; A-15 to P-279; A-15 to F-278; A-15 to P-277; A-15 to V-276; A-15 to G-275; A-15 to T-274; A-15 to Q-273; A-15 to P-272; A-15 to C-271; A-15 to L-270; A-15 to V-269; A-15 to V-268; A-15 to T-267; A-15 to G-266; A-15 to K-265; A-15 to H-264; A-15 to R-263; A-15 to I-262; A-15 to C-261; A-15 to D-260; A-15 to S-259; A-15 to G-258; A-15 to C-257; A-15 to T-256; A-15 to P-255; A-15 to F-254; A-15 to Y-253; A-15 to P-252; A-15 to T-251; A-15 to L-250; A-15 to Q-249; A-15 to V-248; A-15 to T-247; A-15 to A-246; A-15 to G-245; A-15 to E-244; A-15 to S-243; A-15 to D-242; A-15 to G-241; A-15 to T-240; A-15 to V-239; A-15 to P-238; A-15 to I-237; A-15 to V-236; A-15 to V-235; A-15 to S-234; A-15 to A-233; A-15 to R-232; A-15 to T-231; A-15 to Q-230; A-15 to K-229; A-15 to K-228; A-15 to Q-227; A-15 to H-226; A-15 to P-225; A-15 to E-224; A-15 to F-223; A-15 to V-222; A-15 to Q-221; A-15 to S-220; A-15 to F-219; A-15 to G-218; A-15 to I-217; A-15 to I-216; A-15 to T-215; A-15 to S-214; A-15 to H-213; A-15 to Q-212; A-15 to I-211; A-15 to L-210; A-15 to A-209; A-15 to M-208; A-15 to Y-207; A-15 to R-206; A-15 to N-205; A-15 to G-204; A-15 to L-203; A-15 to P-202; A-15 to T-201; A-15 to T-200; A-15 to T-199; A-15 to F-198; A-15 to N-197; A-15 to V-196; A-15 to E-195; A-15 to V-194; A-15 to T-193; A-15 to E-192; A-15 to E-191; A-15 to N-190; A-15 to K-189; A-15 to K-188; A-15 to C-187; A-15 to A-186; A-15 to T-185; A-15 to I-184; A-15 to N-183; A-15 to P-182; A-15 to D-181; A-15 to W-180; A-15 to L-179; A-15 to S-178; A-15 to G-177; A-15 to A-176; A-15 to K-175; A-15 to V-174; A-15 to C-173; A-15 to K-172; A-15 to K-171; A-15 to K-170; A-15 to Y-169; A-15 to K-168; A-15 to A-1567; A-15 to I-166; A-15 to H-165; A-15 to D-164; A-15 to L-163; A-15 to C-162; A-15 to G-161; A-15 to P-160; A-15 to S-159; A-15 to T-158; A-15 to F-157; A-15 to N-156; A-15 to V-155; A-15 to S-154; A-15 to A-1553; A-15 to S-152; A-15 to P-151; A-15 to G-150; A-15 to D-149; A-15 to E-148; A-15 to N-147; A-15 to A-1546; A-15 to N-145; A-15 to A-144; A-15 to N-143; A-15 to P-142; A-15 to I-141; A-15 to N-140; A-15 to H-139; A-15 to A-138; A-15 to G-137; A-15 to I-136; A-15 to F-135; A-15 to Y-134; A-15 to V-133; A-15 to T-132; A-15 to N-131; A-15 to L-130; A-15 to E-129; A-15 to V-128; A-15 to P-127; A-15 to F-126; A-15 to G-125; A-15 to I-124; A-15 to Y-123; A-15 to S-122; A-15 to F-121; A-15 to T-120; A-15 to W-119; A-15 to K-118; A-15 to G-117; A-15 to G-116; A-15 to S-115; A-15 to P-114; A-15 to R-113; A-15 to T-112; A-15 to Q-111; A-15 to T-110; A-15 to Q-109; A-15 to F-108; A-15 to A-107; A-15 to E-106; A-15 to T-105; A-15 to Y-104; A-15 to N-103; A-15 to C-102; A-15 to R-101; A-15 to V-100; A-15 to C-99; A-15 to S-98; A-15 to Y-97; A-15 to S-96; A-15 to Q-95; A-15 to F-94; A-15 to N-93; A-15 to S-92; A-15 to K-91; A-15 to G-90; A-15 to T-89; A-15 to V-88; A-15 to C-87; A-15 to I-86; A-15 to K-85; A-15 to T-84; A-15 to A-83; A-15 to K-82; A-15 to L-81; A-15 to L-80; A-15 to R-79; A-15 to I-78; A-15 to S-77; A-15 to A-76; A-15 to D-75; A-15 to A-74; A-15 to R-73; A-15 to L-72; A-15 to V-71; A-15 to W-70; A-15 to S-69; A-15 to V-68; A-15 to N-67; A-15 to M-66; A-15 to L-65; A-15 to I-64; A-15 to S-63; A-15 to Y-62; A-15 to D-61; A-15 to G-60; A-15 to T-59; A-15 to A-58; A-15 to V-57; A-15 to S-56; A-15 to T-55; A-15 to T-54; A-15 to V-53; A-15 to P-52; A-15 to E-51; A-15 to V-50; A-15 to R-49; A-15 to L-48; A-15 to D-47; A-15 to R-46; A-15 to L-45; A-15 to D-44; A-15 to G-43; A-15 to P-42; A-15 to I-41; A-15 to L-40; A-15 to D-39; A-15 to H-38; A-15 to Q-37; A-15 to L-36; A-15 to M-35; A-15 to W-34; A-15 to E-33; A-15 to P-32; A-15 to S-31; A-15 to P-30; A-15 to G-29; A-15 to T-28; A-15 to E-27; A-15 to S-26; A-15 to G-25; A-15 to C-24; A-15 to Q-23; A-15 to V-22; A-15 to T-21; and A-15 to P-20 of the sequence of the IL17RLP sequence shown in FIGS. 1A, 1B, and 1C (which is identical to the sequence shown as SEQ ID NO:2, with the exception that the amino acid residues in FIGS. 1A, 1B, and 1C are numbered consecutively from 1 through 426 from the N-terminus to the C-terminus, while the amino acid residues in SEQ ID NO:2 are numbered consecutively from −19 through 407 to reflect the position of the predicted signal peptide). Polypeptides encoded by these polynucleotides are also encompassed by the invention.

The invention also provides polypeptides having one or more amino acids deleted from both the amino and the carboxyl termini of an extracellular domain of the IL17RLP polypeptide, which may be described generally as having residues $n^3$–$m^3$ of FIGS. 1A, 1B, and 1C (SEQ ID NO:2), where $n^3$ and $m^3$ are integers as described above.

One specific embodiment of the present invention includes polypeptide fragments of the amino acid sequence set forth in SEQ ID NO:2 which may be used, for example, to generate monoclonal antibodies as described herein below. Particular examples of such polypeptides include polypeptides comprising, or alternatively consisting of, the amino acid sequences PREPTVQCGSETGPSPE (SEQ ID NO:14) (i.e., amino acid positions Pro-17 to Glu-33 of SEQ ID NO:2); LDHIMKYKKK(SEQ ID NO:15) (i.e., amino acid positions Leu-163 to Lys-173 of SEQ ID NO:2); and KKNEETVEVN (SEQ ID NO:16) (i.e., amino acid positions Lys-188 to Asn-197 of SEQ ID NO:2).

In addition to terminal deletion forms of the protein discussed above, it also will be recognized by one of ordinary skill in the art that some amino acid sequences of the IL17RLP polypeptide can be varied without significant effect of the structure or function of the protein. If such differences in sequence are contemplated, it should be remembered that there will be critical areas on the protein which determine activity.

Thus, the invention further includes variations of the IL17RLP polypeptide which show substantial IL17RLP polypeptide activity or which include regions of IL17RLP protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided wherein the authors indicate that there are two main approaches for studying the tolerance of an amino acid sequence to change (Bowie, J. U., et al., *Science* 247:1306–1310 (1990)). The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described by Bowie and coworkers (supra) and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the extracellular domain of the polypeptide is fused with another compound, such as a compound to increase the half-life of the polypeptide (for example, polyethylene glycol), or (v) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the IL17RLP of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table II).

TABLE II

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Embodiments of the invention are directed to polypeptides which comprise the amino acid sequence of an IL17RLP polypeptide described herein, but having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions, when compared with the follistatin-3 polynucleotide sequence described herein. Of course, in order of ever-increasing preference, it is highly preferable for a peptide or polypeptide to have an amino acid sequence which comprises the amino acid sequence of an IL17RLP polypeptide, which contains at least one, but not more than 20, 10, 9, 8, 7, 6, 5, 4, 3, 2 or 1 conservative amino acid substitutions.

In further specific embodiments, the number of substitutions, additions or deletions in the amino acid sequence of FIGS. 1A, 1B, and 1C (SEQ ID NO:2), a polypeptide sequence encoded by the deposited clones, and/or any of the polypeptide fragments described herein is 150, 100, 75, 70, 60, 50, 40, 35, 30, 25, 20, 15, 10, 9, 8, 7, 6, 5, 4, 3, 2, 1 or 250–150, 200–50, 150–50, 100–50, 50–20, 30–20, 20–15, 20–10, 15–10, 10–1, 5–10, 1–5, 1–3 or 1–2.

To improve or alter the characteristics of IL17RLP polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Thus, the invention also encompasses IL17RLP derivatives and analogs that have one or more amino acid residues deleted, added, or substituted to generate IL17RLP polypeptides that are better suited for expression, scale up, etc., in the host cells chosen. For example, cysteine residues can be deleted or substituted with another amino acid residue in order to eliminate disulfide bridges, PKC phosphorylation sites, CK2 phosphorylation sites, cAMP- and cGMP-dependent protein kinase phosphorylation sites, myristolation, and/or N-linked glycosylation sites can be altered or eliminated to acheive an alterred function or expression pattern of the polypeptide (for example, a mutated N-linked glycosylation site may alter the expression of a homogeneous product that is more easily recovered and purified from yeast hosts which are known to hyperglycosylate N-linked sites). To this end, a variety of amino acid substitutions at one or both of the first or third amino acid positions on any one or more of the disulfide bridge cysteines, PKC phosphorylation sites, CK2 phosphorylation sites, cAMP- and cGMP-dependent protein kinase phosphorylation sites, myristolation, and/or glycosylation recognition sequences in the IL17RLP polypeptides of the invention, and/or an amino acid deletion at the second position of any one or more recognition sequences will alter function or expression or prevent glycosylation of the IL17RLP polypeptide at the modified tripeptide sequence (see, e.g., Miyajima, A., et al., *EMBO J.* 5(6):1193–1197 (1986)).

Amino acids in the IL17RLP protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard, et al., *Clin. Exp. Immunol.* 2:331–340 (1967); Robbins, et al., *Diabetes* 36:838–845 (1987); Cleland, et al., *Crit. Rev. Therapeutic Drug Carrier Systems* 10:307–377 (1993)).

Replacement of amino acids can also change the selectivity of the binding of a ligand to cell surface receptors (for example, Ostade, et al., *Nature* 361:266–268 (1993)) describes certain mutations resulting in selective binding of TNF-alpha to only one of the two known types of TNF receptors. Sites that are critical for ligand-receptor binding can also be determined by structural analysis such as crystallization, nuclear magnetic resonance or photoaffinity labeling (Smith, et al., *J. Mol. Biol.* 224:899–904 (1992); de Vos, et al. *Science* 255:306–312 (1992)).

Since IL17RLP is a homologue of the murine IL-17 receptor protein, to modulate rather than completely eliminate biological activities of IL17RLP preferably mutations are made in sequences encoding amino acids in the IL17RLP conserved extracellular domain, i.e., in positions 1–271 of SEQ ID NO:2, more preferably in residues within this region which are not conserved in the murine IL-17 receptor protein. Also forming part of the present invention are isolated polynucleotides comprising nucleic acid sequences which encode the above IL17RLP mutants.

Amino acid regions of the IL17RLP sequence shown in SEQ ID NO:2 which are highly conserved when compared to the murine IL-17R polypeptide sequence shown as SEQ ID NO:3 (see FIG. 2) are attractive regions for targeted mutagenesis of the IL17RLP polypeptides of the invention. In fact, a number of conserved regions or domains have been set forth in FIGS. 1A, 1B, and 1C (labeled as Domains I–VIII). These domains are as follows: Domain I (i.e., Val-49 through Leu-62 of SEQ ID NO:2 (Val-68 through Leu-81 of FIGS. 1A, 1B, and 1C)); Domain II (Cys-154 through Thr-166 of SEQ ID NO:2 (i.e., Cys-173 through Thr-185 of FIGS. 1A, 1B, and 1C)); Domain III (Gln-202 through Gln-208 of SEQ ID NO:2 (i.e., Gln-221 through Gln-227 of FIGS. 1A, 1B, and 1C)); Domain IV (Asp-241 through Val-249 of SEQ ID NO:2 (i.e., Asp-260 through Val-268 of FIGS. 1A, 1B, and 1C)); Domain V (Thr-255 through Leu-261 of SEQ ID NO:2 (i.e., Thr-274 through Leu-280 of FIGS. 1A, 1B, and 1C)); Domain VI (Leu-310 through Tyr-319 of SEQ ID NO:2 (i.e., Leu-329 through Tyr-338 of FIGS. 1A, 1B, and 1C)); Domain VII (Cys-340 through Leu-346 of SEQ ID NO:2 (i.e., Cys-359 through Leu-365 of FIGS. 1A, 1B, and 1C)); and Domain VIII (Ile-354 through Gly-358 of SEQ ID NO:2 (i.e., Ile-373 through Gly-377 of FIGS. 1A, 1B, and 1C)).

In another embodiment of the invention, seven cysteine residues of IL17RLP are conserved with respect to the murine IL-17R polypeptide sequence shown in SEQ ID NO:3. Cysteine residues tend to play an important role in the structural conformation, and thus, the function of a polypeptide. As such, the seven conserved cysteine residues are also attractive residues for targeted mutagenesis of the IL17RLP polypeptides of the invention. The seven highly conserved cysteine residues of the IL17RLP shown in SEQ ID NO:2 of the present invention are as follows: Cys-5, Cys-80, Cys-143, Cys-154, Cys-238, Cys-242, and Cys-340 of SEQ ID NO:2 (which correspond exactly to Cys-24, Cys-99, Cys-162, Cys-173, Cys-257, Cys-261, and Cys-359 of FIGS. 1A, 1B, and 1C).

The polypeptides of the present invention are preferably provided in an isolated form, and preferably are substantially purified. A recombinantly produced version of the IL17RLP polypeptide can be substantially purified by the one-step method described by Smith and Johnson (*Gene* 67:31–40 (1988)). Polypeptides of the invention also can be purified from natural or recombinant sources using anti-IL17RLP antibodies of the invention in methods which are well known in the art of protein purification.

The invention further provides an isolated IL17RLP polypeptide comprising an amino acid sequence selected from the group consisting of: (a) the amino acid sequence of the full-length IL17RLP polypeptide having the complete amino acid sequence shown in SEQ ID NO:2 (i.e., positions −19 to 407 of SEQ ID NO:2); (b) the amino acid sequence of the full-length IL17RLP polypeptide having the complete amino acid sequence shown in SEQ ID NO:2 excepting the N-terminal methionine (i.e., positions −18 to 407 of SEQ ID NO:2); (c) the amino acid sequence of the mature IL17RLP polypeptide having the complete amino acid sequence shown in SEQ ID NO:2 (i.e., positions 1 to 407 of SEQ ID NO:2); (d) the amino acid sequence of the predicted extracellular domain of the IL17RLP polypeptide having the complete amino acid sequence shown in SEQ ID NO:2 (i.e., positions 1 to 271 of SEQ ID NO:2); (e) the amino acid sequence of a soluble IL17RLP polypeptide having the predicted extracellular and intracellular domains, but lacking the predicted transmembrane domain; (f) the complete amino acid sequence encoded by the human cDNA contained in the ATCC Deposit No. 209198; (g) the complete amino acid sequence excepting the N-terminal methionine encoded by the human cDNA contained in the ATCC Deposit No. 209198; (h) the complete amino acid sequence of the mature IL17RLP encoded by the human cDNA contained in the ATCC Deposit No. 209198, and; (i) the complete amino acid sequence of the extracellular domain of the IL17RLP encoded by the human cDNA contained in the ATCC Deposit No. 209198. The polypeptides of the present invention also include polypeptides having an amino acid sequence at least 80% identical, more preferably at least 90% identical, and still more preferably 95%, 96%, 97%, 98% or 99% identical to those described in (a), (b), (c), (d), (e), (f), (g), (h) or (i) above, as well as polypeptides having an amino acid sequence with at least 90% similarity, and more preferably at least 95% similarity, to those above.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited cDNA or to the polypeptide of SEQ ID NO:2, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of a IL17RLP polypeptide is intended that the amino acid sequence of the polypeptide is identical to the reference sequence except that the polypeptide sequence may include up to five amino acid alterations per each 100 amino acids of the reference amino acid of the IL17RLP polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A, 1B, and 1C (SEQ ID NO:2), the amino acid sequence encoded by deposited cDNA clone HAPOR40, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present application is also directed to proteins cotaining polypeptides at least 90%, 95%, 96%, 97%, 98% or 99% identical to the IL17RLP polypeptide sequence set forth herein as $n^1-m^1$, $n^2-m^2$, and/or $n^3-m^3$. In preferred embodiments, the application is directed to proteins containing polypeptides at least 90%, 95%, 96%, 97%, 98% or 99% identical to polypeptides having the amino acid sequence of the specific IL17RLP N- and C-terminal deletions recited herein. Polynucleotides encoding these polypeptides are also encompassed by the invention.

The invention also encompasses fusion proteins in which the full-length IL17RLP polypeptide or fragment, variant, derivative, or analog thereof is fused or joined to an unrelated protein. These fusion proteins can be routinely designed on the basis of the IL17RLP nucleotide and polypeptide sequences disclosed herein. For example, as one of skill in the art will appreciate, IL17RLP polypeptides and fragments (including epitope-bearing fragments) thereof described herein can be combined with parts of the constant domain of immunoglobulins (IgG), resulting in chimeric (fusion) polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker, et aL, *Nature* 331:84–86 (1988)). Fusion proteins that have a disulfide-linked dimeric structure due to the IgG part can also be more efficient in binding and neutralizing other molecules than the monomeric IL17RLP polypeptide or polypeptide fragments alone (Fountoulakis, et al., *J. Biochem.* 270:3958–3964 (1995)). Examples of IL17RLP fusion proteins that are encompassed by the invention include, but are not limited to, fusion of the IL17RLP polypeptide sequences to any amino acid sequence that allows the fusion proteins to be displayed on the cell surface (e.g. the IgG Fc domain); or fusions to an enzyme, fluorescent protein, or luminescent protein which provides a marker function.

As described in detail below, the polypeptides of the present invention can also be used to raise polyclonal and monoclonal antibodies, which are useful in assays for detecting IL17RLP protein expression as described below or as agonists and antagonists capable of enhancing or inhibiting IL17RLP protein function. Further, such polypeptides can be used in the yeast two-hybrid system to "capture" IL17RLP protein binding proteins which are also candidate agonists and antagonists according to the present invention. The yeast two hybrid system is described by Fields and Song (*Nature* 340:245–246 (1989)).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes (see, for instance, Geysen, et al., *Proc. Natl. Acad. Sci. USA* 81:3998–4002 (1983)).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein (see, for instance, Sutcliffe, J. G., et al., *Science* 219:660–666 (1983)). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention (see, for instance, Wilson, et al., *Cell* 37:767–778 (1984)).

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate IL17RLP-specific antibodies include: a polypeptide comprising amino acid residues from about Ser-14 to about Val-22 in SEQ ID NO:2, a polypeptide comprising amino acid residues from about Cys-24 to about Pro-32 in SEQ ID NO:2, a polypeptide comprising amino acid residues from about Ile-41 to about Arg-49 in SEQ ID NO:2, a polypeptide comprising amino acid residues from about Thr-89 to about Val-97 in SEQ ID NO:2, a polypeptide comprising amino acid residues from about Thr-110 to about Lys-118 in SEQ ID NO:2, a polypeptide comprising amino acid residues from about Ala-144 to about Ser-152 in SEQ ID NO:2, a polypeptide comprising amino acid residues from about Thr-240 to about Val-248 in SEQ ID NO:2, a polypeptide comprising amino acid residues from about Gly-258 to about Thr-267 in SEQ ID NO:2, a polypeptide comprising amino acid residues from about Leu-280 to about Gly-288 in SEQ ID NO:2, a polypeptide comprising amino acid residues from about Cys-404 to about Glu-412 in SEQ ID NO:2, a polypeptide comprising amino acid residues from about Pro-415 to about Ser-423 in SEQ ID NO:2, a polypeptide comprising amino acid residues from about Gly-409 to about Glu-417 in SEQ ID NO:2, and a polypeptide comprising amino acid residues from about Cys-404 to about Leu-426 in FIGS. 1A, 1B, and 1C (which is identical to the sequence shown in SEQ ID NO:2 with the exception of the numbering scheme as detailed above). These polypeptide fragments have been determined to bear antigenic epitopes of the IL17RLP protein by the analysis of the Jameson-Wolf antigenic index, as shown in FIG. 3, above.

The epitope-bearing peptides and polypeptides of the invention may be produced by any conventional means (see, for example, Houghten, R. A., et al., *Proc. Natl. Acad. Sci.*

USA 82:5131–5135 (1985); and U.S. Pat. No. 4,631,211 to Houghten, et al. (1986)).

Epitope-bearing peptides and polypeptides of the invention are used to induce antibodies according to methods well known in the art (see, for instance, Sutcliffe, et al., supra; Wilson, et al., supra; Chow, M., et al., *Proc. Natl. Acad. Sci. USA* 82:910–914; and Bittle, F. J., et al., *J. Gen. Virol.* 66:2347–2354 (1985)). Inmmunogenic epitope-bearing peptides of the invention, i.e., those parts of a protein that elicit an antibody response when the whole protein is the immunogen, are identified according to methods known in the art (see, for instance, Geysen, et al., supra). Further still, U.S. Pat. No. 5,194,392, issued to Geysen, describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092, issued to Geysen, describes a method of detecting or determining a sequence of monomers which is a topographical equivalent of a ligand which is complementary to the ligand binding site of a particular receptor of interest. Similarly, U.S. Pat. No. 5,480,971, issued to Houghten and colleagues, on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, IL17RLP polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker, et al., *Nature* 331:84–86 (1988)). Fusion proteins that have a disulfide-linked dimeric structure due to the IgG part can also be more efficient in binding and neutralizing other molecules than the monomeric IL17RLP protein or protein fragment alone (Fountoulakis, et al., *J. Biochem.* 270:3958–3964 (1995)).

The functional activity of IL17RLP polypeptides, and fragments, variants derivatives, and analogs thereof, can be assayed by various methods.

For example, in one embodiment where one is assaying for the ability to bind or compete with full-length IL17RLP polypeptide for binding to an anti-IL17RLP antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where an IL17RLP ligand is identified (e.g. IL-20), or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, Microbiol. Rev. 59:94–123. In another embodiment, physiological correlates of IL17RLP binding to its substrates (signal transduction) can be assayed.

In addition, assays described herein (see Examples 5–8 and otherwise known in the art may routinely be applied to measure the ability of IL17RLP polypeptides and fragments, variants derivatives and analogs thereof to elicit IL17RLP related biological activity (e.g., to act as an attractant for neutrophils in vitro or in vivo).

Other methods will be known to the skilled artisan and are within the scope of the invention.

The invention further provides for the proteins containing polypeptide sequences encoded by the polynucleotides of the invention.

The IL17RLP proteins, or fragments thereof, of the invention may be in monomers or multimers (i.e., dimers, trimers, tetramers, and higher multimers). Accordingly, the present invention relates to monomers and multimers of the IL17RLP proteins of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only IL17RLP proteins of the invention (including IL17RLP fragments, variants, and fusion proteins, as described herein). These homomers may contain IL17RLP proteins having identical or different polypeptide sequences. In a specific embodiment, a homomer of the invention is a multimer containing only IL17RLP proteins having an identical polypeptide sequence. In another specific embodiment, a homomer of the invention is a multimer containing IL17RLP proteins having different polypeptide sequences. In specific embodiments, the multimer of the invention is a homodimer (e.g., containing IL17RLP proteins having identical or different polypeptide sequences) or a homotrimer (e.g., containing IL17RLP proteins having identical or different polypeptide sequences). In additional embodiments, the homomeric multimer of the invention is at least a homodimer, at least a homotrimer, or at least a homotetramer.

As used herein, the term heteromer refers to a multimer containing heterologous proteins (i.e., proteins containing only polypeptide sequences that do not correspond to a polypeptide sequences encoded by the IL17RLP gene) in addition to the IL17RLP proteins of the invention. In a specific embodiment, the multimer of the invention is a heterodimer, a heterotrimer, or a heterotetramer. In additional embodiments, the homomeric multimer of the invention is at least a homodimer, at least a homotrimer, or at least a homotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the IL17RLP proteins of the invention. Such covalent associations may involve one or more amino acid residues contained in the polypeptide sequence of the polypeptide sequence recited in SEQ ID NO:2 and contained in the polypeptide encoded by the cDNA clone contained in ATCC Deposit No. 209198. In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in an IL17RLP fusion protein. In one example, covalent associations are between the heterologous sequence contained in a fusion protein of the invention (see, e.g., U.S. Pat. No. 5,478,925). In a specific example, the covalent associations are between the heterologous sequence contained in an IL17RLP-Fc fusion protein of the invention (as described herein).

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

In addition, proteins of the invention can be chemically synthesized using techniques known in the art (e.g., see Creighton, 1983, Proteins: Structures and Molecular Principles, W. H. Freeman & Co., N.Y., and Hunkapiller, M., et al., Nature 310:105–111 (1984)). For example, a peptide corresponding to a fragment of the IL17RLP polypeptides of the invention can be synthesized by use of a peptide synthesizer. Furthermore, if desired, nonclassical amino acids or chemical amino acid analogs can be introduced as a substitution or addition into the IL17RLP polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention additionally, encompasses IL17RLP polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$ acetylation, formylation, oxidation, reduction, metabolic synthesis in the presence of tunicamycin; etc.

Additional post-translational modifications encompassed by the invention include, for example, e.g., N-inked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of IL17RLP which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The proteins of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., nucleic acids of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety. Further, the contents of each of the documents recited in this paragraph is herein incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of IL17RLP polypeptides, studying conditions and/or disorders associated with aberrant IL17RLP expression, and in screening for compounds effective in ameliorating such conditions and/or disorders.

In further embodiments of the invention, cells that are genetically engineered to express the proteins of the invention, or alternatively, that are genetically engineered not to express the proteins of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Antibodies

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al., J. Immunol. 147:60–69 (1991); U.S. Pat. Nos. 5,573,920, 4,474,893, 5,601,819, 4,714,681, 4,925,648; Kostelny, S. A. et al, J. Immunol. 148:1547–1553 (1992).

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and FIGS. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., ANTIBODIES: A LABORATORY MANUAL, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. Monoclonal antibodies can be prepared using a wide of techniques known in the art including the use of hybridoma and recombinant technology. See, e.g., Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563–681 (Elsevier, N.Y., 1981) (said references incorporated by reference in their entireties).

Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al., J. Immunol. Methods 182:41–50 (1995); Ames, R. S. et al., J. Immunol. Methods 184:177–186 (1995); Kettleborough, C. A. et al., Eur. J. Immunol. 24:952–958 (1994); Persic, L. et al., Gene 187 9–18 (1997); Burton, D. R. et al., Advances in Immunology 57:191–280 (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al., BioTechniques 12(6):864–869 (1992); and Sawai, H. et al. AJRI 34:26–34 (1995); and Better, M. et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu, L. et al., PNAS 90:7995–7999 (1993); and Skerra, A. et al., Science 240:1038–1040 (1988). For some uses, including in vivo use of antibodies in humans and in vitro detection assays, it may be preferable to use chimeric, humanized, or human antibodies. Methods for producing chimeric antibodies are known in the art. See e.g., Morrison, Science 229:1202 (1985); Oi et al., BioTechniques 4:214 (1986); Gillies, S. D. et al., J. Immunol. Methods 125:191–202 (1989); and U.S. Pat. No. 5,807,715. Antibodies can be humanized using a variety of techniques including CDR-grafting (EP 0239 400; WO 91/09967; U.S. Pat. Nos. 5,530,101; and 5,585,089), veneering or resurfacing (EP 0 592 106; EP 0 519 596; Padlan E. A., Molecular Immunology 28(4/5):489–498 (1991); Studnicka G. M. et al., Protein Engineering 7(6): 805–814 (1994); Roguska M. A. et al., PNAS 91:969–973 (1994)), and chain shuffling (U.S. Pat. No. 5,565,332). Human antibodies can be made by a variety of methods known in the art including phage display methods described above. See also, U.S. Pat. Nos. 4,444,887, 4,716,111, 5,545, 806, and 5,814,318; and WO 98/46645 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al. (1994) Immunol. Lett. 39:91–99; U.S. Pat. No. 5,474,981; Gillies, S. O. et al. (1992) PNAS 89:1428–1432; Fell, H. P. et al. (1991) J. Immunol. 146:2446–2452 (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991) PNAS 88:10535–10539; Zheng, X. X. et al. (1995) J. Immunol. 154:5590–5600; and Vil, H. et al. (1992) PNAS 89:11337–11341 (said references incorporated by reference in their entireties).

The invention further relates to antibodies which act as agonists or antagonists of the polypeptides of the present invention. Antibodies which act as agonists or antagonists of the polypeptides of the present invention include, for example, antibodies which disrupt receptor/ligand interactions with the polypeptides of the invention either partially or fully. For example, the present invention includes antibodies which disrupt the ability of the proteins of the invention to multimerize. In another example, the present invention includes antibodies which allow the proteins of the invention, particularly soluble extracellular domains of the invention, to multimerize, but disrupts the ability of the proteins of the invention to bind one or more ligand(s) (e.g., IL-20). In yet another example, the present invention includes antibodies which allow the proteins of the invention to multimerize, and bind ligand(s) (e.g., IL-20), but blocks biological activity associated with the IL-20/IL17RLP receptor/ligand complex.

Antibodies which act as agonists or antagonists of the polypeptides of the present invention also include, both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also included are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al., Blood 92(6):1981–1988 (1998); Chen, Z. et al., Cancer Res. 58(16):3668–3678 (1998); Harrop, J. A. et al., J. Immunol. 161(4):1786–1794 (1998); Zhu, Z. et al., Cancer Res. 58(15):3209–3214 (1998); Yoon, D. Y. et al., J. Immunol. 160(7):3170–3179 (1998); Prat, M. et al., J. Cell. Sci. 111(Pt2):237–247 (1998); Pitard, V. et al., J. Immunol. Methods 205(2):177–190 (1997); Liautard, J. et al., Cytokinde 9(4):233–241 (1997); Carlson, N. G. et al., J. Biol. Chem. 272(17):11295–11301 (1997); Taryman, R. E. et al., Neuron 14(4):755–762 (1995); Muller, Y. A. et al., Structure 6(9):1153–1167 (1998); Bartunek, P. et al., Cytokine 8(1): 14–20 (1996) (said references incorporated by reference in their entireties).

As discussed above, antibodies to the IL17RLP proteins of the invention can, in turn, be utilized to generate anti-idiotype antibodies that "mimic" IL17RLP using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to IL17RLP and competitively inhibit multimerization and/or binding to ligand can be used to generate anti-idiotypes that "mimic" the IL17RLP mutimerization and/or binding domain and, as a consequence, bind to and neutralize IL17RLP and/or its ligand (e.g., IL-20). Such neutralizing anti-idiotypes or Fab fragments of such anti-idiotypes can be used in therapeutic regimens to neutralize IL17RLP ligand (e.g., IL-20). For example, such anti-idiotypic antibodies can be used to bind IL17RLP, or to bind IL17RLP ligands such as IL-20, and thereby block IL17RLP-mediated attraction of neutrophils and proinflammatory response.

Immune System-Related Disorders

Diagnosis

The present inventors have discovered that IL17RLP is expressed in adult pulmonary tissue. For a number of immune system-related disorders, substantially altered (increased or decreased) levels of IL17RLP gene expression can be detected in immune system tissue or other cells or bodily fluids (e.g., sera, plasma, urine, synovial fluid or spinal fluid) taken from an individual having such a disorder, relative to a "standard" IL17RLP gene expression level, that is, the IL17RLP expression level in immune system tissues or bodily fluids from an individual not having the immune system disorder. Thus, the invention provides a diagnostic method useful during diagnosis of an immune system disorder, which involves measuring the expression level of the gene encoding the IL17RLP protein in immune system tissue or other cells or body fluid from an individual and comparing the measured gene expression level with a standard IL17RLP gene expression level, whereby an increase or decrease in the gene expression level compared to the standard is indicative of an immune system disorder.

In particular, it is believed that certain tissues in mammals with cancer of the immune system express significantly enhanced levels of the IL17RLP protein and mRNA encoding the IL17RLP protein when compared to a corresponding "standard" level. Further, it is believed that enhanced levels of the IL17RLP protein can be detected in certain body fluids (e.g., sera, plasma, urine, and spinal fluid) from mammals with such a cancer when compared to sera from mammals of the same species not having the cancer.

Thus, the invention provides a diagnostic method useful during diagnosis of an immune system disorder, including cancers of this system, which involves measuring the expression level of the gene encoding the IL17RLP protein in immune system tissue or other cells or body fluid from an individual and comparing the measured gene expression level with a standard IL17RLP gene expression level, whereby an increase or decrease in the gene expression level compared to the standard is indicative of an immune system disorder.

Where a diagnosis of a disorder in the immune system including diagnosis of a tumor, has already been made according to conventional methods, the present invention is useful as a prognostic indicator, whereby patients exhibiting enhanced IL17RLP gene expression will experience a worse clinical outcome relative to patients expressing the gene at a level nearer the standard level.

By "assaying the expression level of the gene encoding the IL17RLP protein" is intended qualitatively or quantitatively measuring or estimating the level of the IL17RLP protein or the level of the mRNA encoding the IL17RLP protein in a first biological sample either directly (e.g., by determining or estimating absolute protein level or mRNA level) or relatively (e.g., by comparing to the IL17RLP protein level or mRNA level in a second biological sample). Preferably, the IL17RLP protein level or mRNA level in the first biological sample is measured or estimated and compared to a standard IL17RLP protein level or mRNA level, the standard being taken from a second biological sample obtained from an individual not having the disorder or being determined by averaging levels from a population of individuals not having a disorder of the immune system. As will be appreciated in the art, once a standard IL17RLP protein level or mRNA level is known, it can be used repeatedly as a standard for comparison.

By "biological sample" is intended any biological sample obtained from an individual, body fluid, cell line, tissue culture, or other source which contains IL17RLP protein or mRNA. As indicated, biological samples include body fluids (such as sera, plasma, urine, synovial fluid and spinal fluid) which contain free extracellular domains of IL17RLP protein, immune system tissue, and other tissue sources found to express complete, mature or extracellular domain of the IL17RLP. Methods for obtaining tissue biopsies and body fluids from mammals are well known in the art. Where the biological sample is to include mRNA, a tissue biopsy is the preferred source.

The present invention is useful for diagnosis or treatment of various immune system-related disorders in mammals, preferably humans. Such disorders include tumors, cancers, interstitial lung disease (such as Langerhans cell granulomatosis), and any disregulation of immune cell function including, but not limited to, autoimmunity, arthritis, leukemias, lymphomas, immunosuppression, immunity, humoral immunity, inflammatory bowel disease, myelo suppression, and the like.

Total cellular RNA can be isolated from a biological sample using any suitable technique such as the single-step guanidinium-thiocyanate-phenol-chloroform method described by Chomczynski and Sacchi (*Anal. Biochem.* 162:156–159 (1987)). Levels of mnRNA encoding the IL17RLP protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying IL17RLP protein levels in a biological sample can occur using antibody-based techniques. For example, IL17RLP protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting IL17RLP protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying IL17RLP protein levels in a biological sample obtained from an individual, IL17RLP protein can also be detected in vivo by imaging. Antibody labels or markers for in vivo imaging of IL17RLP protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A IL17RLP protein-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain IL17RLP protein. In vivo tumor imaging is described by Burchiel and coworkers (Chapter 13 in *Tumor Imaging: The Radiochemical Detection of Cancer*, Burchiel, S. W. and Rhodes, B. A., eds., Masson Publishing Inc. (1982)).

Treatment

As noted above, IL17RLP pplynucleotides and polypeptides are useful for diagnosis of conditions involving abnormally high or low expression of IL17RLP activities. Given the cells and tissues where IL17RLP is expressed as well as the activities modulated by IL17RLP, it is readily apparent that a substantially altered (increased or decreased) level of expression of IL17RLP in an individual compared to the standard or "normal" level produces pathological conditions related to the bodily system(s) in which IL17RLP is expressed and/or is active.

It will also be appreciated by one of ordinary skill that, since the IL17RLP protein of the invention is a member of the interleukin (IL)-17 receptor family, the extracellular domain of the protein may be released in soluble form from the cells which express the IL17RLP by proteolytic cleavage. Therefore, when IL17RLP soluble extracellular domain is added from an exogenous source to cells, tissues or the body of an individual, the protein will exert its physiological activities on its target cells of that individual. Also, cells expressing this transmembrane protein may be added to cells, tissues or the body of an individual and these added cells will bind to cells expressing IL17RLP, whereby the cells expressing IL17RLP can cause actions (e.g. cell stimulation) on the ligand-bearing target cells.

Therefore, it will be appreciated that conditions caused by a decrease in the standard or normal level of IL17RLP activity in an individual, particularly disorders of the immune system, can be treated by administration of IL17RLP polypeptide (in the form of a soluble extracellular domain or cells expressing the complete protein). Thus, the invention also provides a method of treatment of an individual in need of an increased level of IL17RLP activity comprising administering to such an individual a pharmaceutical composition comprising an amount of an isolated IL17RLP polypeptide of the invention, particularly an extracellular domain of the IL17RLP protein of the invention, effective to increase the IL17RLP activity level in such an individual.

Since IL17RLP is a novel homologue of the recently described IL-17 receptor, it will have a wide range of cytokine receptor-like activities. IL17RLP, or agonists of IL17RLP, may be employed to enhance host defenses against resistant chronic and acute infections, for example, mycobacterial infections via the attraction and activation of microbicidal leukocytes. IL17RLP may also be employed to increase T-cell proliferation by the stimulation of IL-2 biosynthesis for the treatment of T-cell mediated autoimmune diseases and lymphocytic leukemias. IL17RLP may also be employed to regulate hematopoiesis, by regulating the activation and differentiation of various hematopoietic progenitor cells, for example, to release mature leukocytes from the bone marrow following chemotherapy, i.e., in stem cell mobilization. IL17RLP may also be employed to treat sepsis. Soluble IL17RLP extracellular domains may be used as antagonists for IL17RLP activity, and, as such, will be useful therapeutically, as a mechanism to regulate the activity of endogenous IL17RLP. Also, stimulation of IL17RLP strongly induces IL-6 expression. IL-6 is a potent growth factor for myelomas, plasmacytomas, and hybridomas and is involved in the growth of Lennert's Lymphoma T-cells. As a result, IL17RLP agonists and soluble IL17RLP extracellular domains may be used in the treatment of such cancers, analogous disease states, and others known to those of skill in the art.

Formulations

The IL17RLP polypeptide composition will be formulated and dosed in a fashion consistent with good medical practice, taking into account the clinical condition of the individual patient (especially the side effects of treatment with IL17RLP polypeptide alone), the site of delivery of the IL17RLP polypeptide composition, the method of administration, the scheduling of administration, and other factors known to practitioners. The "effective amount" of IL17RLP polypeptide for purposes herein is thus determined by such considerations.

As a general proposition, the total pharmaceutically effective amount of IL17RLP polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the IL17RLP polypeptide is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the IL17RLP of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The IL17RLP polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U., et al., *Biopolymers* 22:547–556 (1983)), poly (2-hydroxyethyl methacrylate; Langer, R., et al., *J. Biomed. Mater. Res.* 15:167–277 (1981), and Langer, R., *Chem. Tech.* 12:98–105 (1982)), ethylene vinyl acetate (Langer, R., et al., Id.) or poly-D-(–)-3-hydroxybutyric acid (EP 133,988). Sustained-release IL17RLP polypeptide compositions also include liposomally entrapped IL17RLP polypeptide. Liposomes containing IL17RLP polypeptide are prepared by methods known in the art (DE 3,218,121; Epstein, et al., *Proc. Natl. Acad. Sci. (USA)* 82:3688–3692 (1985); Hwang, et al., *Proc. Natl. Acad. Sci. (USA)* 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324). Ordinarily, the liposomes are of the small (about 200–800 Angstroms) unilamellar type in which the lipid content is greater than about 30 mol. percent cholesterol, the selected proportion being adjusted for the optimal IL17RLP polypeptide therapy.

For parenteral administration, in one embodiment, the IL17RLP polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IL17RLP polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The IL17RLP polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of IL17RLP polypeptide salts.

IL17RLP polypeptide to be used for therapeutic administration must be sterile. Sterility is readily accomplished by filtration through sterile filtration membranes (e.g., 0.2 micron membranes). Therapeutic IL17RLP polypeptide compositions generally are placed into a container having a sterile access port, for example, an intravenous solution bag or vial having a stopper pierceable by a hypodermic injection needle.

IL17RLP polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous IL17RLP polypeptide solution, and the resulting mixture is lyophilized. The infusion solution is prepared by reconstituting the lyophilized IL17RLP polypeptide using bacteriostatic water-for-injection (WFI).

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of IL17RLP on cells, such as its interaction with IL17RLP-binding molecules such as ligand molecules. An agonist is a compound which increases the natural biological functions of IL17RLP or which functions in a manner similar to IL17RLP, while antagonists decrease or eliminate such functions.

In another aspect of this embodiment the invention provides a method for identifying a ligand protein which binds specifically to a IL17RLP polypeptide. For example, a cellular compartment, such as a membrane or a preparation thereof, may be prepared from a cell that expresses a molecule that binds IL17RLP. The preparation is incubated with labeled IL17RLP and complexes of IL17RLP bound to the ligand or other binding protein are isolated and characterized according to routine methods known in the art. Alternatively, the IL17RLP polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds IL17RLP, such as a molecule of a signaling or regulatory pathway modulated by IL17RLP. The preparation is incubated with labeled IL17RLP in the absence or the presence of a candidate molecule which may be a IL17RLP agonist or antagonist. The ability of the candidate molecule to bind the binding molecule is reflected in decreased binding of the labeled ligand. Molecules which bind gratuitously, i.e., without inducing the effects of IL17RLP on binding the IL17RLP binding molecule, are most likely to be good antagonists. Molecules that bind well and elicit effects that are the same as or closely related to IL17RLP are agonists.

IL17RLP-like effects of potential agonists and antagonists may by measured, for instance, by determining activity of a second messenger system following interaction of the candidate molecule with a cell or appropriate cell preparation, and comparing the effect with that of IL17RLP or molecules that elicit the same effects as IL17RLP. Second messenger systems that may be useful in this regard include but are not limited to AMP guanylate cyclase, ion channel or phosphoinositide hydrolysis second messenger systems.

Another example of an assay for IL17RLP antagonists is a competitive assay that combines an IL17RLP ligand and a potential antagonist with membrane-bound IL17RLP receptor molecules or recombinant IL17RLP receptor molecules under appropriate conditions for a competitive inhibition assay. The IL17RLP ligand can be labeled, such as by radioactivity, such that the number of IL17RLP ligand molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, without inducing IL17RLP-induced activities, thereby preventing the action of IL17RLP by excluding the IL17RLP ligand from binding.

Other potential antagonists include antisense molecules. Antisense technology can be used to control gene expression through antisense DNA or RNA or through triple-helix formation. Antisense techniques are discussed in a number of studies (for example, Okano, *J. Neurochem.* 56:560 (1991); "Oligodeoxynucleotides as Antisense Inhibitors of Gene Expression." CRC Press, Boca Raton, Fla. (1988)). Triple helix formation is discussed in a number of studies, as well (for instance, Lee, et al., *Nucleic Acids Research* 6:3073 (1979); Cooney, et al., *Science* 241:456 (1988); Dervan, et al., *Science* 251:1360 (1991)). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of IL17RLP. The antisense RNA oligonucleotide hybridizes to the mRNA in vivo and blocks translation of the mRNA molecule into IL17RLP polypeptide. The oligonucleotides described above can also be delivered to cells such that the antisense RNA or DNA may be expressed in vivo to inhibit production of IL17RLP protein.

The agonists and antagonists may be employed in a composition with a pharmaceutically acceptable carrier, e.g., as described above.

The antagonists may be employed for instance to inhibit the activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes. The antagonists may also be employed to treat infectious diseases including silicosis, sarcoidosis, idiopathic pulmonary fibrosis by preventing the activation of mononuclear phagocytes. They may also be employed to treat idiopathic hyper-eosinophilic syndrome by preventing eosinophil production. Antagonists may also be employed to treat rheumatoid arthritis by preventing the activation of monocytes in the synovial fluid in the joints of patients. Monocyte activation plays a significant role in the pathogenesis of both degenerative and inflammatory arthropathies. The antagonists may be employed to interfere with the deleterious cascades attributed primarily to IL-1 and TNF, which prevents the biosynthesis of other inflammatory cytokines. In this way, the antagonists may be employed to prevent inflammation. Antibodies against IL17RLP may be employed to bind to and inhibit IL17RLP activity to treat such conditions described above. Any of the above antagonists may be employed in a composition with a pharmaceutically acceptable carrier, e.g., as hereinafter described.

Gene Mapping

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a IL17RLP protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be. used with probes from the cDNA as short as 50 or 60 bp (for a review of this technique, see Verma, et al., *Human Chromosomes: A Manual Of Basic Techniques,* Pergamon Press, New York (1988)).

Once a sequence has been mapped to a precise chromosomal location, the physical position of the sequence on the chromosome can be correlated with genetic map data. Such data are found, for example, on the World Wide Web (McKusick, V. *Mendelian Inhetitance In Man,* available on-line through Johns Hopkins University, Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1(a)

Expression and Purification of "His-tagged" IL17RLP in *E. coli*

The bacterial expression vector pQE9 (pD10) is used for bacterial expression in this example. (QIAGEN, Inc., 9259 Eton Avenue, Chatsworth, Calif., 91311). pQE9 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag") covalently linked to the amino terminus of that polypeptide.

The DNA sequence encoding the desired portion of the IL17RLP protein comprising the extracellular domain of the IL17RLP amino acid sequence is amplified from the deposited cDNA clone using PCR oligonucleotide primers which anneal to the amino terminal sequences of the desired portion of the IL17RLP protein and to sequences in the deposited construct 3' to the cDNA coding sequence. Additional nucleotides containing restriction sites to facilitate cloning in the pQE9 vector are added to the 5' and 3' primer sequences, respectively. For cloning the extracellular domain of the IL17RLP protein, the 5' primer has the sequence 5' CGC <u>CCA TGG</u> CCG ACC GTT CAA TGT GGC TCT GAA AC 3' (SEQ ID NO:6) containing the underlined Nco I restriction site followed by 26 nucleotides of the amino terminal coding sequence of the mature IL17RLP sequence in SEQ ID NO:2. One of ordinary skill in the art would appreciate, of course, that the point in the protein coding sequence where the 5' primer begins may be varied to amplify a DNA segment encoding any desired portion of the complete IL17RLP protein shorter or longer than the extracellular domain of the protein. The 3' primer has the sequence 5' CGC <u>AAG CTT</u> CCA GCC TCC CGG CTT GC 3' (SEQ ID NO:7) containing the underlined Hind III restriction site followed by 17 nucleotides complementary to the 3' end of the coding sequence of the IL17RLP DNA sequence in FIGS. 1A, 1B, and 1C.

The amplified IL17RLP DNA fragment and the vector pQE9 are digested with Nco I and Hind III and the digested DNAs are then ligated together. Insertion of the IL17RLP DNA into the restricted pQE9 vector places the IL17RLP protein coding region downstream from the IPTG-inducible promoter and in-frame with an initiating AUG and the six histidine codons.

The ligation mixture is transformed into competent *E. coli* cells using standard procedures such as those described by Sambrook and colleagues (*Molecular Cloning: a Labora-*

*tory Manual*, 2nd Ed.; Cold Spring Harbor Laboratory Press, Cold Spring Harbor, N.Y. (1989)). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing IL17RLP protein, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 µg/ml) and kanamycin (25 µg/ml). The O/N culture is used to inoculate a large culture, at a dilution of approximately 1:25 to 1:250. The cells are grown to an optical density at 600 nm ("OD600") of between 0.4 and 0.6. Isopropyl-β-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the IL17RLP is loaded onto a nickel-nitrilo-tri-acetic acid ("Ni-NTA") affinity resin column (QIAGEN, Inc., supra). Proteins with a 6×His tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the IL17RLP is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M–1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

The following alternative method may be used to purify IL17RLP expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the IL17RLP polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded IL17RLP polypeptide solution, a previously prepared tangential filtration unit equipped with 0.16 µm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the IL17RLP polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the IL17RLP polypeptide (determined, for instance, by 16% SDS-PAGE) are then pooled.

The resultant IL17RLP polypeptide exhibits greater than 95% purity after the above refolding and purification steps. No major contaminant bands are observed from Commassie blue stained 16% SDS-PAGE gel when 5 µg of purified protein is loaded. The purified protein is also tested for endotoxin/LPS contamination, and typically the LPS content is less than 0.1 ng/ml according to LAL assays.

Example 2

Cloning and Expression of IL17RLP Protein in a Baculovirus Expression System

In this illustrative example, the plasmid shuttle vector pA2 is used to insert the cloned DNA encoding complete protein, including its naturally associated secretory signal (leader) sequence, into a baculovirus to express the mature IL17RLP protein, using standard methods as described by Summers and colleagues (*A Manual of Methods for Baculovirus Vectors and Insect Cell Culture Procedures*, Texas Agricultural Experimental Station Bulletin No. 1555 (1987)). This expression vector contains the strong polyhedrin promoter of the *Autographa californica* nuclear polyhedrosis virus (AcMNPV) followed by convenient restriction sites such as Bam HI, Xba I and Asp 718. The polyadenylation site of the simian virus 40 ("SV40") is used for efficient polyadenylation. For easy selection of recombinant virus, the plasmid contains the beta-galactosidase gene from E. coli under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, by Luckow and coworkers (*Virology* 170:31–39 (1989)).

The cDNA sequence encoding the extracellular domain of the IL17RLP protein in the deposited clone, including the AUG initiation codon and the naturally associated leader sequence shown in SEQ ID NO:2, is amplified using PCR oligonucleotide primers corresponding to the 5' and 3' sequences of the gene. The 5' primer has the sequence 5' CGC GGA TCC ATG TCG CTC GTG CTG CTA AGC CTG G 3' (SEQ ID NO:8) containing the underlined Bam HI restriction enzyme site, an efficient signal for initiation of translation in eukaryotic cells (Kozak, M., *J. Mol. Biol.* 196:947–950 (1987)), followed by 25 of nucleotides of the sequence of the complete IL17RLP protein shown in FIGS. 1A, 1B, and 1C, beginning with the AUG initiation codon. The 3' primer has the sequence 5' CGC GGT ACC CCA GCC TCC CGG CTT GC 3' (SEQ ID NO:9) containing the underlined Asp 718 restriction site followed by 17 nucleotides complementary to the 3' noncoding sequence in FIGS. 1A, 1B, and 1C.

The amplified fragment is isolated from a 1% agarose gel using a commercially available kit ("Geneclean," BIO 101 Inc., La Jolla, Calif.). The fragment then is digested with Bam HI and Asp 718 and again is purified on a 1% agarose gel. This fragment is designated herein F1.

The plasmid is digested with the restriction enzymes Bam HI and Asp 718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Statagene Cloning Systems, La Jolla, Calif.) cells are transformed with the ligation mixture and spread on culture plates. Bacteria are identified that contain the plasmid with the human IL17RLP gene by digesting DNA from individual colonies using Bam HI and Asp 718 and then analyzing the digestion product by gel electrophoresis. The sequence of the cloned fragment is confirmed by DNA sequencing. This plasmid is designated herein pA2IL17RLP.

Five µg of the plasmid pA2IL17RLP is co-transfected with 1.0 µg of a commercially available linearized baculovirus DNA ("BaculoGold™ baculovirus DNA", Pharmingen, San Diego, Calif.), using the lipofection method described by Felgner and colleaguew (*Proc. Natl. Acad. Sci. USA* 84:7413–7417 (1987)). One µg of BaculoGold™ virus DNA and 5 µg of the plasmid pA2IL17RLP are mixed in a sterile well of a microtiter plate containing 50 µl of serum-free Grace's medium (Life Technologies Inc., Gaithersburg, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith (supra). An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-IL17RLP.

To verify the expression of the IL17RLP gene Sf9 cells are grown in Grace's medium supplemented with 10% heat-inactivated FBS. The cells are infected with the recombinant baculovirus V-IL17RLP at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 µCi of $^{35}$S-methionine and 5 µCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the extracellular domain of the IL17RLP protein, and thus the cleavage point and length of the naturally associated secretory signal peptide.

Example 3
Cloning and Expression of IL17RLP in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS; Murphy, et al., *Biochem J.* 227:277–279 (1991); Bebbington, et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen, et al., *Mol. Cel. Biol.* 5:438–447 (1985)) plus a fragment of the CMV-enhancer (Boshart, et al., *Cell* 41:521–530 (1985)). Multiple cloning sites, e.g., with the restriction enzyme cleavage sites Bam HI, Xba I and Asp 718, facilitate the cloning of the gene of interest. The vectors contain in addition the 3' intron, the polyadenylation and termination signal of the rat preproinsulin gene.

Example 3(a)
Cloning and Expression in COS Cells

The expression plasmid, pIL17RLPHA, is made by cloning a portion of the cDNA encoding the extracelluar domain of the IL17RLP protein into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson and colleagues (*Cell* 37:767 (1984)). The fusion of the HA tag to the target protein allows easy detection and recovery of the recombinant protein with an antibody that recognizes the HA epitope. pcDNAIII contains, in addition, the selectable neomycin marker. A DNA fragment encoding the extracellular domain of the IL17RLP polypeptide is cloned into the polylinker region of the vector so that recombinant protein expression is directed by the CMV promoter. The plasmid construction strategy is as follows. The IL17RLP cDNA of the deposited clone is amplified using primers that contain convenient restriction sites, much as described above for construction of vectors for expression of IL17RLP in *E. coli*. Suitable primers include the following, which are used in this example. The 5' primer, containing the underlined Bam HI site, a Kozak sequence, an AUG start codon, and 25 nucleotides of the 5' coding region of the extracellular domain of the IL17RLP polypeptide, has the following sequence: 5' GCC GGA TCC GCCACC ATG AAC TCC TTC TCC ACA AGC GCC TTC GGT CCA GTT GCC TTC TCC CTG GGG CTG CTC CTG GTG TTG CCT GCT GCC TTC CCT GCC CCA GTA TGT CGC TCG TGC TGC TAA GCC TGG 3' (SEQ ID NO:10). The 3' primer, containing the underlined Asp 718 and 17 of nucleotides complementary to the 3' coding sequence immediately before the stop codon, has the following sequence: 5' GGC CGG GTA CCC CAG CCT CCC GGC TTG C 3' (SEQ ID NO:11).

The PCR amplified DNA fragment and the vector, pcDNAI/Amp, are digested with Bam HI and Asp 718 and then ligated. The ligation mixture is transformed into *E. coli* strain SURE (Stratagene Cloning Systems, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the extracellular domain of the IL17RLP polypeptide For expression of recombinant IL17RLP, COS cells are transfected with an expression vector, as described above, using DEAE-dextran, as described, for instance, by Sambrook and coworkers (*Molecular Cloning: a Laboratory Manual*, Cold Spring Laboratory Press, Cold Spring Harbor, N.Y. (1989)). Cells are incubated under conditions for expression of IL17RLP by the vector.

Expression of the IL17RLP-HA fusion protein is detected by radiolabeling and immunoprecipitation, using methods described in, for example Harlow and colleagues (*Antibodies: A Laboratory Manual*, 2nd Ed.; Cold Spring Harbor Laboratory Press, Cold Spring Harbor, N.Y. (1988)). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson and colleagues (supra). Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)
Cloning and Expression in CHO Cells

The vector pC4 is used for the expression of IL17RLP polypeptide. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., et al., *J. Biol. Chem.* 253:1357–1370 (1978); Hamlin, J. L. and Ma, C. *Biochem. et Biophys. Acta*, 1097:107–143 (1990); Page, M. J. and Sydenham, M. A. *Biotechnology* 9:64–68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s).

Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Mol. Cell. Biol.* 5:438–447 (1985)) plus a fragment isolated from the enhancer of the immediate early gene of human cytomegalovirus (CMV; Boshart, et al., *Cell* 41:521–530 (1985)). Downstream of the promoter are the following single restriction enzyme cleavage sites that allow the integration of the genes: Bam HI, Xba I, and Asp 718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the IL17RLP polypeptide in a regulated way in mammalian cells (Gossen, M., and Bujard, H. *Proc. Nati. Acad. Sci. USA* 89:5547–5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes Bam HI and Asp 718 and then dephosphorylated using calf intestinal phosphates by procedures known in the art. The vector is then isolated from a 1% agarose gel.

The DNA sequence encoding the extracellular domain of the IL17RLP polypeptide is amplified using PCR oligonucleotide primers corresponding to the 5' and 3' sequences of the desired portion of the gene. The 5' primer containing the underlined Bam HI site, a Kozak sequence, an AUG start codon, and 25 nucleotides of the 5' coding region of the extracellular domain of the IL17RLP polypeptide, has the following sequence: 5' CTA GCC GGA TCC GCCACC ATG TCG CTC GTG CTG CTA AGC CTG G 3' (SEQ ID NO:12). The 3' primer, containing the underlined Asp 718 and 17 of nucleotides complementary to the 3' coding sequence immediately before the stop codon as shown in FIGS. 1A, 1B, and 1C (SEQ ID NO:1), has the following sequence: 5' GGC CGG GTA CCC CAG CCT CCC GGC TTG C 3' (SEQ ID NO:13).

The amplified fragment is digested with the endonucleases Bam HI and Asp 718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Felgner, et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 mM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 4
Tissue Distribution of ILL17RLP mRNA Expression

Northern blot analysis is carried out to examine IL17RLP gene expression in human tissues, using methods described by, among others, Sambrook and colleagues (supra). A cDNA probe containing the entire nucleotide sequence of the IL17RLP protein (SEQ ID NO:1) is labeled with $^{32}$P using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for IL17RLP mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

In Northern blot experiments performed essentially as described above, expression of the IL17RLP transcript was detected in pancreas, kidney, liver, and fetal liver. Lower expression was also observed in other endocrine organs.

Example 5
Blocking Effect of Soluble IL17RLP on IL-20-induced Neutrophil Migration and Macrophage Activation in the Mouse Peritoneum An analysis of the use of soluble IL17RLP ("sIL17RLP") as an anti-inflammatory agent is performed through the use of a human IL-20 ("hIL-20")-induced inflammation model in mice. Our recent experiment indicate that, when given intraperitoneally, hIL-20 induces a significant migration of neutrophils into the mouse peritoneum at 4 hours after injection as observed by both FACS and Wright-Giemsa stained cytospin analysis. In addition, after hIL-20 challenge, peritoneal macrophages show activation signals by morphology. Soluble sIL17RLP is expected to bind hIL-20 and inhibit hIL-20-induced neutrophil migration and macrophage activation.

Initiation of the inflammation condition is induced by a single intraperitoneal injection of high (25 μg) and low doses (1–10 μg) of hIL-20 into BALB/c mice. Groups of 4 mice receive either 0.1 to 10 mg/kg of sIL17RLP, solulbe human IL-17 receptor or negative control human receptor, intraperitoneally once between 0 and 2 hours prior to hIL-20 injection. The effect of sIL17RLP on neutrophil migration and macrophage activation in the peritoneum is analyzed at 4, 16, 24 or 48 hours by FACS and cytospin method. Briefly, for FACS analysis, collected peritoneal cells are stained with fluorescein phycoerythrin-conjugated antibodies against MHC class II (I-A/I-E) and FITC-conjugated anti-Mac-I or anti-Gr1 (PharMingen (San Diego, Calif.)). Cells are then

Example 6
Effect of Soluble IL17RLP on Adjuvant-induced Arthritis

An analysis of the use of soluble IL17RLP ("sIL17RLP") to treat rheumatoid arthritis (RA) is performed through the use of an adjuvant-induced arthritis model (AIA) in rats. AIA is a well-characterized and reproducible animal model of rheumatoid arthritis, which is well known to one of ordinary skill in the art (Pearson, et al., *Ann. Rheum. Dis.* 15:379, (1956)); Pearson, et al., *Arthritis Rheum.* 2:440, (1959)). sIL17RLP is expected to bind to hIL-20 and inhibit IL-20-induced synoviocyte activation and cytokine production, which may involve in the perpetuation of chronic arthritis. Lewis rats (available from Charles River Lab, Raleigh, N.C.) are used as the common and responsive strains for adjuvant-induced arthritis in these experiments.

Initiation of the arthritis condition is induced by the intradermal injection of 0.1 ml adjuvant (5 mg/ml) into the base of the tail. Groups of 5 to 6 rats received either 0.1 to 10 mg/kg sIL17RLP or vehicle intra-articularly 10 days after the injection of adjuvant when the acute inflammation just begins. The effect of sIL17RLP on chronic arthritis is analyzed radiologically once each week between day 15–30 essentially as described by Taurog and colleagues (*J. Exp. Med.* 162:962, (1985)). Briefly, rats are anesthetized with ether or chloral hydrate and positioned so that both hind limbs are X-rayed together. The X-ray films are examined blindly using a scoring system of 0–3 for periosteal reaction, bony erosions, joint space narrowing and destruction. When there is a significant amount of joint damage in vehicle-treated rats, the animals are sacrificed. At this point, the paws are evaluated histologically for the relative degree of tissue damage and for the therapeutic effect sIL17RLP has elicited on these joints. Finally, sIL17RLP- and vehicle-treated animals undergo a clinical evaluation twice per week to assess hind paw volume using a plethysmometer system and body weight.

Alternatively, rheumatoid synoviocytes are isolated from RA patients undergoing knee or wrist synovectomy and cultured in 150 cm$^2$ flasks. Nonadherent cells are removed and adherent cells are trypsinized at confluence and passaged. Synoviocytes used between passages 3 and 8 constitute a homogenous population of fibroblast-like cells. Synoviocytes are cultured in 96-well plates in a final volume of 200 μl of the medium. Human IL-20 polypeptides (or human IL-17 as a control) are added at different concentrations to the medium at the onset of the culture. In experimental flasks, human sIL17RLP polypeptide is also added to the culture medium. Subsequently, cell-free supernatants are collected after 72 hr, and stored at −20° C. for further use in cytokine assays. Concentrations of IL-6 and IL-8 are measured by ILISA. A decrease in IL-6 and/or IL-8 levels in the culture supernatant indicates that the sIL17RLP polypeptide inhibits the IL-20-mediated increase in IL-6 and/or IL-8 production in this culture system. Consequently, sIL17RLP may be useful to treat rheumatoid arthritis and other related immunoregulatory disorders and diseases.

Example 7
Effect of Soluble IL17RLP in Treating Graft versus Host Disease in Mice An analysis of the use of soluble IL17RLP ("sIL17RLP") to treat graft-versus-host disease (GVHD) is performed through the use of a C57BL/6 parent into (BALB/c X C57BL/6) F1 mouse model. This parent into F1 mouse model is a well-characterized and reproducible animal model of GVHD in bone marrow transplant patients, which is well know to one of ordinary skill in the art (see, Gleichemann, et al., *Immunol. Today* 5:324, (1984)). IL17RLP is structurally related to the IL-17R which, in soluble form, has a beneficial effect on the prolongation of allograft survival in association with its inhibiting effect on alloantigen-induced lymphocyte proliferation. sIL17RLP is expected to inhibit the activation of the donor T cells to host MHC class II antigen (alloantigen) which play a crucial role in the pathogenesis of GVHD.

Initiation of the experimental GVHD condition is induced by the intravenous injection of ~1–3×10$^8$ spleen cells from C57BL/6 mice into (BALB/c X C57BL/6) F1 mice (available from Jackson Lab, Bar Harbor, Me.). Groups of 6 to 8 mice received either 0.1 to 5.0 mg/kg of sIL17RLP or negative control intraperitoneally daily following the injection of spleen cells. The effect of sIL17RLP on lymphoid hypoplasia and atrophy of spleen is analyzed by FACS and histopathology at multiple time points (3–4) between days 10 and 30. Briefly, splenocytes are prepared from normal CBF1 mice, GVHD mice or sIL17RLP-treated mice; and stained with fluorescein phycoerythrin-conjugated anti-H-2Kb, biotin-conjugated anti-H-2Kd, and FITC-conjugated anti-CD4, anti-CD8, or anti-B220, followed by a CyChrome-conjugated avidin (PharMingen (San Diego, Calif.)). Cells are then analysis on a FACScan (Becton Dickinson, San Jose, Calif.). Recipient and donor lymphocytes are identified as H-2Kb+Kd+ and H-2Kb+Kd− cells, respectively. Cell numbers of CD4+T, CD8+T and B220+B cells of recipient or donor origin are calculated from the total numbers of splenocytes recovered and the percentages of each subpopulation are determined by the three color analysis. Histological evaluation of the relative degree of tissue damage in other GVHD-associated organs (liver, skin and intestine) may be conducted after sacrificing the animals for the beneficial potential of sIL17RLP on these organs.

In addition, the effect of sIL17RLP on spontaneous proliferation and IL-2 production of host splenocytes is analyzed between day 2–10. Finally, sIL17RLP− and its negative control-treated animals undergo a clinical evaluation every other day to assess cachexia, body weight and lethality. Soluble sIL17RLP in combination therapy with immunosuppressive agents may also be examed in this GVHD murine model.

Example 8
Analysis of IL-17RLP Ligand Candidates

IL17RLP ligand candidates are screened for binding using BIACORE technology which enables one to monitor binding events between two or more molecules, in real time, without the use of labels. BIACORE technology relies on the phenomenon of surface plasmon resonance (SPR) which occurs when surface plasmon waves are excited at a metal/liquid interface. Light is directed at, and reflected from, the side of the surface not in contact with sample, and SPR causes a reduction in the reflected light intensity at a specific combination of angle and wavelength. Biomolecular binding events cause changes in the refractive index at the surface layer, which are detected as changes in the SPR signal.

The conditioned culture supernatants from three IL-20 CHO (see copending U.S. patent application Ser. No. 09/115,832) clones (numbers 10, 16 and 22), as well as, IL-17 (purchased from R&D) were analyzed for binding to IL17-like receptors. The data indicate that compared to the negative control conditioned media (pC4 vector alone) that all clones showed greater binding. The binding was approximately 115 RU for clones 16 and 22, ~65 RU for clone 10 and ~20 RU for pC4. This binding was greater than that found for IL-17 which was ~60 RU measured at 25 ug/mL. The exact concentration of IL-20 in the culture supernatants is not known but is estimated to be comparable to IL-17, i.e., ~25 ug/mL. This result suggests that the IL-17 receptor binds both ligands, and may even bind IL-20 better.

The binding of IL-20 and IL-17 to L-17 receptor (IL17R-Fc) and IL17RLP fused to the human immunoglobulin domain (IL 17RLP-Fc) after immobilization of the receptor on a BIACORE flow cell. Two CHO cell IL-20 preparations were first analyzed as they contain different N-terminal forms of the protein. IL-17 (R&D) ligand was also analyzed. The results indicate that IL-20 predominately bound to IL17RLP-Fc and to a much lesser extent to IL-17R. The dissociation of IL-20 from the IL17RLP-Fc appeared to be biphasic for both batches which might be due to the presence different N-terminally truncated forms of the protein present in both batches. In contrast, IL-17 bound almost exclusively to the IL-17R which little or no binding to IL17RLP-Fc.

Thus, these results suggest that IL-20 interacts with the IL-17 receptor and the IL17RLP described herein. As a result, IL17RLP, or soluble fragments thereof, may be useful to modulate the receptor activation pathways in which these receptors are involved. IL17RLP polypeptides of the invention may be used as an antagonist for binding IL-20 polypeptides and/or other related or unrelated polypeptides which interact with this receptor or the IL-20 ligand, e.g., IL-17. IL17RLP polypeptides of the invention may thus be useful in the diagnosis and/or treatment of immune disorders involving the IL-17 and IL17RLP molecules as known in the art and as described above.

Example 9
Gene Therapy Using the Endogenous IL17RLP Gene

Another method of gene therapy according to the present invention involves operably associating the endogenous IL17RLP sequence with a promoter via homologous recombination as described, for example, in U.S. Pat. No. 5,641,670, issued Jun. 24, 1997; International Publication Number WO 96/29411, published Sep. 26, 1996; International Publication Number WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous IL17RLP, flanking the promoter. The targeting sequence will be sufficiently near the 5' end of IL17RLP so the promoter will be operably linked to the endogenous sequence upon homologous recombination. The promoter and the targeting sequences can be amplified using.PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous IL17RLP sequence. This results in the expression of W17RLP in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the IL17RLP locus, plasmid pUC18 (MBI Fernentas, Amherst, N.Y.) is digested with Hindif. The CMV promoter is amplified by PCR with an XbaI site on the 5' end and a BamHI site on the 3'end. Two IL17RLP non-coding sequences are amplified via PCR: one IL17RLP non-coding sequence (IL17RLP fragment 1) is amplified with a HindIII site at the 5' end and an Xba site at the 3'end; the other IL17RLP non-coding sequence (IL17RLP fragment 2) is amplified with a BamHI site at the 5'end and a HindIII site at the 3'end. The CMV promoter and IL17RLP fragments are digested with the appropriate enzymes (CMV promoter—XbaI and BamHI; IL17RLP fragment 1—XbaI; IL17RLP fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 $\mu$g/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 $\mu$F and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith, and the Sequence Listings submitted with U.S. application Ser. No. 09/154,219, filed on Sep. 16, 1998; U.S. Provisional Application Serial No. 60/059,133, filed on Sep. 17, 1997, in both computer and paper forms are hereby incorporated by reference in their entireties.

What is claimed is:

1. An isolated protein comprising an amino acid sequence of amino acid residues +1 to +271 of SEQ ID NO:2.

2. The protein of claim 1 wherein said amino acid sequence further comprises a heterologous polypeptide.

3. The protein of claim 2 wherein said heterologous polypeptide is the Fc domain of immunoglobulin.

4. The isolated protein of claim 1 wherein said isolated protein is glycosylated.

5. The isolated protein of claim 1 wherein said isolated protein is fused to polyethylene glycol.

6. A composition comprising the isolated protein of claim 1 and a pharmaceutically acceptable carrier.

7. A protein produced by a method comprising:
    (a) culturing a host cell under conditions suitable to produce the protein of claim 1, and
    (b) recovering the protein.

8. An isolated protein comprising an amino acid sequence of an amino acid sequence of the extracellular domain of the protein encoded by the cDNA in ATCC Deposit No. 209198.

9. The isolated protein of claim 8 wherein said amino acid sequence further comprises a heterologous polypeptide.

10. The isolated protein of claim 9 wherein said heterologous polypeptide is the Fc domain of immunoglobulin.

11. The isolated protein of claim 8 wherein said isolated protein is glycosylated.

12. The isolated protein of claim 8 wherein said isolated protein is fused to polyethylene glycol.

13. A composition comprising the isolated protein of claim 8 and a pharmaceutically acceptable carrier.

14. A protein produced by a method comprising:
    (a) culturing a host cell under conditions suitable to produce the protein of claim 8, and
    (b) recovering the protein.

15. An isolated protein comprising an amino acid sequence 90% or more identical to an amino acid sequence of amino acid residues +1 to +271 of SEQ ID NO:2 wherein said protein has IL-20 binding activity.

16. The isolated protein of claim 15 comprising an amino acid sequence at least 95% or more identical to amino acid residues +1 to +271 of SEQ ID NO 2.

17. The isolated protein of claim 15 wherein said amino acid sequence further comprises a heterologous polypeptide.

18. The isolated protein of claim 17 wherein said heterologous polypeptide is the Fc domain of immunoglobulin.

19. The isolated protein of claim 15 wherein said isolated protein is glycosylated.

20. The isolated protein of claim 15 wherein said isolated protein is fused to polyethylene glycol.

21. A composition comprising the isolated protein of claim 15 and a pharmaceutically acceptable carrier.

22. A protein produced by a method comprising:
    (a) culturing a host cell under conditions suitable to produce the protein of claim 15; and
    (b) recovering the protein.

23. An isolated protein comprising an amino acid sequence 90% or more identical to an amino acid sequence of the amino acid sequence of the extracellular domain of the protein encoded by the cDNA in ATCC Deposit No. 209198 wherein said protein has IL-20 binding activity.

24. The isolated protein of claim 23 which comprises an amino acid sequence 95% or more identical to the amino acid sequence of the extracellular domain of the protein encoded by the cDNA in ATCC Deposit No 209198.

25. The polypeptide of claim 23 wherein said amino acid sequence further comprises a heterologous polypeptide.

26. The polypeptide of claim 25 wherein said heterologous polypeptide is the Fc domain of immunoglobulin.

27. The isolated protein of claim 23 wherein said isolated protein is glycosylated.

28. The isolated protein of claim 23 wherein said isolated protein is fused to polyethylene glycol.

29. A composition comprising the isolated protein of claim 23 and a pharmaceutically acceptable carrier.

30. A protein produced by a method comprising:
    (a) culturing a host cell under conditions suitable to produce the protein of claim 23, and
    (b) recovering the protein.

31. An isolated protein comprising an amino acid sequence, wherein, except for one to thirty amino acid substitutions, additions, or deletions in any combination, said amino acid sequence is identical to contiguous amino acid residues of amino acid residues +1 to +271 of SEQ ID NO:2 wherein said protein has IL-20 binding activity.

32. The protein of claim 31 further comprising a heterologous polypeptide sequence.

33. The protein of claim 32 wherein said heterologous polypeptide is the Fc domain of immunoglobulin.

34. The isolated protein of claim 31 wherein said isolated protein is glycosylated.

35. The isolated protein of claim 31 wherein said isolated protein is fused to polyethylene glycol.

36. A composition comprising the isolated protein of claim 31 and a pharmaceutically acceptable carrier.

37. A protein produced by a method comprising:
  (a) culturing a host cell under conditions suitable to produce the protein of claim 31, and
  (b) recovering the protein.

38. An isolated protein comprising an amino acid sequence, wherein, except for one to thirty amino acid substitutions, additions, or deletions in any combination, said amino acid sequence is identical to contiguous amino acid residues of an amino acid sequence of the extracellular domain of the polypeptide encoded by the cDNA in ATCC Deposit No. 209198 wherein said protein has IL-20 binding activity.

39. The protein of claim 37 further comprising a heterologous polypeptide sequence.

40. The protein of claim 39 wherein said heterologous polypeptide is the Fc domain of immunoglobulin.

41. The isolated protein of claim 39 wherein said isolated protein is glycosylated.

42. The isolated protein of claim 38 wherein said isolated protein is fused to polyethylene glycol.

43. A composition comprising the isolated protein of claim 38 and a pharmaceutically acceptable carrier.

44. A protein produced by a method comprising:
  (a) culturing a host cell under conditions suitable to produce the protein of claim 38; and
  (b) recovering the protein.

* * * * *